United States Patent
Ramsburg et al.

(10) Patent No.: US 11,591,377 B2
(45) Date of Patent: Feb. 28, 2023

(54) HETEROLOGOUS ADMINISTRATION OF TAU VACCINES

(71) Applicants: Janssen Pharmaceuticals, Inc., Titusville, NJ (US); AC Immune SA, Lausanne (CH)

(72) Inventors: Elizabeth Anne Ramsburg, Chalfont, PA (US); Donata De Marco, Turnhout (BE); Chakkumkal Anish, The Hague (NL); Charlotte Sadaka, San Diego, CA (US); Jaap Goudsmit, Amsterdam (NL); Andreas Muhs, Cugy (CH); Maria Pihlgren Bosch, Mont-Sur-Lausanne (CH); Marija Vukicevic Verhille, St-Sulpice (CH); David Hickman, St-Sulpice (CH); Nicolas Piot, Grandvaux (CH); Saroj Raj Ghimire, Chavannes-Pres-Renens (CH)

(73) Assignees: Janssen Pharmaceuticals, Inc., Titusville, NJ (US); AC Immune SA, Lausanne (CH)

( * ) Notice: Subject to any disclaimer, the term of this patent is extended or adjusted under 35 U.S.C. 154(b) by 0 days.

(21) Appl. No.: 16/856,400

(22) Filed: Apr. 23, 2020

(65) Prior Publication Data
US 2020/0339643 A1    Oct. 29, 2020

Related U.S. Application Data

(60) Provisional application No. 62/837,987, filed on Apr. 24, 2019.

(51) Int. Cl.
*C07K 14/47* (2006.01)
*A61K 39/00* (2006.01)
*A61K 9/127* (2006.01)

(52) U.S. Cl.
CPC ........ *C07K 14/4711* (2013.01); *A61K 9/1271* (2013.01); *A61K 39/0007* (2013.01); *A61K 2039/55516* (2013.01); *A61K 2039/55561* (2013.01); *A61K 2039/55572* (2013.01); *A61K 2039/6018* (2013.01); *A61K 2039/627* (2013.01)

(58) Field of Classification Search
CPC .............. A61K 39/0007; A61K 9/1271; A61K 2039/55516; A61K 2039/55561; A61K 2039/55555; A61K 2039/55572; A61K 2039/6018; A61K 2039/6037; A61K 2039/6081; C07K 14/4711
See application file for complete search history.

(56) References Cited

U.S. PATENT DOCUMENTS

| | | |
|---|---|---|
| 5,843,779 A | 12/1998 | Vandermeeren et al. |
| 7,408,027 B1 | 8/2008 | Mandelkow et al. |
| 7,741,297 B2 | 6/2010 | Jiang |
| 8,647,631 B2 | 2/2014 | Pfeifer |
| 9,687,447 B2 | 6/2017 | Reis |
| 11,124,552 B2 | 9/2021 | Ramsburg et al. |
| 2002/0086009 A1 | 7/2002 | Ishiguro et al. |
| 2003/0232758 A1 | 12/2003 | St. George-Hyslop et al. |
| 2004/0265920 A1 | 12/2004 | Seubert et al. |
| 2005/0221391 A1 | 10/2005 | Davies |
| 2005/0261475 A1 | 11/2005 | Tseng et al. |
| 2006/0073158 A1 | 4/2006 | Nicolau et al. |
| 2008/0050383 A1 | 2/2008 | Sigurdsson et al. |
| 2008/0220449 A1 | 9/2008 | Vasan et al. |
| 2010/0316564 A1 | 12/2010 | Sigurdsson et al. |
| 2012/0183599 A1 | 7/2012 | Pfeifer |
| 2016/0347804 A1 | 12/2016 | Griswold-Prenner |
| 2019/0112362 A1 | 4/2019 | Adolfsson |
| 2019/0119341 A1 | 4/2019 | Ramsburg |
| 2020/0376078 A1 | 12/2020 | Ramsburg et al. |
| 2021/0388044 A1 | 12/2021 | Ramsburg et al. |

FOREIGN PATENT DOCUMENTS

| | | |
|---|---|---|
| EP | 2210901 A1 | 7/2010 |
| WO | 9014837 A1 | 12/1990 |
| WO | 1996020218 A1 | 7/1996 |
| WO | 1997034145 A1 | 9/1997 |
| WO | 1998022120 A1 | 5/1998 |
| WO | 2003066649 A1 | 8/2003 |
| WO | 2005080986 A1 | 9/2005 |
| WO | 2005081872 A2 | 9/2005 |
| WO | 2007068105 A1 | 6/2007 |
| WO | 2007068411 A2 | 6/2007 |
| WO | 2010106127 A2 | 9/2010 |

(Continued)

OTHER PUBLICATIONS

Hermanson, Greg T. Bioconjugate Techniques, 3rd Edition, Sand Diego: Elsevier Science & Technology, 2013. Chapter 6: Heterobifunctional Crosslinkers, pp. 299-339. (Year: 2013).*
Lu, Shan. Heterologous prime-boost vaccination. Curr. Opin. Immunol. 2009, 21(3):346-351. (Year: 2009).*
Asuni et al., "Immunotherapy Targeting Pathological Tau Conformers in a tangle Mouse Model Reduces Brain Pathology with Associated Functional Improvements," Journal of Neuroscience, vol. 27, No. 34, pp. 9115-9129 (2007).
Bhaskar et al., "Tyrosine Phosphorylation of Tau Accompanies Disease Progression in Transgenic Mouse Models of Tauopathy," Neuropathology and Applied Neurobiology, vol. 36, No. 6, pp. 462-477 (2012).

(Continued)

*Primary Examiner* — Kimberly Ballard
(74) *Attorney, Agent, or Firm* — Ice Miller LLP

(57) ABSTRACT

Methods for inducing an immune response against tau protein in a subject suffering from a neurodegenerative disease, disorder or condition, such as Alzheimer's Disease, are described. The methods include administering a liposomal priming composition containing tau peptides, preferably phosphorylated tau peptides, and a conjugate boosting composition containing tau peptides, preferably phosphorylated tau peptides, conjugated to an immunogenic carrier.

20 Claims, 7 Drawing Sheets

Specification includes a Sequence Listing.

(56) References Cited

FOREIGN PATENT DOCUMENTS

| WO | 2010115843 A2 | 10/2010 |
|---|---|---|
| WO | 2010144711 A2 | 12/2010 |
| WO | 2011013034 A1 | 2/2011 |
| WO | 2012020124 A1 | 2/2012 |
| WO | 2012055933 A1 | 5/2012 |
| WO | 2015197823 A2 | 12/2015 |
| WO | 2018106781 A1 | 6/2018 |
| WO | 2019094595 A2 | 5/2019 |

OTHER PUBLICATIONS

Boimel et al., "Efficacy and safety of immunization with phosphorylated tau against neurofibrillary tangles in mice," Experimental Neuroology, vol. 224, pp. 472-485 (2010).

Clinical Trials, "Safety Study of AADvac1, a Tau Peptide-KLH-Conjugate Active Vaccine to Treat Alzheimer's Disease", https://www.clinicaltrials.gov/ct2/show/record/nct01850238?view=record, ClinicalTrials.gov Identifier: NCT01850238, Oct. 2015.

De Titta et al., "Nanoparticle Conjungation of CpG Enhances Adjuvancy from Cellular Immunity and Memory Recall at Low Dose", PNAS, vol. 110, No. 49, pp. 19902-19907 (2013).

Dominguez et al., "Novel Thereapeutic Strategies Provide the Real Test for the Amyloid Hypothesis Alzheimer's Disease," Trends in Pharmacological Sciences, vol. 23, No. 7, pp. 324-330 (2002).

Friedhoff et al., "Structure of tau protein and assembly into paired helical filaments", Biochimica et Biophysica Acta, 1502, pp. 122-132, 2000.

Gandhi et al., "A Phosphorylation-Induced Turn Defines the Alzheimer's Disease AT8 Antibody Epitope on the Tau Protein," Angew Chem Int Ed Engl, vol. 54, No. 23, pp. 6819-6823 (2015).

Hanger et al., "Tau phosphorylation: the therapeutic challenge for neurodegenerative disease" Trends in Molecular Medicine, vol. 15, No. 3, pp. 112-119 (2009).

Hickman et al., "Sequence-independent Conftrol of Peptide Conformation in Liposomal Vaccines for Targeting Protein Misfolding Diseases," The Journal of Biological Chemistry, vol. 286, No. 16, pp. 13966-13976 (2011).

Hills et al., "A Rapid-Response Humoral Vaccine Platform Exploiting pre-Existing Non-Cognate Populations of Anti-Vaccine or Anti-Viral CD4+ T Helper Cells to confirm B Cell Activation," PLOS One, 20 pages, Nov. 18, 2016.

Hirata-Fukae et al., "Levels of Soluble and Insoluble Tau Reflect Overall Status of Tau Phosphorylation in Vivo," Neuroscience Letters, vol. 450, No. 1, pp. 51-55 (2009).

Hoffman et al., "Unique Alzheimer's Disease Paired Helical Filament Specific Epitopes Involve Double Phosphorylation at Specific Sites," Biochemistry, vol. 36, No. 26, pp. 8114-8124 (1997).

Jicha et al., "Camp-Dependent Protein Kinase Phosphorylations on Tau in Alzheimer's Disease," Journal of Neuroscience, vol. 19, No. 17, pp. 7486 (1999).

Kontsekova et al., "Identification of structural determinants on tau protein essential for its pathological function: novel therapeutic target for tau immunotherapy in Alzheimer's Disease," Alzheimer's research & therapy, vol. 6, No. 45, pp. 1-16 (2014).

Lee et al., "Phosphorylation of Tau by Fyn: Implications for Alzheimer's Disease," Journal of Neuroscience, Mar. 3, 2004, vol. 24, No. 9, pp. 2304-2312.

Lewis et al., "Neurofibrillary Tangles, Amyotrophy and Progressive Motor Disturbance in Mice Expressing Mutant (P301L) Tau Protein," Nature America, Inc., vol. 25, pp. 402-405 (2000).

Lichtenberg-Kraag et al., "Phosphorylation-Dependent Epitopes of Neurofilament Antibodies on Tau Protein and Relationship with Alzheimer Tau," PNAS, vol. 89, No. 12, pp. 5384-5388 (1992).

Masliah et al., "Effects of a-Synuclein Immunization in a Mouse Model of Parkinson's Disease," Neuron, vol. 46, pp. 857-868 (2005).

Matyas et al., "Liposomes containing monophosphoryl lipid A: A Potent adjuvant system for inducing antibodies to heroin hapten analogs", Vaccine, vol. 21, pp. 2804-2810 (2013).

Muhs et al., "Liposomal Vaccines with Conformation-Specific Amyloid Peptide Antigens Define Immune Response and Efficacy in APP Transgenic Mice," PNAS, vol. 104, No. 23, pp. 9810-9815 (2007).

Muyllaert et al., "Glycogen Synthase Kinase-3p, or a Link Between Amyloid and Tau Pathology?" Genes, Brain and Behavior, vol. 7, Suppl. 1, pp. 57-66 (2008).

Muyllaert et al., "Transgenic Mouse Models for Alzheimer's Disease: the Role of GSK-3p in Combined Amyloid and Tau-Pathology," Rev Neurol (Paris), vol. 162, No. 10, pp. 903-907 (2006).

Nakamura et al., "Cisphosphorylated tau as the earliest detectable pathogenic conformation in Alzheimer disease, offering novel diagnostic and therapeutic strategies," Prion, vol. 7, No. 2, pp. 117-120 (2013).

Neeland et al., "Incorporation of CpG into a Liposomal Vaccine Formulation Increases the Maturation of Antigen-Loaded dendritic Cells and Monocytes to Improve Local and Systemic Immunity", Journal of Immunology, vol. 192, pp. 3666-3675 (2014).

Nicolau et al., "A Liposome-Based Therapeutic Vaccine Against (3-Amyloid Plaques on the Pancreas of Transgenic Mice," PNAS, vol. 99, No. 4, pp. 2332-2337 (2012).

Nicoll et al., "Neuropathology of Human Alzheimer Disease After Immunization with Amyloid-p Peptide: A Case Report," Nature Medicine, vol. 9, No. 4, pp. 448-452 (2003).

Novak et al., "Characterisation of the Antibody Response to Aadvac1: The First-in-Kind Active Vaccine Against Neurofibrillary Tau Pathology", Alzeheimer's & Dementia: The Journal of The Alzheimer's Association, vol. 12, No. 7, pp. P351 (2016).

Novak et al., "Safety and immunogenicity of the tau vaccine AADvac1 in patients with Alzheimer's disease: randomised, double-blind, placebo-controlled, phase 1 trail," Lancet Neurol, vol. 16, pp. 123-134 (2017).

Oddo et al., "A-beta Immunotherapy Leads to Clearance of Early, but Not Late, Hyperphosporylated Tau Aggregates via the Proteasome," Neuron, vol. 43, pp. 321-332 (2004).

Oddo et al., "Reduction of Soluble Abeta and Tau, but Not Soluble Abeta Alone, Ameliorates Cognitive Decline in Transgenic Mice with Plaques and Tangles," Journal of Biological Chemistry, vol. 281, No. 51, pp. 39413-39423 (2006).

Otvos et al., "Monoclonal Antibody PHF4 Recognizes Tau Protein Phosphorylated at Serine Residues 396 and 404," Journal of Neuroscience Research, vol. 39, pp. 669-673 (1994).

Ribe et al., "Accelerated Amyloid Deposition, Neurofibrillary Degeneration and Neuronal Loss in Double Mutant APP/TAU Transgenic Mice," Neurobiology of Disease, vol. 20, pp. 814-822 (2005).

Richter et al., "Doubly Phosphorylated Peptide Vaccines to Protect Transgenic P301S Mice against Alzheimer's Disease Like Tau Aggregation", Vaccines, vol. 2, pp. 601-623 (2014).

Ries et al., "Convenient synthesis and application of versatile nucleic acid lipid membrane anchors in the assembly and fusion of liposomes", Organic & Biomolecular Chemistry, vol. 13, pp. 9673-9680 (2015).

Roberson et al., "Reducing Endogenous Tau Ameliorates Amyloid (3-Induced Deficits in an Alzheimer's Disease Mouse Model," Science, vol. 316, pp. 750-754 (2007).

Roder et al., "Phosphorylation-Dependent Monoclonal Tau Antibodies Do Not Reliably Report Phosphorylation by Extracellular Signal-Regulated Kinase 2 at Specific Sites," Journal of Biological Chemistry, vol. 272, No. 7, pp. 4509-4515 (1997).

Roman et al., "Therapeutic Vaccination Using Cationic Liposome-Adjuvanted HIV Type 1 Peptides Representing HLA-Supertype-Restricted Subdominant T Cell Epitopes: Safety, Immunogenicity, and Feasibility in Guinea-Bissau," AIDS Research and Human Retroviruses, vol. 29, No. 11, pp. 1504-1512 (2013).

Rosenmann et al., "Tauopathy-Like Abnormalities and Neurologic Deficits in Mice Immunized with Neuronal Tau Protein," Arch Neurol, vol. 63, pp. 1459-1467 (2006).

(56) References Cited

OTHER PUBLICATIONS

Rueda et al., "Effect of TLR ligands co-encapsulated with multiepitopic antigen in nanoliposomes tartgeted to human DCs via Fc receptor for cancer vaccines," Immunobiology, vol. 222, pp. 989-997 (2017).
Sela et al., "Therapeutic Vaccines: Realities of Today and Hopes for the Future," Drug Discovery Today—Reviews, Therapeutic Focus, vol. 7, No. 12, pp. 664-673 (2002).
Singer et al., "Characterization of Phosphorylation Dependent Antibodies to Study the Phosphorylation Dependent Antibodies to Study the Phosphorylation Status of the Tau Protein," International Journal of Peptide Research and Therapeutics (formerly known as Letters in Pepdtide Science), vol. 11, No. 4, pp. 279-289 (2005).
Singer et al., "Immuno-PCR-Based Quantification of Multiple Phosphorylated Tau-Epitopes Linked to Alzheimer's Disease," Analytical and Bioanalytical Chemistry, vol. 395, No. 7, pp. 2263-2267 (2009).
Tabira, "Immunization Therapy for Alzheimer Disease: A Comprehensive Review of Active Immunization Strategies," Tohoku J. Exp. Med., vol. 220, pp. 95-106 (2010).
Terwel et al., "Amyloid Activates GSK-3p to Aggravate Neuronal Tauopathy in Bigenic Mice," The American Journal of Pathology, vol. 172, No. 3, pp. 786-798 (2008).
Theunis et al., "Efficacy and Safety of a Liposome-Based vaccine against Protein Tau, Assessed in Tau. P301 L Mice That Model Tauopathy," PLOS ONE, vol. 8, Issue 8, pp. e72301, 13 pages (2013).
Theunis et al., "Novel Phospho-Tau monoclonal Antibody Generated Using a Liposomal Vaccine, with Enhanced Recognition of Conformational Tauopathy Epitope", Journal of Alzheimer's Disease, vol. 56, No. 2, pp. 585-599 (2017).
Torreilles et al., "Binding Specificity of Monoclonal Antibody AD2: Influence of the Phosphorylation State of Tau," Molecular Brain Research, vol. 78, pp. 181-185 (2001).
Vanhelmont et al., "Serine-409 Phosphorylation and Oxidative Damage Define Aggregation of Human Protein Tau in Yeast," Fems Yeast Research, vol. 10, No. 8, pp. 992-1005 (2010).
Zemlan et al., "Monoclonal Antibody PHF-9 Recognizes Phosphorylated Serine 404 of Tau Protein and Labels Paired Helical Filaments," Journal of Neuroscience Research, vol. 46, No. 1, pp. 90-97 (1996).
Alving C R, "Antibodies to Liposomes Phospholipids and Phosphate Esters", Chemistry and Physics of Lipids, (1986), vol. 40, No. 2-4, doi:doi:10.1016/0009-3084(86)90075-7, ISSN 0009-3084, pp. 303-314, XP025418929.
Andronesi Ovidiu C et al, "Characterization of Alzheimer's-like paired helical filaments from the core domain of tau protein using solid-state NMR spectroscopy", Journal of the American Chemical Society, (2008), vol. 130, No. 18, ISSN 0002-7863, pp. 5922-5928.
Boutajangout Allal et al., "Immunotherapy Targeting Pathological Tau Prevents Cognitive Decline in a New Tangle Mouse Model", Journal of Neuroscience, (Dec. 2010), vol. 30, No. 49, doi:doi:10.1523/JNEUROSC1.4363-10.2010, ISSN 0270-6474, pp. 16559-16566, XP055203597.
Wassef N M et al, "Phosphate-Binding Specificities of Monoclonal Antibodies Against Phosphoinositides in Liposomes", Molecular Immunology, (1984), vol. 21, No. 10, doi:doi:10.1016/0161-5890(84)90140-8, ISSN 0161-5890, pp. 863-868, XP023786303.
Zheng-Fischhoefer et al., "Sequential Phosphorylation of Tau by Glycogen Synthase Kinase-3beta and Protein Kinase A at Thr212 and Ser214 Generates the Alzheimer-Specific Epitope of Antibody AT100 and Requires a Paired-Helical-Filament-Like Conformation," European Journal of Biochemistry, vol. 252, No. 3, pp. 542-552 (1998).
Shane Crotty, "Follicular helper CD4 T cells (TFH)", Annu. Rev. Immunol. 2011, 29, 621-663, www.annualreviews.org.
Greenberg et al., "A preparation of Alzheimer paired helical filaments that displays distinct T proteins by polyacrylamide gel electrophoresis", Proc. Natl. Acad. Sci. USA, vol. 87, pp. 5827-5831, Aug. 1990.
Peeraer et al., "Intracerebral injection of preformed synthetic tau fibrils initiates widespread tauopathy and neuronal loss in the brains of tau transgenic mice", Neurobiol. Dis. Jan. 2015, 73, 83-95.
Spensieri et al., "Human circulating influenza-CD4+ ICOS1+IL-21+ T cells expand after vaccination, exert helper function, and predict antibody responses", PNAS, vol. 110, No. 35, 14330-14335, Aug. 27, 2013.
Bentebibel et al., "Induction of ICOS+CXCR3+CXCR5+ TH cells correlates with antibody responses to influenza vaccination", Sci Transl Med Mar. 13, 2013, 5(176), 19 pages.
International Search Report and Written Opinion for App. No. PCT/US2020/029477, dated Aug. 14, 2020, 22 pages.
Sigurdsson, Einar M., "Tau Immunotherapy", Neurodegener Dis., 16(0), pp. 34-38, 2016.
Novak, Petr, et al., "Fundamant: an interventional 72-week phase 1 follow-up study of AADvac1, an active immunotherapy against tau protein pthology in Alzheimer's disease", Alzheimer's Research & Therapy, 10:108, 2018.
Dubois, Bruno, et al., "Preclinical Alzheimer's disease: Definition, natural history, and diagnostic criteria", Alzheimers Dement., 12(3), pp. 292-323, 2016.
Dubois, Bruno, et al., "Advancing research diagnostic criteria for Alzheimer's disease: the IWG-2 criteria", Lancet Neurol., 13, pp. 614-629, 2014.
Jack, Jr., Clifford R., et al., "NIA-AA Research Framework: Toward a biological definition of Alzheimer's disease", Alzheimer's & Dementia, 14, pp. 535-562, 2018.
Orgogozo, J.M., et al., "Subacute meningoencephalitis in a subset of patients with AD after AB42 immunization", Neurology, 61(1), pp. 46-54, 2003.
Novak, Petr, et al., "Ten Years of Tau-Targeted Immunotherapy: The Path Walked and the Roads Ahead", Front. Neurosci., 12, 798, 2018.
Rosenmann, Hanna, "Immunotherapy for Targeting Tau Pathology in Alzheimer's Disease and Tauopathier", Current Alzheimer Research, 10(3), pp. 217-228, 2013.
Davtyan, Hayk, et al., "MultiTEP platform-based AD epitope vaccine activates broad repertoire of T helper cells in non-human primates", Alzheimers Dement, vol. 10, issue 3 (May 2014) pp. 271-283.

* cited by examiner

SEQUENCE LISTING

```
<160> NUMBER OF SEQ ID NOS: 44

<210> SEQ ID NO 1
<211> LENGTH: 21
<212> TYPE: PRT
<213> ORGANISM: Artificial Sequence
<220> FEATURE:
<223> OTHER INFORMATION: phospho-tau peptide 7.1
<220> FEATURE:
<221> NAME/KEY: phosphorylated serine
<222> LOCATION: (8)..(8)
<220> FEATURE:
<221> NAME/KEY: phosphorylated serine
<222> LOCATION: (11)..(11)
<220> FEATURE:
<221> NAME/KEY: phosphorylated threonine
<222> LOCATION: (14)..(14)

<400> SEQUENCE: 1

Gly Asp Arg Ser Gly Tyr Ser Ser Pro Gly Ser Pro Gly Thr Pro Gly
1               5                   10                  15

Ser Arg Ser Arg Thr
            20

<210> SEQ ID NO 2
<211> LENGTH: 16
<212> TYPE: PRT
<213> ORGANISM: Artificial Sequence
<220> FEATURE:
```

```
<223> OTHER INFORMATION: phospho-tau peptide T3.5
<220> FEATURE:
<221> NAME/KEY: phosphorylated serine
<222> LOCATION: (4)..(4)
<220> FEATURE:
<221> NAME/KEY: phosphorylated serine
<222> LOCATION: (12)..(12)

<400> SEQUENCE: 2

Val Tyr Lys Ser Pro Val Val Ser Gly Asp Thr Ser Pro Arg His Leu
1               5                   10                  15

<210> SEQ ID NO 3
<211> LENGTH: 18
<212> TYPE: PRT
<213> ORGANISM: Artificial Sequence
<220> FEATURE:
<223> OTHER INFORMATION: phospho-tau peptide 22.1
<220> FEATURE:
<221> NAME/KEY: phosphorylated serine
<222> LOCATION: (11)..(11)
<220> FEATURE:
<221> NAME/KEY: phosphorylated threonine
<222> LOCATION: (16)..(16)

<400> SEQUENCE: 3

Ser Ser Thr Gly Ser Ile Asp Met Val Asp Ser Pro Gln Leu Ala Thr
1               5                   10                  15

Leu Ala

<210> SEQ ID NO 4
<211> LENGTH: 16
<212> TYPE: PRT
<213> ORGANISM: Artificial Sequence
<220> FEATURE:
<223> OTHER INFORMATION: tau peptide

<400> SEQUENCE: 4

Val Tyr Lys Ser Pro Val Val Ser Gly Asp Thr Ser Pro Arg His Leu
1               5                   10                  15

<210> SEQ ID NO 5
<211> LENGTH: 30
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (18)..(18)
<220> FEATURE:
<221> NAME/KEY: phosphorylated serine
<222> LOCATION: (26)..(26)

<400> SEQUENCE: 5

Arg Glu Asn Ala Lys Ala Lys Thr Asp His Gly Ala Glu Ile Val Tyr
1               5                   10                  15

Lys Ser Pro Val Val Ser Gly Asp Thr Ser Pro Arg His Leu
            20                  25                  30

<210> SEQ ID NO 6
<211> LENGTH: 16
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated tyrosine
<222> LOCATION: (14)..(14)
```

<400> SEQUENCE: 6

Arg Gln Glu Phe Glu Val Met Glu Asp His Ala Gly Thr Tyr Gly Leu
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated threonine
<222> LOCATION: (7)..(7)
<220> FEATURE:
<221> NAME/KEY: phosphorylated serine
<222> LOCATION: (9)..(9)

<400> SEQUENCE: 7

Pro Gly Ser Arg Ser Arg Thr Pro Ser Leu Pro Thr Pro Pro Thr Arg
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (7)..(7)
<220> FEATURE:
<221> NAME/KEY: phosphorylated threonine
<222> LOCATION: (10)..(10)

<400> SEQUENCE: 8

Gly Tyr Ser Ser Pro Gly Ser Pro Gly Thr Pro Gly Ser Arg Ser Arg
1               5                   10                  15

<210> SEQ ID NO 9
<211> LENGTH: 18
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (4)..(4)
<220> FEATURE:
<221> NAME/KEY: phosphorylated serine
<222> LOCATION: (9)..(9)

<400> SEQUENCE: 9

Gly Asp Thr Ser Pro Arg His Leu Ser Asn Val Ser Ser Thr Gly Ser
1               5                   10                  15

Ile Asp

<210> SEQ ID NO 10
<211> LENGTH: 17
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (3)..(3)
<220> FEATURE:
<221> NAME/KEY: phosphorylated threonine
<222> LOCATION: (6)..(6)
<220> FEATURE:

```
<221> NAME/KEY: phosphorylated threonine
<222> LOCATION: (13)..(13)
<220> FEATURE:
<221> NAME/KEY: phosphorylated serine
<222> LOCATION: (15)..(15)

<400> SEQUENCE: 10

Pro Gly Ser Pro Gly Thr Pro Gly Ser Arg Ser Arg Thr Pro Ser Leu
1               5                   10                  15

Pro

<210> SEQ ID NO 11
<211> LENGTH: 12
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (3)..(3)

<400> SEQUENCE: 11

His Leu Ser Asn Val Ser Ser Thr Gly Ser Ile Asp
1               5                   10

<210> SEQ ID NO 12
<211> LENGTH: 10
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (6)..(6)

<400> SEQUENCE: 12

Val Ser Gly Asp Thr Ser Pro Arg His Leu
1               5                   10

<210> SEQ ID NO 13
<211> LENGTH: 55
<212> TYPE: PRT
<213> ORGANISM: Artificial Sequence
<220> FEATURE:
<223> OTHER INFORMATION: T50 T cell epitope
<220> FEATURE:
<221> NAME/KEY: C-terminal amide
<222> LOCATION: (55)..(55)

<400> SEQUENCE: 13

Ala Lys Phe Val Ala Ala Trp Thr Leu Lys Ala Ala Val Val Arg
1               5                   10                  15

Gln Tyr Ile Lys Ala Asn Ser Lys Phe Ile Gly Ile Thr Glu Leu Val
                20                  25                  30

Val Arg Phe Asn Asn Phe Thr Val Ser Phe Trp Leu Arg Val Pro Lys
            35                  40                  45

Val Ser Ala Ser His Leu Glu
        50                  55

<210> SEQ ID NO 14
<211> LENGTH: 55
<212> TYPE: PRT
<213> ORGANISM: Artificial Sequence
<220> FEATURE:
<223> OTHER INFORMATION: T46 T cell epitope
<220> FEATURE:
<221> NAME/KEY: palmitoylated lysine
```

```
<222> LOCATION: (54)..(54)
<220> FEATURE:
<221> NAME/KEY: palmitoylated lysine
<222> LOCATION: (55)..(55)
<220> FEATURE:
<221> NAME/KEY: C-terminal amide
<222> LOCATION: (55)..(55)

<400> SEQUENCE: 14

Ala Lys Phe Val Ala Ala Trp Thr Leu Lys Ala Ala Gly Ser Gln
1               5                   10                  15

Tyr Ile Lys Ala Asn Ser Lys Phe Ile Gly Ile Thr Glu Leu Gly Ser
                20                  25                  30

Phe Asn Asn Phe Thr Val Ser Phe Trp Leu Arg Val Pro Lys Val Ser
            35                  40                  45

Ala Ser His Leu Glu Lys Lys
        50                  55

<210> SEQ ID NO 15
<211> LENGTH: 75
<212> TYPE: PRT
<213> ORGANISM: Artificial Sequence
<220> FEATURE:
<223> OTHER INFORMATION: T48 helper T cell epitope
<220> FEATURE:
<221> NAME/KEY: C-terminal amide
<222> LOCATION: (75)..(75)

<400> SEQUENCE: 15

Ala Lys Phe Val Ala Ala Trp Thr Leu Lys Ala Ala Gly Ser Gln
1               5                   10                  15

Tyr Ile Lys Ala Asn Ser Lys Phe Ile Gly Ile Thr Glu Leu Gly Ser
                20                  25                  30

Phe Asn Asn Phe Thr Val Ser Phe Trp Leu Arg Val Pro Lys Val Ser
            35                  40                  45

Ala Ser His Leu Glu Gly Ser Leu Ile Asn Ser Thr Lys Ile Tyr Ser
        50                  55                  60

Tyr Phe Pro Ser Val Ile Ser Lys Val Asn Gln
65                  70                  75

<210> SEQ ID NO 16
<211> LENGTH: 53
<212> TYPE: PRT
<213> ORGANISM: Artificial Sequence
<220> FEATURE:
<223> OTHER INFORMATION: T51 helper T cell epitope
<220> FEATURE:
<221> NAME/KEY: C-terminal amide
<222> LOCATION: (53)..(53)

<400> SEQUENCE: 16

Ala Lys Phe Val Ala Ala Trp Thr Leu Lys Ala Ala Arg Arg Gln
1               5                   10                  15

Tyr Ile Lys Ala Asn Ser Lys Phe Ile Gly Ile Thr Glu Leu Arg Arg
                20                  25                  30

Phe Asn Asn Phe Thr Val Ser Phe Trp Leu Arg Val Pro Lys Val Ser
            35                  40                  45

Ala Ser His Leu Glu
        50

<210> SEQ ID NO 17
<211> LENGTH: 53
<212> TYPE: PRT
```

```
<213> ORGANISM: Artificial Sequence
<220> FEATURE:
<223> OTHER INFORMATION: T52 helper T cell epitope
<220> FEATURE:
<221> NAME/KEY: C-terminal amide
<222> LOCATION: (53)..(53)

<400> SEQUENCE: 17

Ala Lys Phe Val Ala Ala Trp Thr Leu Lys Ala Ala Ala Arg Lys Gln
1               5                   10                  15

Tyr Ile Lys Ala Asn Ser Lys Phe Ile Gly Ile Thr Glu Leu Arg Lys
            20                  25                  30

Phe Asn Asn Phe Thr Val Ser Phe Trp Leu Arg Val Pro Lys Val Ser
        35                  40                  45

Ala Ser His Leu Glu
    50

<210> SEQ ID NO 18
<211> LENGTH: 24
<212> TYPE: DNA
<213> ORGANISM: Artificial Sequence
<220> FEATURE:
<223> OTHER INFORMATION: CpG 2006
<220> FEATURE:
<221> NAME/KEY: phosphorothioate (ps) internucleotide linkages
<222> LOCATION: (1)..(24)

<400> SEQUENCE: 18
tcgtcgtttt gtcgttttgt cgtt                                          24

<210> SEQ ID NO 19
<211> LENGTH: 22
<212> TYPE: DNA
<213> ORGANISM: Artificial Sequence
<220> FEATURE:
<223> OTHER INFORMATION: CpG 1018
<220> FEATURE:
<221> NAME/KEY: phosphorothioate (ps) internucleotide linkages
<222> LOCATION: (1)..(22)

<400> SEQUENCE: 19
tgactgtgaa cgttcgagat ga                                            22

<210> SEQ ID NO 20
<211> LENGTH: 22
<212> TYPE: DNA
<213> ORGANISM: Artificial Sequence
<220> FEATURE:
<223> OTHER INFORMATION: CpG 2395
<220> FEATURE:
<221> NAME/KEY: phosphorothioate (ps) internucleotide linkages
<222> LOCATION: (1)..(22)

<400> SEQUENCE: 20
tcgtcgtttt cggcgcgcgc cg                                            22

<210> SEQ ID NO 21
<211> LENGTH: 20
<212> TYPE: DNA
<213> ORGANISM: Artificial Sequence
<220> FEATURE:
<223> OTHER INFORMATION: CpG 2216
<220> FEATURE:
<221> NAME/KEY: phosphorothioate (ps) internucleotide linkages
<222> LOCATION: (1)..(3)
<220> FEATURE:
<221> NAME/KEY: phosphodiester (po) internucleotide linkages
<222> LOCATION: (3)..(14)
```

```
<220> FEATURE:
<221> NAME/KEY: phosphorothioate (ps) internucleotide linkages
<222> LOCATION: (14)..(20)

<400> SEQUENCE: 21
gggggacgat cgtcgggggg                                                    20

<210> SEQ ID NO 22
<211> LENGTH: 21
<212> TYPE: DNA
<213> ORGANISM: Artificial Sequence
<220> FEATURE:
<223> OTHER INFORMATION: CpG 2336
<220> FEATURE:
<221> NAME/KEY: phosphorothioate (ps) internucleotide linkages
<222> LOCATION: (1)..(4)
<220> FEATURE:
<221> NAME/KEY: phosphodiester (po) internucleotide linkages
<222> LOCATION: (4)..(15)
<220> FEATURE:
<221> NAME/KEY: phosphorothioate (ps) internucleotide linkages
<222> LOCATION: (15)..(21)

<400> SEQUENCE: 22
ggggacgacg tcgtgggggg g                                                  21

<210> SEQ ID NO 23
<211> LENGTH: 13
<212> TYPE: PRT
<213> ORGANISM: Artificial Sequence
<220> FEATURE:
<223> OTHER INFORMATION: Pan DR epitope (PADRE) peptide

<400> SEQUENCE: 23

Ala Lys Phe Val Ala Ala Trp Thr Leu Lys Ala Ala Ala
1               5                   10

<210> SEQ ID NO 24
<211> LENGTH: 15
<212> TYPE: PRT
<213> ORGANISM: Artificial Sequence
<220> FEATURE:
<223> OTHER INFORMATION: P2

<400> SEQUENCE: 24

Gln Tyr Ile Lys Ala Asn Ser Lys Phe Ile Gly Ile Thr Glu Leu
1               5                   10                  15

<210> SEQ ID NO 25
<211> LENGTH: 21
<212> TYPE: PRT
<213> ORGANISM: Artificial Sequence
<220> FEATURE:
<223> OTHER INFORMATION: P30

<400> SEQUENCE: 25

Phe Asn Asn Phe Thr Val Ser Phe Trp Leu Arg Val Pro Lys Val Ser
1               5                   10                  15

Ala Ser His Leu Glu
            20

<210> SEQ ID NO 26
<211> LENGTH: 20
<212> TYPE: PRT
<213> ORGANISM: Artificial Sequence
<220> FEATURE:
<223> OTHER INFORMATION: TT586-605
```

```
<400> SEQUENCE: 26

Leu Ile Asn Ser Thr Lys Ile Tyr Ser Tyr Phe Pro Ser Val Ile Ser
1               5                   10                  15

Lys Val Asn Gln
            20

<210> SEQ ID NO 27
<211> LENGTH: 25
<212> TYPE: PRT
<213> ORGANISM: Artificial Sequence
<220> FEATURE:
<223> OTHER INFORMATION: palmitoylated phospho-tau peptide
      (palmitoylated 7.1)
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (10)..(10)
<220> FEATURE:
<221> NAME/KEY: phosphorylated serine
<222> LOCATION: (13)..(13)
<220> FEATURE:
<221> NAME/KEY: phosphorylated threonine
<222> LOCATION: (16)..(16)
<220> FEATURE:
<221> NAME/KEY: palmitoylated lysine
<222> LOCATION: (24)..(24)
<220> FEATURE:
<221> NAME/KEY: palmitoylated lysine
<222> LOCATION: (25)..(25)

<400> SEQUENCE: 27

Lys Lys Gly Asp Arg Ser Gly Tyr Ser Ser Pro Gly Ser Pro Gly Thr
1               5                   10                  15

Pro Gly Ser Arg Ser Arg Thr Lys Lys
            20                  25

<210> SEQ ID NO 28
<211> LENGTH: 20
<212> TYPE: PRT
<213> ORGANISM: Artificial Sequence
<220> FEATURE:
<223> OTHER INFORMATION: palmitoylated phospho-tau peptide (T3,
      palmitoylated T3.5)
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (6)..(6)
<220> FEATURE:
<221> NAME/KEY: phosphorylated serine
<222> LOCATION: (14)..(14)
<220> FEATURE:
<221> NAME/KEY: palmitoylated lysine
<222> LOCATION: (19)..(19)
<220> FEATURE:
<221> NAME/KEY: palmitoylated lysine
<222> LOCATION: (20)..(20)

<400> SEQUENCE: 28

Lys Lys Val Tyr Lys Ser Pro Val Val Ser Gly Asp Thr Ser Pro Arg
1               5                   10                  15

His Leu Lys Lys
```

<210> SEQ ID NO 29
<211> LENGTH: 22
<212> TYPE: PRT
<213> ORGANISM: Artificial Sequence
<220> FEATURE:
<223> OTHER INFORMATION: palmitoylated phospho-tau peptide
      (palmitoylated 22.1)
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (13)..(13)
<220> FEATURE:
<221> NAME/KEY: phosphorylated threonine
<222> LOCATION: (18)..(18)
<220> FEATURE:
<221> NAME/KEY: palmitoylated lysine
<222> LOCATION: (21)..(21)
<220> FEATURE:
<221> NAME/KEY: palmitoylated lysine
<222> LOCATION: (22)..(22)

<400> SEQUENCE: 29

Lys Lys Ser Ser Thr Gly Ser Ile Asp Met Val Asp Ser Pro Gln Leu
1               5                   10                  15

Ala Thr Leu Ala Lys Lys
            20

<210> SEQ ID NO 30
<211> LENGTH: 20
<212> TYPE: PRT
<213> ORGANISM: Artificial Sequence
<220> FEATURE:
<223> OTHER INFORMATION: palmitoylated tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: palmitoylated lysine
<222> LOCATION: (19)..(19)
<220> FEATURE:
<221> NAME/KEY: palmitoylated lysine
<222> LOCATION: (20)..(20)

<400> SEQUENCE: 30

Lys Lys Val Tyr Lys Ser Pro Val Val Ser Gly Asp Thr Ser Pro Arg
1               5                   10                  15

His Leu Lys Lys
            20

<210> SEQ ID NO 31
<211> LENGTH: 34
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:

```
<221> NAME/KEY: phosphorylated serine
<222> LOCATION: (20)..(20)
<220> FEATURE:
<221> NAME/KEY: phosphorylated serine
<222> LOCATION: (28)..(28)
<220> FEATURE:
<221> NAME/KEY: palmitoylated lysine
<222> LOCATION: (33)..(33)
<220> FEATURE:
<221> NAME/KEY: palmitoylated lysine
<222> LOCATION: (34)..(34)

<400> SEQUENCE: 31

Lys Lys Arg Glu Asn Ala Lys Ala Lys Thr Asp His Gly Ala Glu Ile
1               5                   10                  15

Val Tyr Lys Ser Pro Val Val Ser Gly Asp Thr Ser Pro Arg His Leu
            20                  25                  30

Lys Lys

<210> SEQ ID NO 32
<211> LENGTH: 20
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated tyrosine
<222> LOCATION: (16)..(16)
<220> FEATURE:
<221> NAME/KEY: palmitoylated lysine
<222> LOCATION: (19)..(19)
<220> FEATURE:
<221> NAME/KEY: palmitoylated lysine
<222> LOCATION: (20)..(20)

<400> SEQUENCE: 32

Lys Lys Arg Gln Glu Phe Glu Val Met Glu Asp His Ala Gly Thr Tyr
1               5                   10                  15

Gly Leu Lys Lys
            20

<210> SEQ ID NO 33
<211> LENGTH: 20
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated threonine
<222> LOCATION: (9)..(9)
<220> FEATURE:
<221> NAME/KEY: phosphorylated serine
<222> LOCATION: (11)..(11)
<220> FEATURE:
<221> NAME/KEY: palmitoylated lysine
<222> LOCATION: (19)..(19)
<220> FEATURE:
<221> NAME/KEY: palmitoylated lysine
<222> LOCATION: (20)..(20)
```

-continued

```
<400> SEQUENCE: 33

Lys Lys Pro Gly Ser Arg Ser Arg Thr Pro Ser Leu Pro Thr Pro Pro
1               5                   10                  15

Thr Arg Lys Lys
            20

<210> SEQ ID NO 34
<211> LENGTH: 20
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (9)..(9)
<220> FEATURE:
<221> NAME/KEY: phosphorylated threonine
<222> LOCATION: (12)..(12)
<220> FEATURE:
<221> NAME/KEY: palmitoylated lysine
<222> LOCATION: (19)..(19)
<220> FEATURE:
<221> NAME/KEY: palmitoylated lysine
<222> LOCATION: (20)..(20)

<400> SEQUENCE: 34

Lys Lys Gly Tyr Ser Ser Pro Gly Ser Pro Gly Thr Pro Gly Ser Arg
1               5                   10                  15

Ser Arg Lys Lys
            20

<210> SEQ ID NO 35
<211> LENGTH: 22
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (6)..(6)
<220> FEATURE:
<221> NAME/KEY: phosphorylated serine
<222> LOCATION: (11)..(11)
<220> FEATURE:
<221> NAME/KEY: palmitoylated lysine
<222> LOCATION: (21)..(21)
<220> FEATURE:
<221> NAME/KEY: palmitoylated lysine
<222> LOCATION: (22)..(22)

<400> SEQUENCE: 35

Lys Lys Gly Asp Thr Ser Pro Arg His Leu Ser Asn Val Ser Ser Thr
1               5                   10                  15

Gly Ser Ile Asp Lys Lys
            20

<210> SEQ ID NO 36
<211> LENGTH: 21
```

```
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (5)..(5)
<220> FEATURE:
<221> NAME/KEY: phosphorylated threonine
<222> LOCATION: (8)..(8)
<220> FEATURE:
<221> NAME/KEY: phosphorylated threonine
<222> LOCATION: (15)..(15)
<220> FEATURE:
<221> NAME/KEY: phosphorylated serine
<222> LOCATION: (17)..(17)
<220> FEATURE:
<221> NAME/KEY: palmitoylated lysine
<222> LOCATION: (20)..(20)
<220> FEATURE:
<221> NAME/KEY: palmitoylated lysine
<222> LOCATION: (21)..(21)

<400> SEQUENCE: 36

Lys Lys Pro Gly Ser Pro Gly Thr Pro Gly Ser Arg Ser Arg Thr Pro
1               5                   10                  15

Ser Leu Pro Lys Lys
            20

<210> SEQ ID NO 37
<211> LENGTH: 16
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (5)..(5)
<220> FEATURE:
<221> NAME/KEY: palmitoylated lysine
<222> LOCATION: (15)..(15)
<220> FEATURE:
<221> NAME/KEY: palmitoylated lysine
<222> LOCATION: (16)..(16)

<400> SEQUENCE: 37

Lys Lys His Leu Ser Asn Val Ser Ser Thr Gly Ser Ile Asp Lys Lys
1               5                   10                  15

<210> SEQ ID NO 38
<211> LENGTH: 14
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
```

```
<221> NAME/KEY: phosphorylated serine
<222> LOCATION: (8)..(8)
<220> FEATURE:
<221> NAME/KEY: palmitoylated lysine
<222> LOCATION: (13)..(13)
<220> FEATURE:
<221> NAME/KEY: palmitoylated lysine
<222> LOCATION: (14)..(14)

<400> SEQUENCE: 38

Lys Lys Val Ser Gly Asp Thr Ser Pro Arg His Leu Lys Lys
1               5                   10

<210> SEQ ID NO 39
<211> LENGTH: 55
<212> TYPE: PRT
<213> ORGANISM: Artificial Sequence
<220> FEATURE:
<223> OTHER INFORMATION: T50 without the C-terminal amide

<400> SEQUENCE: 39

Ala Lys Phe Val Ala Ala Trp Thr Leu Lys Ala Ala Ala Val Val Arg
1               5                   10                  15

Gln Tyr Ile Lys Ala Asn Ser Lys Phe Ile Gly Ile Thr Glu Leu Val
            20                  25                  30

Val Arg Phe Asn Asn Phe Thr Val Ser Phe Trp Leu Arg Val Pro Lys
        35                  40                  45

Val Ser Ala Ser His Leu Glu
    50                  55

<210> SEQ ID NO 40
<211> LENGTH: 53
<212> TYPE: PRT
<213> ORGANISM: Artificial Sequence
<220> FEATURE:
<223> OTHER INFORMATION: T46 without the palmitoylated lysines and
      C-terminal amide

<400> SEQUENCE: 40

Ala Lys Phe Val Ala Ala Trp Thr Leu Lys Ala Ala Ala Gly Ser Gln
1               5                   10                  15

Tyr Ile Lys Ala Asn Ser Lys Phe Ile Gly Ile Thr Glu Leu Gly Ser
            20                  25                  30

Phe Asn Asn Phe Thr Val Ser Phe Trp Leu Arg Val Pro Lys Val Ser
        35                  40                  45

Ala Ser His Leu Glu
    50

<210> SEQ ID NO 41
<211> LENGTH: 75
<212> TYPE: PRT
<213> ORGANISM: Artificial Sequence
<220> FEATURE:
<223> OTHER INFORMATION: T48 without the C-terminal amide

<400> SEQUENCE: 41

Ala Lys Phe Val Ala Ala Trp Thr Leu Lys Ala Ala Ala Gly Ser Gln
1               5                   10                  15

Tyr Ile Lys Ala Asn Ser Lys Phe Ile Gly Ile Thr Glu Leu Gly Ser
            20                  25                  30

Phe Asn Asn Phe Thr Val Ser Phe Trp Leu Arg Val Pro Lys Val Ser
        35                  40                  45

Ala Ser His Leu Glu Gly Ser Leu Ile Asn Ser Thr Lys Ile Tyr Ser
```

```
                    50                  55                  60
Tyr Phe Pro Ser Val Ile Ser Lys Val Asn Gln
65                  70                  75

<210> SEQ ID NO 42
<211> LENGTH: 53
<212> TYPE: PRT
<213> ORGANISM: Artificial Sequence
<220> FEATURE:
<223> OTHER INFORMATION: T51 without the C-terminal amide

<400> SEQUENCE: 42

Ala Lys Phe Val Ala Ala Trp Thr Leu Lys Ala Ala Ala Arg Arg Gln
1               5                   10                  15

Tyr Ile Lys Ala Asn Ser Lys Phe Ile Gly Ile Thr Glu Leu Arg Arg
                20                  25                  30

Phe Asn Asn Phe Thr Val Ser Phe Trp Leu Arg Val Pro Lys Val Ser
            35                  40                  45

Ala Ser His Leu Glu
        50

<210> SEQ ID NO 43
<211> LENGTH: 53
<212> TYPE: PRT
<213> ORGANISM: Artificial Sequence
<220> FEATURE:
<223> OTHER INFORMATION: T52 without the C-terminal amide

<400> SEQUENCE: 43

Ala Lys Phe Val Ala Ala Trp Thr Leu Lys Ala Ala Ala Arg Lys Gln
1               5                   10                  15

Tyr Ile Lys Ala Asn Ser Lys Phe Ile Gly Ile Thr Glu Leu Arg Lys
                20                  25                  30

Phe Asn Asn Phe Thr Val Ser Phe Trp Leu Arg Val Pro Lys Val Ser
            35                  40                  45

Ala Ser His Leu Glu
        50

<210> SEQ ID NO 44
<211> LENGTH: 57
<212> TYPE: PRT
<213> ORGANISM: Artificial Sequence
<220> FEATURE:
<223> OTHER INFORMATION: T57
<220> FEATURE:
<221> NAME/KEY: palmitoylated lysine
<222> LOCATION: (56)..(56)
<220> FEATURE:
<221> NAME/KEY: palmitoylated lysine
<222> LOCATION: (57)..(57)
<220> FEATURE:
<221> NAME/KEY: C-terminal amide
<222> LOCATION: (57)..(57)

<400> SEQUENCE: 44

Ala Lys Phe Val Ala Ala Trp Thr Leu Lys Ala Ala Ala Val Val Arg
1               5                   10                  15

Gln Tyr Ile Lys Ala Asn Ser Lys Phe Ile Gly Ile Thr Glu Leu Val
                20                  25                  30
```

-continued

```
Val Arg Phe Asn Asn Phe Thr Val Ser Phe Trp Leu Arg Val Pro Lys
        35                  40                  45
Val Ser Ala Ser His Leu Glu Lys Lys
 50              55
```

HETEROLOGOUS ADMINISTRATION OF TAU VACCINES

CROSS-REFERENCE TO RELATED APPLICATIONS

This application claims the benefit of priority to U.S. Provisional Patent Application No. 62/837,987, filed on Apr. 24, 2019. The disclosure of the aforementioned application is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence_Listing_065794_4US3" and a creation date of Apr. 23, 2020, and having a size of 23 KB. The sequence listing submitted via EFS-Web is part of the specification and is herein incorporated by reference in its entirety.

FIELD OF THE INVENTION

The present invention is in the field of medicine. The invention in particular relates to methods for inducing an immune response against tau protein in a subject suffering from a neurodegenerative disease, disorder or condition with a liposomal priming composition containing a tau peptide and a conjugate boosting composition comprising a tau peptide conjugated to an immunogenic carrier.

BACKGROUND

Alzheimer's disease (AD) is a progressive debilitating neurodegenerative disease that affects an estimated 44 million people worldwide (Alzheimers.net). AD therapies that are currently available in the clinic aim to slow the progression of clinical symptoms, but do not target the pathogenic processes that underlie the disease. Unfortunately, these therapies are only minimally efficacious, and there is therefore an urgent need to develop and test additional preventive and therapeutic measures.

The hallmark pathologies for Alzheimer's disease are an accumulation of extracellular plaques comprising aggregated amyloid beta protein and intracellular "tangles" or aggregations of hyperphosphorylated tau protein. The molecular events that lead to accumulation of these proteins are poorly characterized. For amyloid, it is hypothesized that aberrant cleavage of the amyloid precursor protein leads to an accumulation of the aggregation-prone fragment comprising amino acids 1-42. For tau, it is hypothesized that dysregulation of either kinases, phosphatases, or both, leads to aberrant phosphorylation of tau. Once tau becomes hyperphosphorylated it loses the ability to effectively bind and stabilize microtubules, and instead accumulates in the cytoplasm of the affected neuron. The unbound and hyperphosphorylated tau appears to form first oligomers and then higher order aggregates, the presence of which presumably negatively affects function of the neuron in which they form, perhaps via interruption of normal axonal transport.

In developed nations, individuals diagnosed with Alzheimer's disease or other dementing tauopathies are commonly treated with cholinesterase inhibitors (e.g. Aricept®) or memantines (e.g. Namenda™). These drugs, although reasonably well tolerated, have very modest efficacy. For example, Aricept® delays the worsening of symptoms for 6-12 months in approximately 50% of treated individuals. The remainder of treatment is non-pharmacologic, and focuses on making patients more capable of managing day to day tasks as their cognitive ability declines.

Several published studies (Asuni A A et al., J Neurosci. 2007 Aug. 22; 27(34):9115-29., Theunis C et al., PLoS One. 2013; 8(8): e72301, Kontsekova E et al., Alzheimers Res Ther. 2014 Aug. 1; 6(4):44) demonstrate that active vaccines containing tau peptides can induce anti-tau immune responses in mice or rats; reduce the accumulation of pathologic tau aggregates in the brain of rodents; and reduce the rate of progression of cognitive decline in animal models of Alzheimer's disease. An active vaccine against pathological tau proteins was shown to be immunogenic in human patients with Alzheimer's disease (Novak P et al., Lancet Neurology 2017, 16:123-134). WO2010/115843 and WO2019/084118 describe antigenic phosphopeptide mimicking a major pathological phospho-epitope of protein tau and related compositions for the therapeutic and diagnostic use in the treatment of tauopathies including Alzheimer's Disease. However, at present there are still no approved efficacious vaccines on the market to prevent the onset of tau-mediated disease. Neither are there efficacious drugs on the market to intercept or slow the course of disease once it begins. There is therefore a pressing need to identify new preventative measures (e.g. vaccines) that can prevent these diseases.

SUMMARY OF THE INVENTION

It was surprisingly discovered in the present invention that heterologous vaccination with a liposome composition and a conjugate composition, each of which comprises a tau phosphopeptide, has increased the epitope coverage of tau phosphopeptide-specific antibodies. Additionally, it was found that a heterologous vaccination with a liposome priming composition has induced a stronger immune response than that with a conjugate priming composition.

In one general aspect, the invention relates to a method for inducing an immune response against a tau protein, preferably inducing antibodies against at least one of phosphorylated Tau and enriched paired helical filaments (ePHFs), in a subject in need thereof, preferably a subject suffering from a neurodegenerative disorder, the method comprising:

(i) administering to the subject a priming composition comprising an immunologically effective amount of a liposome comprising:

a. a first tau phosphopeptide;

b. a helper T-cell epitope;

c. a lipidated CpG oligonucleotide; and d. an adjuvant containing a toll-like receptor 4 ligand;

wherein the tau phosphopeptide is presented on the surface of the liposome, and the priming composition further comprises a pharmaceutically acceptable carrier; and (ii) administering to the subject a first boosting composition comprising an immunologically effective amount of a conjugate comprising a second tau phosphopeptide and an immunogenic carrier conjugated thereto via a linker, the conjugate having the structure of formula (I):

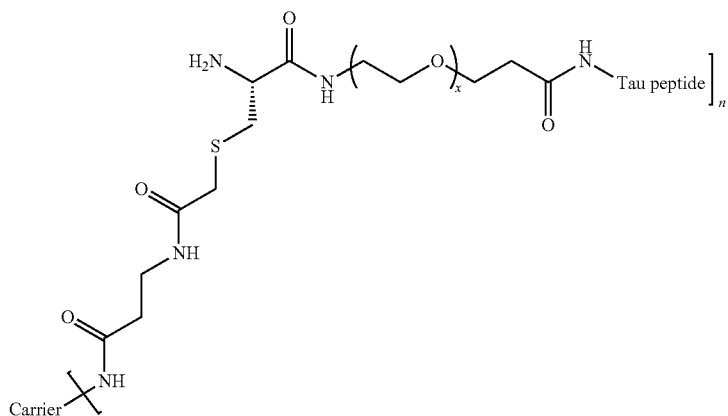

or having the structure of formula (II):

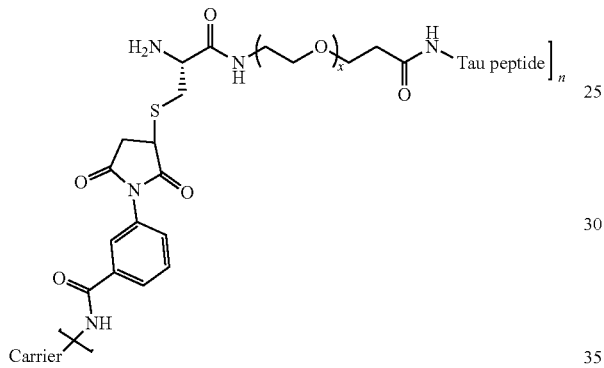

wherein
x is an integer of 0 to 10, preferably 2 to 6, most preferably 3;
n is an integer of 3 to 15, preferably 3 to 12;
Tau peptide represents the second tau phosphopeptide; and
Carrier represents the immunogenic carrier selected from the group consisting of keyhole limpet hemocyanin (KLH), tetanus toxoid, CRM197 and an outer membrane protein mixture from *N. meningitidis* (OMP), or a derivative thereof; and
the first boosting composition further comprises a pharmaceutically acceptable carrier;

wherein the first tau phosphopeptide and the second tau phosphopeptide each independently comprises an amino acid sequence selected from the group consisting of SEQ ID NO: 1 to SEQ ID NO: 3 and SEQ ID NO: 5 to SEQ ID NO: 12.

In certain embodiments, the liposome comprises:
a. the first tau phosphopeptide having an amino acid sequence selected from the group consisting of SEQ ID NO: 27 to SEQ ID NO: 29 and SEQ ID NO: 31 to SEQ ID NO: 38;
b. the helper T cell epitope having an amino acid sequence selected from the group consisting of SEQ ID NO: 39 to SEQ ID NO: 44, preferably, the helper T cell epitope consisting of an amino acid sequence selected from the group consisting of SEQ ID NO: 13 to SEQ ID NO: 17;
c. the lipidated CpG oligonucleotide having a nucleotide sequence selected from the group consisting of SEQ ID NO: 18 to SEQ ID NO: 22, wherein the CpG oligonucleotide comprises one or more phosphorothioate internucleotide linkages, and the CpG oligonucleotide is covalently linked to at least one cholesterol via a linker; and
d. monophosphoryl lipid A (MPLA); and
the conjugate comprises the second tau phosphopeptide having an amino acid sequence selected from the group consisting of SEQ ID NO: 27 to SEQ ID NO: 29 and SEQ ID NO: 31 to SEQ ID NO: 38 conjugated to CRM197 via the linker.

In certain embodiments, the conjugate has the structure of:

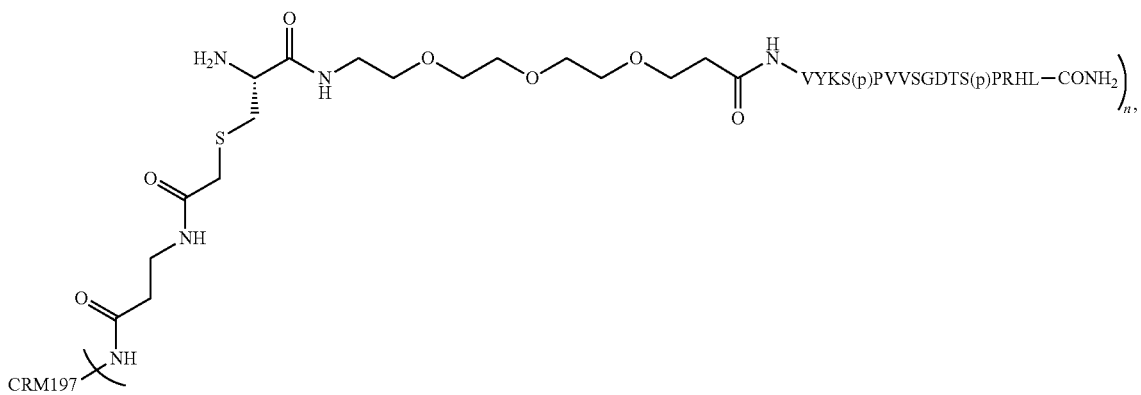

wherein n is an integer of 3 to 7 and VYKS(p)PVVSGDTS(p)PRHL-CONH₂ comprises the phospho-tau peptide of SEQ ID NO:2.

According to an embodiment of the invention, a method for inducing antibodies against at least one of phosphorylated Tau and enriched paired helical filaments (ePHFs) in a subject in need thereof, comprises:

(i) administering to the subject a priming composition comprising an immunologically effective amount of a liposome comprising:
  a. a first tau phosphopeptide having an amino acid sequence selected from the group consisting of SEQ ID NO: 27 to SEQ ID NO: 29 and SEQ ID NO: 31 to SEQ ID NO: 38;
  b. a helper T cell epitope having an amino acid sequence selected from the group consisting of SEQ ID NO: 39 to SEQ ID NO: 44, preferably, the helper T cell epitope consisting of an amino acid sequence selected from the group consisting of SEQ ID NO: 13 to SEQ ID NO: 17;
  c. a lipidated CpG oligonucleotide having a nucleotide sequence selected from the group consisting of SEQ ID NO: 18 to SEQ ID NO: 22, wherein the CpG oligonucleotide comprises one or more phosphorothioate internucleotide linkages, and the CpG oligonucleotide is covalently linked to at least one cholesterol via a linker; and
  d. monophosphoryl lipid A (MPLA);
wherein the first tau phosphopeptide is presented on the surface of the liposome, and the priming composition further comprises a pharmaceutically acceptable carrier; and (ii) administering to the subject a first boosting composition comprising an immunologically effective amount of a conjugate comprising a second tau phosphopeptide and an immunogenic carrier conjugated thereto via a linker, the conjugate having the structure of:

wherein n is an integer of 3 to 7 and VYKS(p)PVVSGDTS(p)PRHL-CONH₂ comprises the phospho-tau peptide of SEQ ID NO:2, and wherein the first boosting composition further comprises a pharmaceutically acceptable carrier.

According to another embodiment of the application, a method for inducing antibodies against at least one of phosphorylated Tau and enriched paired helical filaments (ePHFs) in a subject in need thereof, comprises:

(i) administering to the subject a priming composition comprising an immunologically effective amount of a liposome comprising:
  (1) a first tau phosphopeptide having the amino acid sequence of SEQ ID NO:28;
  (2) a toll-like receptor 4 agonist comprising monophosphoryl hexa-acyl Lipid A, 3-deacyl;
  (3) a helper T-cell epitope comprising the amino acid sequence of SEQ ID NO: 39;
  (4) a lipidated CpG oligonucleotide comprising the nucleotide sequence of SEQ ID NO:18; and
  (5) at least one lipid selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol,
wherein the first tau phosphopeptide is presented on the surface of the liposome, and the priming composition further comprises a pharmaceutically acceptable carrier; and (ii) administering to the subject a first boosting composition comprising an immunologically effective amount of a conjugate comprising a second tau phosphopeptide and an immunogenic carrier conjugated thereto via a linker, the conjugate having the structure of:

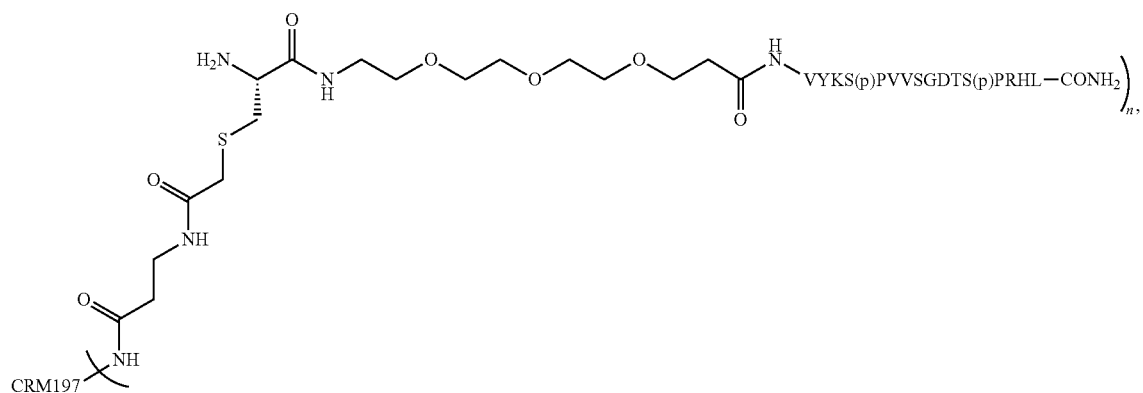

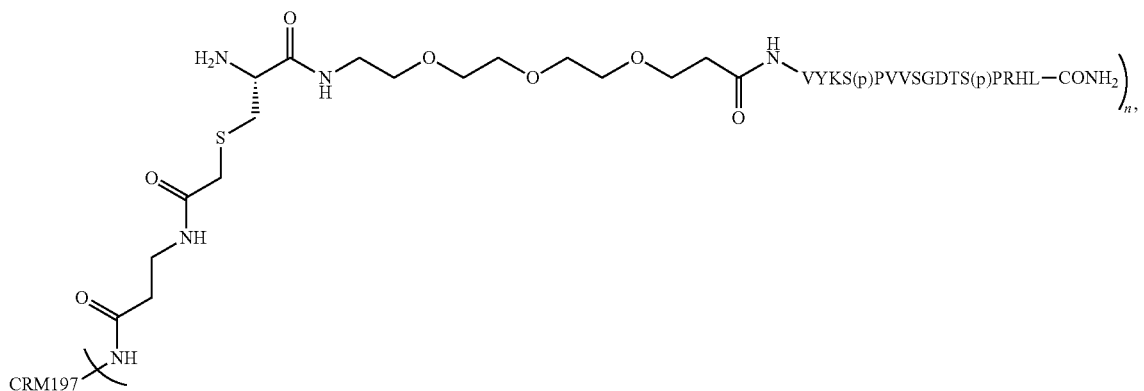

wherein n is an integer of 3 to 7 and VYKS(p)PVVSGDTS(p)PRHL-CONH$_2$ comprises the phospho-tau peptide of SEQ ID NO:2, and wherein the first boosting composition further comprises a pharmaceutically acceptable carrier.

In certain embodiments, the method further comprises administering the first boosting composition to the subject at least once after the initial administration of the first boosting composition.

In certain embodiments, the method further comprises administering to the subject a second boosting composition comprising an immunologically effective amount of the liposome and a pharmaceutically acceptable carrier. The second boosting composition can be administered before or after the initial administration of the first boosting composition.

In certain embodiments, the method further comprises administering the second boosting composition to the subject at least once after the initial administration of the second boosting composition.

According to an embodiment of the application, a method for inducing antibodies against at least one of phosphorylated Tau and enriched paired helical filaments (ePHFs) in a subject in need thereof, comprises:
(i) administering to the subject a priming composition comprising an immunologically effective amount of a liposome comprising:
(1) a first tau phosphopeptide having the amino acid sequence of SEQ ID NO:28;
(2) a toll-like receptor 4 agonist comprising monophosphoryl hexa-acyl Lipid A, 3-deacyl;
(3) a helper T-cell epitope comprising the amino acid sequence of SEQ ID NO: 39;
(4) a lipidated CpG oligonucleotide comprising the nucleotide sequence of SEQ ID NO:18; and
(5) at least one lipid selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol, wherein the first tau phosphopeptide is presented on the surface of the liposome, and the priming composition further comprises a pharmaceutically acceptable carrier;

(ii) administering to the subject a first boosting composition comprising an immunologically effective amount of a conjugate comprising a second tau phosphopeptide and an immunogenic carrier conjugated thereto via a linker, the conjugate having the structure of:

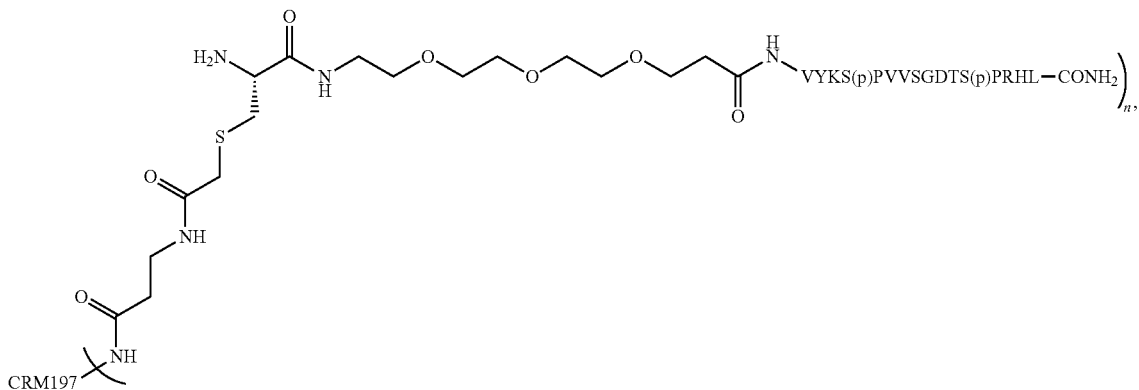

wherein n is an integer of 3 to 7 and VYKS(p)PVVSGDTS(p)PRHL-CONH$_2$ comprises the phospho-tau peptide of SEQ ID NO:2, and wherein the first boosting composition further comprises a pharmaceutically acceptable carrier; and (iii) administering to the subject the first boosting composition or a second boosting composition comprising an immunologically effective amount of the liposome and a pharmaceutically acceptable carrier.

In certain embodiments, step (ii) is conducted before step (iii).

In other embodiments, step (ii) is conducted after step (iii).

In certain embodiments, the method comprises administering to the subject the first boosting composition at least twice for boosting an immune response.

In certain embodiments, the method comprises administering to the subject the second boosting composition at least once for boosting an immune response.

In certain embodiments, the first boosting composition is administered at about 27-32 days after the priming composition is administered. Preferably, the method further comprises re-administering the first boosting composition at about 82-87 days after the priming composition is initially administered, and optionally further comprises administering the second boosting composition at about 167-172 days after the priming composition is administered.

In certain embodiments, the first boosting composition is administered at about 82-87 days after the priming composition is administered. Preferably, the method further comprises administering the second boosting composition at about 27-32 days after the priming composition is administered, and optionally further comprises re-administering the first boosting composition at about 167-172 days after the priming composition is administered.

In certain embodiments, the immunologically effective amount of the liposome contains about 25 nmoles to about 750 nmoles per dose of the first Tau phosphopeptide, such as about 29.7 nmoles to about 742.5 nmoles per dose, preferably about 90 nmoles to about 715 nmoles, such as about 89.1 nmoles to about 712.8 nmoles per dose, or about 90 nmoles to about 535 nmoles per dose, such as about 89.1 nmoles to about 534.6 nmoles per dose, or about 90 nmoles to about 275 nmoles per dose, such as about 89.1 nmoles to about 267.3 nmoles per dose of the first Tau phosphopeptide, and the first Tau phosphopeptide is presented on the surface of the liposome. In one embodiment, the effective amount of liposomes comprises the first Tau phosphopeptide at an amount of about 265 to about 275 nmoles per dose, e.g., about 265, about 266, about 267, about 268, about 269, about 270, about 271, about 272, about 273, about 274 or about 275 nmoles per dose, or any value in between, such as about 267.3 nmoles per dose. In another embodiment, the immunologically effective amount of the liposome contains the first Tau phosphopeptide at an amount of about 530 to about 540 nmoles per dose, such as about 530, about 531, about 532, about 533, about 534, about 535, about 536, about 537, about 538, about 539 or about 540 nmoles per dose, or any value in between, such as about 534.6 nmoles per dose. In another embodiment, the effective amount of liposomes comprises the first Tau phosphopeptide at an amount of about 710 to about 720 nmoles per dose, such as about 710, about 711, about 712, about 713, about 714, about 715, about 716, about 717, about 718, about 719 or about 720 nmoles per dose, or any value in between, such as about 712.8 nmoles per dose.

In certain embodiments, the first Tau phosphopeptide consists of an amino acid sequence selected from the group consisting of SEQ ID NO:27 to SEQ ID NO:29 and SEQ ID NO:31 to SEQ ID NO:38, preferably consists of an amino acid sequence of SEQ ID NO:28. In one embodiment, the immunologically effective amount of the liposome contains a tetrapalmitoylated Tau phosphopeptide consisting of the amino acid sequence of SEQ ID NO: 28, wherein the tetrapalmitoylated Tau phosphopeptide is presented on the surface of the liposome and is administered at an amount of about 100 µg to about 2500 µg per dose, corresponding to about 29.7 nmoles to about 742.5 nmoles per dose, preferably about 300 µg to about 2400 µg per dose, corresponding to about 89.1 nmoles to about 712.8 nmols per dose, such as about 300 µg, about 900 µg, about 1800 µg or about 2400 µg per dose, corresponding to about 89.1 nmoles, about 267.3 nmoles, about 534.6 nmoles or about 712.8 nmoles per dose.

In certain embodiments, the immunologically effective amount of the liposome comprises a helper T-cell epitope at an amount of about 2 nmoles to about 110 nmoles per dose, such as about 4.02 nmoles to about 100.44 nmoles per dose, or about 4 nmoles to about 75 nmoles per dose, such as about 4.02 nmoles to about 72.32 nmoles per dose, or about 10 nmoles to about 105 nmoles per dose, such as about 12.06 nmoles to about 100.44 nmoles per dose, or about 70 to about 105 nmoles per dose, such as about 72.32 nmoles to about 100.44 nmoles per dose. In certain embodiments, the effective amount of liposomes comprises a helper T-cell epitope that is preferably a T50 helper T-cell epitope consisting of the amino acid sequence of SEQ ID NO: 13 at an amount of about 2 nmoles to about 110 nmoles, such as about 12.06 nmoles to about 100.44 nmoles.

The invention also relates to a vaccine combination, such as a kit, of the liposomes and conjugates of the invention for use in inducing an immune response against a tau protein in a subject suffering from a neurodegenerative disorder, or for use in treating or preventing a neurodegenerative disease or disorder in a subject in need thereof.

The invention also relates to use of a vaccine combination of the liposomes and conjugates of the invention in the manufacture of a medicament for inducing an immune response against a tau protein in a subject suffering from a neurodegenerative disorder, or for treating or preventing a neurodegenerative disease or disorder in a subject in need thereof.

Further aspects, features and advantages of the present invention will be better appreciated upon a reading of the following detailed description of the invention and claims.

BRIEF DESCRIPTION OF THE FIGURES

The foregoing summary, as well as the following detailed description of preferred embodiments of the present application, will be better understood when read in conjunction with the appended drawings. It should be understood, however, that the application is not limited to the precise embodiments shown in the drawings.

DETAILED DESCRIPTION OF THE INVENTION

Figures 1A, 1B, 1C:
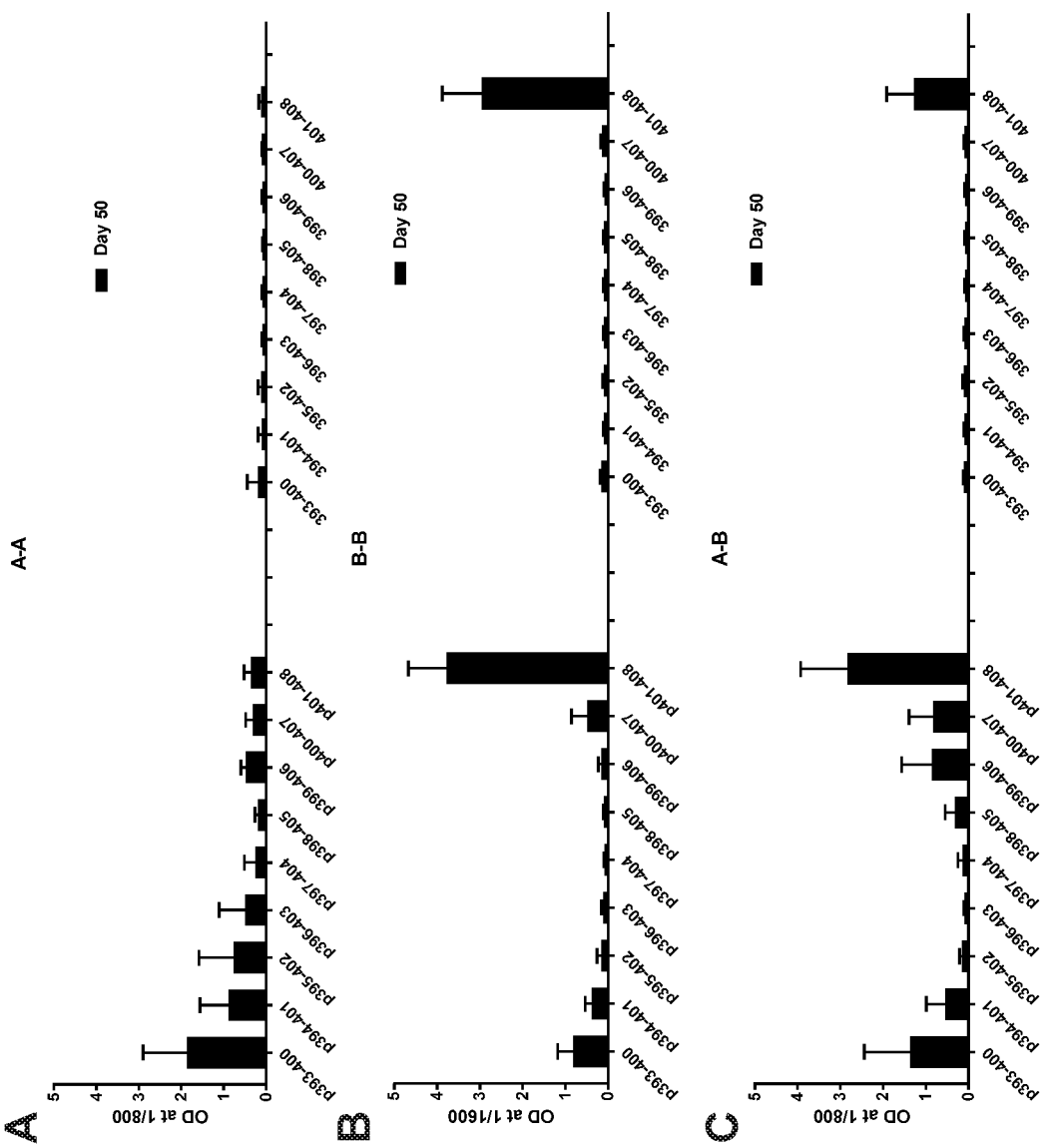
FIGS. 1A-1C show the epitope recognition profile of antibodies induced by homologous A-A (FIG. 1A) or B-B (FIG. 1B) vaccination or by heterologous A-B (FIG. 1C) vaccination, as determined by epitope mapping ELISA on short 8-mer overlapping peptides, covering phosphopeptide SEQ ID NO: 2 and peptide SEQ ID NO: 4.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition 1 or 2 is satisfied by any one of the following: 1 is true (or present) and 2 is false (or not present), 1 is false (or not present) and 2 is true (or present), and both 1 and 2 are true (or present).

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

According to embodiments of the application, an effective amount of liposomes comprises a Tau phosphopeptide at an amount of about 25 nmoles to about 750 nmoles per dose, such as about 29.7 nmoles to about 742.5 nmoles per dose, preferably about 90 nmoles to about 715 nmoles, such as about 89.1 nmoles to about 712.8 nmoles per dose, or about 90 nmoles to about 535 nmoles per dose, such as about 89.1 nmoles to about 534.6 nmoles per dose, or about 90 nmoles to about 275 nmoles per dose, such as about 89.1 nmoles to about 267.3 nmoles per dose of a Tau phosphopeptide comprising the amino acid sequence of one of SEQ ID NOs: 1-3 or 5-12. Preferably, the Tau phosphopeptide consists of the amino acid sequence of one of SEQ ID NO:27 to SEQ ID NO:38. More preferably, the Tau phosphopeptide consists of the amino acid sequence of SEQ ID NO:28. In one embodiment, the effective amount of liposomes comprises a toll-like receptor 4 agonist and a tetrapalmitoylated Tau phosphopeptide consisting of the amino acid sequence of SEQ ID NO: 28 at an amount of about 100 μg to about 2500 μg, preferably about 300 μg to about 2400 μg, per dose, corresponding to about 29.7 nmoles to about 742.5 nmoles, preferably about 89.1 nmoles to about 712.8 nmols.

According to embodiments of the application, an effective amount of liposomes comprises a Tau phosphopeptide, such as a Tau phosphopeptide comprising the amino acid sequence of one of SEQ ID NOs: 1-3 or 5-12, preferably a Tau phosphopeptide consisting of the amino acid sequence of one of SEQ ID NO:27 to SEQ ID NO:38, more preferably SEQ ID NO:28, at an amount of about 100 μg to about 2500 μg, about 300 μg to about 2400 μg, about 300 μg to about 1800 μg, or about 300 μg to about 900 μg per dose, such as about 100 μg, about 150 μg, about 200 μg, about 250 μg, about 300 μg, about 400 μg, about 500 μg, about 600 μg, about 700 μg, about 800 μg, about 900 μg, about 1000 μg, about 1100 μg, about 1200 μg, about 1300 μg, about 1400 μg, about 1500 μg, about 1600 μg, about 1700 μg, about 1800 μg, about 1900 μg, about 2000 μg, about 2100 μg, about 2200 μg, about 2300 μg, about 2400 μg, or about 2500 μg, or any value in between, per dose.

In certain embodiments, the effective amount of liposomes comprises the toll-like receptor 4 agonist at an amount of about 30 μg to about 900 μg, preferably about 100 μg to about 585 μg, per dose. In certain embodiments, the effective amount of liposomes comprises the toll-like receptor agonist monophosphoryl hexa-acyl Lipid A, 3-deacyl at an amount of about 30 μg, about 50 μg, about 100 μg, about 150 μg, about 200 μg, about 250 μg, about 300 μg, about 330 μg, about 360 μg, about 390 μg, about 420 μg, about 450 μg, about 480 μg, about 500 μg, about 520 μg, about 540 μg, about 560 μg, about 580 μg, about 600 μg, about 700 μg, about 800 μg or about 900 μg per dose.

In certain embodiments, the effective amount of liposomes comprises the lipidated CpG oligonucleotide at an amount of about 50 μg to about 1250 μg, preferably about 150 μg to about 800 μg, per dose. For example, the effective amount of liposomes can comprise a lipidated CpG oligonucleotide at an amount of about 50 μg, about 100 μg, about 150 μg, about 200 μg, about 250 μg, about 300 μg, about 350 μg, about 400 μg, about 450 μg, about 500 μg, about 550 μg, about 600 μg, about 650 μg, about 700 μg, about 750 μg, about 800 μg, about 850 μg, about 900 μg, about 950 μg, about 1000 μg, about 1050 μg, about 1100 μg, about 1200 μg, or about 1250 μg per dose. In certain embodiments, the effective amount of liposomes comprises a CpG oligonucleotide consisting of the nucleotide sequence of SEQ ID NO:18 at an amount of about 50 μg to about 1250 μg, preferably about 150 μg to about 800 μg, per dose.

According to embodiments of the application, the Tau phosphopeptide is presented on the surface of the liposomes.

As used herein, the immunologically effective amount of the conjugate is defined by the amount of the immunogenic carrier conjugated to the second Tau phosphopeptide in the conjugate. For example, 15 μg conjugate refers to a conjugate composition containing 15 μg immunogenic carrier that is conjugated to a Tau phosphopeptide. One or more Tau phosphopeptides can be conjugated to one immunogenic carrier.

According to embodiments of the application, an effective amount of conjugates can be determined using methods known in the art, such as clinical experience, in view of the present disclosure.

The Tau phosphopeptide comprises the amino acid sequence of one of SEQ ID NOs: 1-3 or 5-12. Preferably, the Tau phosphopeptide present on the liposomes consists of the amino acid sequence of one of SEQ ID NO: 27 to SEQ ID NO: 29 and SEQ ID NO: 31 to SEQ ID NO: 38. More preferably, the Tau phosphopeptide present on the liposomes consists of the amino acid sequence of SEQ ID NO:28. Preferably, the Tau phosphopeptide present in the conjugates consists of the amino acid sequence of one of SEQ ID NOs: 1-3 or 5-12, preferably SEQ ID NO: 2.

As used herein, the term "tau" or "tau protein", also known as microtubule-associated protein tau, MAPT, neurofibrillary tangle protein, paired helical filament-tau, PHF-tau, MAPTL, MTBT1, refers to an abundant central and peripheral nervous system protein having multiple isoforms. In the human central nervous system (CNS), six major tau isoforms ranging in size from 352 to 441 amino acids in length exist due to alternative splicing (Hanger et al., Trends Mol Med. 15:112-9, 2009). Examples of tau include, but are not limited to, tau isoforms in the CNS, such as the 441-amino acid longest tau isoform (4R2N) that has four repeats and two inserts and the 352-amino acid long shortest (fetal) isoform (3R0N) that has three repeats and no inserts. Examples of tau also include the "big tau" isoform expressed in peripheral nerves that contains 300 additional residues (exon 4a). Friedhoff et al., Biochimica et Biophysica Acta 1502 (2000) 122-132. Examples of tau include a human big tau that is a 758 amino acid-long protein encoded by an mRNA transcript 6762 nucleotides long (NM_016835.4), or isoforms thereof. The amino acid sequence of the exemplified human big tau is represented in GenBank Accession No. NP_058519.3. As used herein, the term "tau" includes homologs of tau from species other than human, such as *Macaca Fascicularis* (cynomolgous monkey) or Pan troglodytes (chimpanzee). As used herein, the term "tau" includes proteins comprising mutations, e.g., point mutations, fragments, insertions, deletions and splice variants of full length wild type tau. The term "tau" also encompasses post-translational modifications of the tau amino acid sequence. Post-translational modifications include, but are not limited to, phosphorylation.

As used herein, the term "phosphorylated Tau" refers to a tau protein, or a fragment or peptide thereof that contains at least one phosphorylated residue.

As used herein, the term "enriched paired helical filament" or "ePHF" refers to a preparation that is enriched for tau protein in the paired helical filament. The PHF is a prominent component of Alzheimer disease neurofibrillary tangles.

As used herein, the term "peptide" or "polypeptide" refers to a polymer composed of amino acid residues, related naturally occurring structural variants, and synthetic non-naturally occurring analogs thereof linked via peptide bonds. The term refers to a peptide of any size, structure, or function. Typically, a peptide is at least three amino acids long. A peptide can be naturally occurring, recombinant, or synthetic, or any combination thereof. Synthetic peptides can be synthesized, for example, using an automated polypeptide synthesizer. Examples of tau peptides include any peptide of tau protein of about 5 to about 30 amino acids in length, preferably of about 10 to about 25 amino acids in length, more preferably of about 16 to about 21 amino acids in length. In the present disclosure, peptides are listed from N to C terminus using the standard three or one letter amino acid abbreviation, wherein phosphoresidues are indicated with "p". Examples of tau peptides useful in the invention include, but are not limited to, tau peptides comprising the amino acid sequence of any of SEQ ID NOs: 1-12, or tau peptides having an amino acid sequence that is at least 75%, 80%, 85%, 90% or 95% identical to the amino acid sequence of any of SEQ ID NOs: 1-12.

As used herein, the term "phosphopeptide" or "phosphoepitope" refers to a peptide that is phosphorylated at one or more amino acid residues. Examples of tau phosphopeptides include any tau peptide comprising one or more phosphorylated amino acid residue. Examples of tau phosphopeptides useful in the invention include, but are not limited to, tau phosphopeptides comprising the amino acid sequence of any of SEQ ID NOs: 1-3 or 5-12, or tau phosphopeptides having an amino acid sequence that is at least 75%, 80%, 85%, 90% or 95% identical to the amino acid sequence of any of SEQ ID NOs: 1-3 or 5-12.

The tau peptides of the present invention can be synthesized by solid phase peptide synthesis or by recombinant expression systems. Automatic peptide synthesizers are commercially available from numerous suppliers, such as Applied Biosystems (Foster City, Calif.). Recombinant expression systems can include bacteria, such as E. coli, yeast, insect cells, or mammalian cells. Procedures for recombinant expression are described by Sambrook et al., Molecular Cloning: A Laboratory Manual (C.S.H.P. Press, NY 2d ed., 1989).

Tau is a human "self" protein. This means that, in principle, all lymphocytes bearing a receptor specific for tau should have been deleted during development (central tolerance) or rendered unresponsive by a peripheral tolerance mechanism. This problem has proved to be a significant roadblock to the development of vaccines against self or "altered self" proteins (e.g. tumor antigens).

Generating high-quality antibodies against an antigen (self or infectious) requires the action of not only B lymphocytes, which produce the antibody, but also of CD4+ T "helper" lymphocytes. CD4+ T-cells provide critical survival and maturation signals to B lymphocytes, and CD4+ T-cell deficient animals are profoundly immunosuppressed. CD4+ T-cells are also subject to tolerance mechanisms, and an additional roadblock to generating strong anti-self (e.g., anti-tau) antibody responses is that tau-reactive CD4+ T-cells are also likely to be rare to non-existent in the human/animal repertoire.

While not wishing to be bound by theory, it is believed, but in no way limiting the scope of the present invention, that this problem is circumvented by vaccine compositions of the present invention.

In one embodiment, a liposome comprising a tau peptide is produced that also comprises a T-cell epitope that is capable of binding most or all HLA DR (Human Leukocyte Antigen—antigen D Related) molecules. The T-cell epitope is then able to activate CD4+ T-cells and provides essential maturation and survival signals to the tau-specific B-cells. In another embodiment, a conjugate of a tau peptide with a carrier protein is produced, which generates a strong helper T-cell response. In this embodiment "non-linked recognition" is used, in which carrier-specific T-cells provide survival and maturation signals to self-reactive B-cells. Accordingly, the tau-specific B-cells receive crucial signals to trigger affinity maturation, immunoglobulin class switching, and to establish a long-term memory pool. The tau liposomes and tau conjugates can be used to generate high-quality antibodies against the tau antigen in homologous or heterologous immunization schemes, with either liposome or conjugate used in the prime and/or in the boost.

Liposomes

Liposomes are used in the present application in priming compositions, and optionally boosting compositions. Liposomes useful for methods of the invention comprise:

a tau peptide, preferably the tau peptide is a tau phosphopeptide; and a helper T-cell epitope, wherein the tau peptide is presented on the surface of the liposome.

Liposomes according to embodiments of the invention are also referred to herein as "improved liposomes," "improved liposomal vaccines" or "liposomal vaccines according to embodiments of the invention" or "Tau liposomes" or "optimized liposomal vaccines" of "2nd generation liposomes".

As used herein, the term "liposome" refers generally to a lipid vesicle that is made of materials having high lipid content, e.g., phospholipids, cholesterol. The lipids of these vesicles are generally organized in the form of lipid bilayers. The lipid bilayers generally encapsulate a volume which is either interspersed between multiple onion-like shells of lipid bilayers, forming multilamellar lipid vesicles (MLVs) or contained within an amorphous central cavity. Lipid vesicles having an amorphous central cavity are unilamellar lipid vesicles, i.e., those with a single peripheral bilayer surrounding the cavity. Large unilamellar vesicles (LUVs) generally have a diameter of 100 nm to few micrometer, such as 100-200 nm or larger, while small unilamellar lipid vesicles (SUV) generally have a diameter of less than 100 nm, such as 20-100 nm, typically 15-30 mm.

According to particular embodiments, the liposome comprises one or more tau peptides. According to particular embodiments, the tau peptides on the liposome can be the same or different.

Any suitable tau peptide known to those skilled in the art can be used in the invention in view of the present disclosure. According to particular embodiments, one or more of the tau peptides comprise the amino acid sequence of one of SEQ ID NOs: 1-12. In other embodiments, one or more of the tau peptides comprise an amino acid sequence that is at least 75%, 80%, 85%, 90% or 95% identical to the amino acid sequence of one of SEQ ID NOs: 1-12, wherein none of the amino acid residues are phosphorylated, or one or more amino acid residues are phosphorylated.

According to particular embodiments, one or more of the tau peptides is a tau phosphopeptide. According to particular embodiments, the one or more tau phosphopeptides comprise the amino acid sequence of one of SEQ ID NOs: 1-3 or 5-12, or an amino acid sequence that is at least 75%, 80%, 85%, 90% or 95% identical to the amino acid sequence of one of SEQ ID NOs: 1-3 or 5-12, wherein one or more of the indicated amino acid residues are phosphorylated. Preferably, the tau phosphopeptide comprises the amino acid sequence of one of SEQ ID Nos: 1-3. The tau peptide can have the C-terminus amidated.

According to embodiments of the application, a tau peptide is presented on the surface of the liposome. A tau peptide, preferably a tau phosphopeptide, can be presented on the surface of the liposome using methods known in the art in view of the present disclosure. See, for example, the relevant disclosure in U.S. Pat. Nos. 8,647,631 and 9,687,447, the content of which is incorporated herein by reference. According to particular embodiments, the one or more tau peptides, including phosphopeptides, further comprise one or more modifications, such as palmitoylation or dodecyl modification to allow the tau peptides to be presented on the surface of the liposome. Additional amino acid residues, such as Lys, Cys, or sometimes Ser or Thr, can be added to the tau peptide to facilitate the modification. It was reported that the position of lipid anchors induces different conformations of the peptide sequence (Hickman et al., J. Biol. Chem. vol. 286, NO. 16, pp. 13966-13976, Apr. 22, 2011). While not wishing to be bound by theory, it is believed that adding hydrophobic moieties at both termini may increase the pathological beta-sheet conformation of the tau peptide. Thus, the one or more tau peptides further comprise hydrophobic moieties at both termini. The modified tau peptide can have the C-terminus amidated. Preferably, a tau peptide presented on the surface of the liposome consists of the amino acid sequence of one of SEQ ID NO:27 to SEQ ID NO:38. More preferably, the peptide is a tau phosphopeptide having an amino acid sequence selected from the group consisting of SEQ ID NO: 27 to SEQ ID NO: 29 or SEQ ID NO: 31 to SEQ ID NO: 38.

As used herein, the term "helper T-cell epitope" refers to a polypeptide comprising an epitope that is capable of recognition by a helper T-cell. Examples of helper T-cell epitopes include, but are not limited to, tetanus toxoid (e.g., the P2 and P30 epitopes, also named, respectively as T2 and T30), Hepatitis B surface antigen, cholera toxin B, toxoid, diphtheria toxoid, measles virus F protein, *Chlamydia trachomatis* major outer membrane protein, *Plasmodium falciparum* circumsporozite T, *P. falciparum* CS antigen, *Schistosoma mansoni* triose phosphate isomerase, *Bordetella pertussis, Clostridium tetani, Pertusaria trachythallina, Escherichia coli* TraT, and Influenza virus hemagglutinin (HA).

Any suitable helper T-cell epitope known to those skilled in the art can be used in the invention in view of the present disclosure. According to particular embodiments, the helper T-cell epitope comprises at least one amino acid sequence selected from the group consisting of SEQ ID NO:23 to SEQ ID NO:26. Preferably, the helper T-cell epitope comprises two or more of the amino acid sequences of SEQ ID NO:23 to SEQ ID NO:26 fused together via a linker, such as a peptide linker comprising one or more amino acids, e.g., Val (V), Ala (A), Arg (R), Gly (G), Ser (S), Lys (K). The length of the linker can vary, preferably 1-5 amino acids. Preferably, the helper T-cell epitope comprises three or more of the amino acid sequences of SEQ ID NO:23 to SEQ ID NO:26 fused together via one or more linkers selected from the group consisting of VVR, GS, RR, RK. The helper T-cell epitope can have its C-terminus amidated.

According to embodiments of the application, the helper T-cell epitopes can be incorporated on the liposomal surface, e.g. anchored by a covalently bound hydrophobic moiety wherein said hydrophobic moiety is an alkyl group, a fatty acid, a triglyceride, diglyceride, steroid, sphingolipid, glycolipid or a phospholipid, particularly an alkyl group or a fatty acid, particularly with a carbon backbone of at least 3 carbon atoms, particularly of at least 4 carbon atoms, particularly of at least 6 carbon atoms, particularly of at least 8 carbon atoms, particularly of at least 12 carbon atoms, particularly of at least 16 carbon atoms. In one embodiment of the invention, the hydrophobic moiety is palmitic acid. Alternatively, the helper T-cell epitopes can be encapsulated in the liposomes. According to particular embodiments, the helper T-cell epitope is encapsulated in the liposome.

The helper T-cell epitope can be modified for its desired location in the liposomes using methods known in the art in view of the present disclosure. According to particular embodiments, the helper T-cell epitope useful for the invention comprises an amino acid sequence of one of SEQ ID NO:39 to SEQ ID NO:44. Preferably, the helper T cell epitope consists of an amino acid sequence selected from the group consisting of SEQ ID NO:13 to SEQ ID NO:17.

According to particular embodiments, the liposome comprises a tau peptide and a helper T-cell epitope at a weight ratio of 1:1, 2:1, 3:1, 4:1, 5:1 or 6:1.

In an embodiment, the liposome further comprises at least one adjuvant comprising a toll-like receptor ligand. Thus, in another general aspect, the invention relates to a liposome, comprising:
    a tau peptide, preferably a tau phosphopeptide;
    a helper T-cell epitope; and
    at least one of
    a toll-like receptor 9 ligand, and
    a toll-like receptor 4 ligand.

As used herein, the term "toll-like receptor" or "TLR" refers to a class of pattern recognition receptor (PRR) proteins that play a key role in the innate immune response. TLRs recognize pathogen-associated molecular patterns (PAMPs) from microbial pathogens, such as bacteria, fungi, parasites and viruses, which can be distinguished from host molecules. TLRs are membrane-spanning proteins that typically function as dimers and are expressed by cells involved in the innate immune response, including antigen-presenting dendritic cells and phagocytic macrophages. There are at least ten human TLR family members, TLR1 to TLR10, and at least twelve murine TLR family members, TLR1 to TLR9 and TLR11 to TLR13, and they differ in the types of antigens they recognize. For example, TLR4 recognizes lipopolysaccharides (LPS), a component present in many Gram-negative bacteria, as well as viral proteins, polysaccharide, and endogenous proteins such as low-density lipoprotein, beta-defensins and heat shock protein; and TLR9 is a nucleotide-sensing TLR which is activated by unmethylated cytosine-phosphate-guanine (CpG) single-stranded or double-stranded dinucleotides, which are abundant in prokaryotic genomes but rare in vertebrate genomes. Activation of TLRs leads to a series of signaling events resulting in the production of type I interferons (IFNs), inflammatory cytokines, and chemokines, and the induction of immune responses. Eventually, this inflammation also activates the adaptive immune system, which then results in the clearance of the invading pathogens and the infected cells.

As used herein, the term "ligand" refers to a molecule that forms a complex with a biomolecule (e.g., a receptor) to serve a biological purpose. According to particular embodiments, the toll-like receptor ligand is a toll-like receptor agonist.

As used herein, the term "agonist" refers to a molecule that binds to one or more TLRs and induces a receptor mediated response. For example, an agonist can induce, stimulate, increase, activate, facilitate, enhance, or up regulate the activity of the receptor. Such activities are referred to as "agonistic activities." For example, a TLR4 or TLR9 agonist can activate or increase cell signaling through the bound receptor. Agonists include, but are not limited to nucleic acids, small molecules, proteins, carbohydrates, lipids or any other molecules that bind or interact with receptors. Agonists can mimic the activity of a natural receptor ligand. Agonists can be homologous to these natural receptor ligands with respect to sequence, conformation, charge or other characteristics such that they can be recognized by the receptors. This recognition can result in physiologic and/or biochemical changes within the cell, such that the cell reacts to the presence of the agonist in the same manner as if the natural receptor ligand were present. According to particular embodiments, the toll-like receptor agonist is at least one of a toll-like receptor 4 agonist and a toll-like receptor 9 agonist.

As used herein, the term "toll-like receptor 4 agonist" refers to any compound that acts as an agonist of TLR4. Any suitable toll-like receptor 4 agonist known to those skilled in the art in view of the present disclosure can be used in the invention. Examples of toll-like receptor 4 ligand useful for the invention include TLR4 agonist, including, but not limited to, monophosphoryl lipid A (MPLA). As used herein, the term "monophosphoryl lipid A" or MPLA" refers to a modified form of lipid A, which is the biologically active part of Gram-negative bacterial lipopolysaccharide (LPS) endotoxin. MPLA is less toxic than LPS while maintaining the immunostimulatory activity. As a vaccine adjuvant, MPLA stimulates both cellular and humoral responses to the vaccine antigen. Examples of MPLA include, but are not limited to, 3-O-desacyl-4'-monophosphoryl lipid A, monophosphoryl hexa-acyl lipid A, 3-deacyl, monophosphoryl 3-deacyl lipid A, and structurally related variants thereof. MPLA useful for the invention can be obtained using methods known in the art, or from a commercial source, such as 3D-(6-acyl) PHAD®, PHAD®, PHAD®-504, 3D-PHAD® from Avanti Polar Lipids (Alabaster, Ala., USA) or MPL™ from various commercial sources. According to particular embodiments, the toll-like receptor 4 agonist is MPLA.

As used herein, the term "toll-like receptor 9 agonist" refers to any compound that acts as an agonist of TLR9. Any suitable toll-like receptor 9 agonist known to those skilled in the art in view of the present disclosure can be used in the invention. Examples of toll-like receptor 9 ligand useful for the invention include TLR9 agonist including, but not limited to, CpG oligonucleotides.

As used herein, the term "CpG oligonucleotide", "CpG oligodeoxynucleotide" or "CpG ODN" refers to an oligonucleotide comprising at least one CpG motif. As used herein, "oligonucleotide," "oligodeoxynucleotide" or "ODN" refers to a polynucleotide formed from a plurality of linked nucleotide units. Such oligonucleotides can be obtained from existing nucleic acid sources or can be produced by synthetic methods. As used herein, the term "CpG motif" refers to a nucleotide sequence which contains unmethylated cytosine-phosphate-guanine (CpG) dinucleotides (i.e., a cytosine (C) followed by a guanine (G)) linked by a phosphate bond or a phosphodiester backbone or other internucleotide linkages.

According to particular embodiments, the CpG oligonucleotide is lipidated, i.e. conjugated (covalently linked) to a lipid moiety.

As used herein, a "lipid moiety" refers to a moiety containing a lipophilic structure. Lipid moieties, such as an alkyl group, a fatty acid, a triglyceride, diglyceride, steroid, sphingolipid, glycolipid or a phospholipid, particularly a sterol such as cholesterol, or fatty acids, when attached to highly hydrophilic molecules, such as nucleic acids, can substantially enhance plasma protein binding and consequently circulation half-life of the hydrophilic molecules. In addition, binding to certain plasma proteins, such as lipoproteins, has been shown to increase uptake in specific tissues expressing the corresponding lipoprotein receptors (e.g., LDL-receptor HDL-receptor or the scavenger receptor SR-B1). In particular, a lipid moiety conjugated to the phosphopeptides and/or CpG oligonucleotide allows anchoring the said peptides and/or oligonucleotides into the membrane of a liposome via a hydrophobic moiety.

According to particular embodiments, in view of the present disclosure, the CpG oligonucleotide can comprise any suitable internucleotide linkages.

As used herein, the term "internucleotide linkage" refers to a chemical linkage to join two nucleotides through their sugars consisting of a phosphorous atom and a charged or neutral group between adjacent nucleosides. Examples of internucleotide linkage include phosphodiester (po), phosphorothioate (ps), phosphorodithioate (ps2), methylphosphonate (mp), and methylphosphorothioate (rp). Phosphorothioate, phosphorodithioate, methylphosphonate and methylphosphorothioate are stabilizing internucleotide linkages, while phosphodiester is a naturally-occurring internucleotide linkage. Oligonucleotide phosphorothioates are typically synthesized as a random racemic mixture of Rp and Sp phosphorothioate linkages.

Any suitable CpG oligonucleotide known to those skilled in the art can be used in the invention in view of the present disclosure. Examples of such CpG oligonucleotides include, but are not limited to CpG2006 (also known as CpG 7909), CpG 1018, CpG2395, CpG2216, CpG1826 or CpG2336.

A CpG oligonucleotide can be lipidated using methods known in the art in view of the present disclosure. In some embodiments, 3' terminus of a CpG oligonucleotide is covalently linked to a cholesterol molecule through a phosphate bond, optionally via a PEG linker. Other lipophilic moiety can also be covalently linked to the 3' terminus of a CpG oligonucleotide. For example a CpG oligonucleotide can be covalently linked to a lipid anchor of the same length as the phospholipids from liposome: one palmitic acid chain (using Pal-OH or similar, activated for coupling) or two palmitic acids (e.g., using 1,2-dipalmitoyl-sn-glycero-3-phosphoethanolamine-N-(succinyl) or similar, activated for coupling), optionally via a PEG linker. See, e.g., relevant disclosure in U.S. Pat. No. 7,741,297, the content of which is incorporated herein by reference. The length of PEG can vary, from example, from 1 to 5 PEG units.

Other linkers can also be used to covalently connect a CpG oligonucleotide to a lipophilic moiety (such as a cholesterol molecule), examples of which include, but are not limited to an alkyl spacer having 3 to 12 carbons. A short linker compatible with oligonucleotide chemistry is needed as aminodiol. In some embodiment, no linker is used for the covalent bonding. See e.g., Ries et al., "Convenient synthesis and application of versatile nucleic acid lipid membrane anchors in the assembly and fusion of liposomes, Org. Biomol. Chem., 2015, 13, 9673, the relevant disclosure of which is incorporated herein by reference.

According to particular embodiments, lipidated CpG oligonucleotide useful for the invention comprises a nucleotide sequence selected from the group consisting of SEQ ID NO:18 to SEQ ID NO:22, wherein the nucleotide sequence comprises one or more phosphorothioate internucleotide linkages, and the nucleotide sequence is covalently linked to at least one cholesterol via a linker. Any suitable linkers can be used to covalently link a CpG oligonucleotide to a cholesterol molecule. Preferably, the linker comprises polyethylene glycol (PEG).

According to particular embodiments, the liposome comprises:
 a tau phosphopeptide;
 a helper T-cell epitope;
 a lipidated CpG oligonucleotide; and
 a toll-like receptor 4 ligand;
 wherein the tau phosphopeptide is presented on the surface of the liposome, and the helper T-cell epitope is encapsulated in the liposome.

According to particular embodiments, the liposome comprises:

a tau peptide having an amino acid sequence selected from the group consisting of SEQ ID NO: 27 to SEQ ID NO: 29 or SEQ ID NO: 31 to SEQ ID NO: 38;

a helper T cell epitope having an amino acid sequence selected from the group consisting of SEQ ID NO:39 to SEQ ID NO:44, preferably, the helper T cell epitope consisting of an amino acid sequence selected from the group consisting of SEQ ID NO:13 to SEQ ID NO:17;

a lipidated CpG oligonucleotide having a nucleotide sequence selected from the group consisting of SEQ ID NO:18 to SEQ ID NO:22, wherein the CpG oligonucleotide comprises one or more phosphorothioate internucleotide linkages, and the CpG oligonucleotide is covalently linked to at least one cholesterol via a linker; and monophosphoryl lipid A (MPLA).

According to particular embodiments, the liposome further comprises one or more lipids selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol.

According to particular embodiments, the liposome further comprises a buffer. Any suitable buffer known to those skilled in the art in view of the present disclosure can be used in the invention. In one embodiment, the liposome comprises a phosphate-buffered saline. According to particular embodiments, the buffer comprises histidine and sucrose.

According to particular embodiments, the liposome comprises DMPC, DMPG, cholesterol, tau phosphopeptide and helper T-cell epitope at a molar ratio of 9:1:7:0.07:0.04.

Liposomes of the invention can be made using methods known in the art in view of the present disclosure.

An exemplary liposome of the present application comprises a tau tetrapalmitoylated phosphopeptide (pTau Peptide T3, SEQ ID NO: 28) presented on the surface of the liposome via two palmitic acids at each terminus of the tau peptide; a TLR-9 ligand comprising lipidated CpG (Adjuvant CpG7909-Chol) incorporated into the liposome membrane via the covalently linked cholesterol; a TLR-4 ligand (Adjuvant 3D-(6-acyl) PHAD®) incorporated into the membrane; and an encapsulated helper T-cell epitope (PAN-DR binder T50).

Conjugates

Conjugates are used in boosting compositions of the application. Conjugates useful in the methods of the invention comprise a tau peptide, preferably a tau phosphopeptide, and an immunogenic carrier conjugated thereto.

According to particular aspects, the conjugate has the following structure:

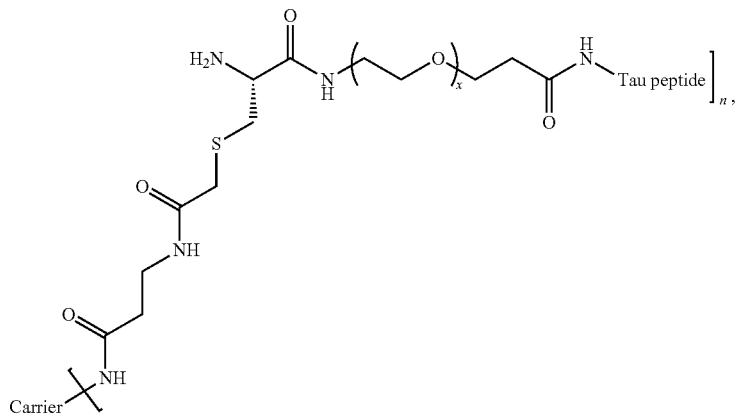

or the structure of formula (II):

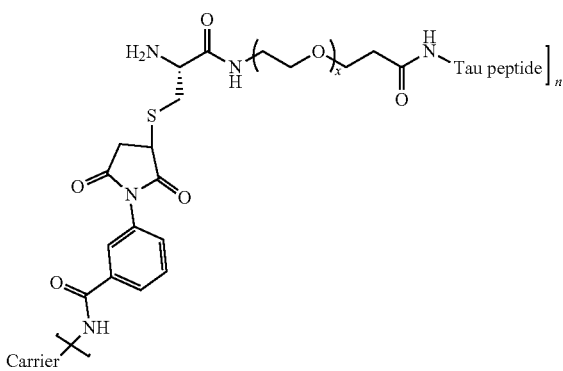

wherein x is an integer of 0 to 10;

n is an integer of 2 to 15, preferably 3-11;

Carrier represents an immunogenic carrier; and

Tau peptide represents a tau phosphopeptide.

According to particular embodiments, x is an integer of 1 to 10, 2 to 9, 2 to 8, 2 to 7, 2 to 6, 2 to 5, 2 to 4, or 2 to 3. According to particular embodiments, x is 3.

According to particular embodiments, n is 2 to 15, 3 to 11, 3 to 9, 3 to 8, or 3 to 7.

According to particular embodiments, the conjugate comprises one or more tau peptides. According to particular embodiments, the tau peptides of the conjugate can be the same or different.

According to particular embodiments, in view of the present disclosure, any suitable tau peptides can be used in the invention. According to particular embodiments, one or more of the tau peptides comprise the amino acid sequence of one of SEQ ID NOs: 1-12, or an amino acid sequence that is at least 75%, 80%, 85%, 90% or 95% identical to the amino acid sequence of one of SEQ ID NOs: 1-12, wherein none, one or more of the amino acid residues are phosphorylated.

According to particular embodiments, one or more of the tau peptides is a tau phosphopeptide. According to particular embodiments, the one or more tau phosphopeptides comprise the amino acid sequence of one of SEQ ID NOs: 1-3 or 5-12, or an amino acid sequence that is at least 75%, 80%, 85%, 90% or 95% identical to the amino acid sequence of one of SEQ ID NOs: 1-3 or 5-12, wherein one or more of the indicated amino acid residues are phosphorylated.

According to particular embodiments, the tau phosphopeptide consists of the amino acid sequence of one of SEQ ID NOs: 1-3.

m-maleimidobenzoyl-N-hydroxysuccinimide ester-cysteine-(C$_2$H$_4$O)x, wherein x is an integer of 0 to 10, such as 0, 1, 2, 3, 4, 5, 6, 7, 8, 9, or 10.

According to particular embodiments, the carrier is covalently linked to the N-terminus of the tau peptide, via a linker.

According to other particular embodiments, the carrier is covalently linked to the C-terminus of the tau peptide, via a linker.

According to particular embodiments, the conjugate has the structure of:

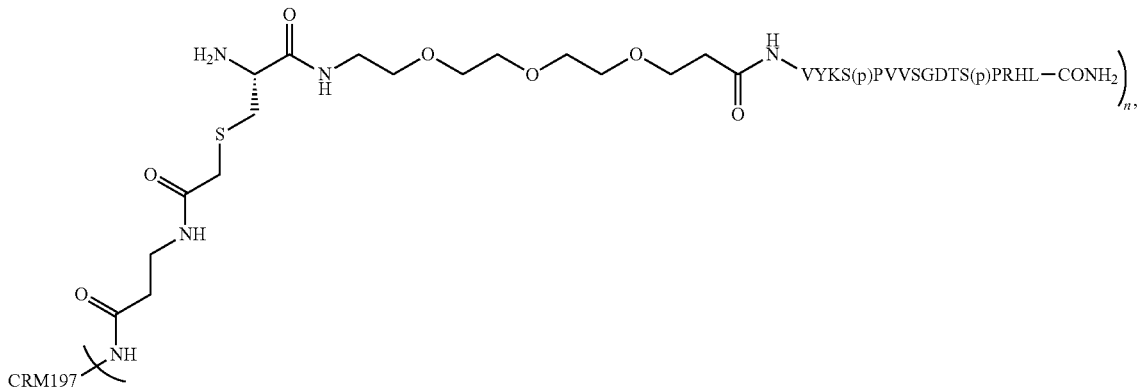

wherein n is an integer of 2 to 15, preferably 3-11, more preferably 3-7 and VYKS(p)PVVSGDTS(p)PRHL-CONH$_2$ comprises the phospho-tau peptide of SEQ ID NO:2.

Conjugates of the invention can be made by methods known in the art in view of the present disclosure. For example, the above conjugate can be formed by reacting succinimidyl-3-(bromoacetamido)propionate (SBAP):

As used herein, the term "immunogenic carrier" refers to an immunogenic substance that can be coupled to a tau peptide. An immunogenic moiety coupled to a tau peptide can induce an immune response and elicit the production of antibodies that can specifically bind the tau peptide. Immunogenic moieties are operative moieties that include proteins, polypeptides, glycoproteins, complex polysaccharides, particles, nucleic acids, polynucleotides, and the like that are recognized as foreign and thereby elicit an immunologic response from the host. Any suitable immunogenic carrier known to those skilled in the art in view of the present disclosure can be used in the invention. According to particular embodiments, the immunogenic carrier is keyhole limpet hemocyanin (KLH), tetanus toxoid, CRM197 (a non-toxic form of diphtheria toxin), an outer membrane protein mixture from *N. meningitidis* (OMP), or a derivative thereof. According to particular embodiments, the immunogenic carrier is KLH or CRM197.

According to particular embodiments, the tau peptide is conjugated to the carrier via a linker. As used herein, the term "linker" refers to a chemical moiety that joins a immunogenic carrier to a tau peptide. Any suitable linker known to those skilled in the art in view of the present disclosure can be used in the invention. The linkers can be, for example, a single covalent bond, a substituted or unsubstituted alkyl, a substituted or unsubstituted heteroalkyl moiety, a polyethylene glycol (PEG) linker, a peptide linker, a sugar-based linker, or a cleavable linker, such as a disulfide linkage or a protease cleavage site, or an amino acid, or a combination thereof. Examples of the linker can comprises one or more of polyethylene glycol (PEG), succinimidyl 3-(bromoacetamido)propionate (SBAP), m-maleimidobenzoyl-N-hydroxysuccinimide ester (MBS), or one or more amino acids such as Cys, Lys or sometimes Ser or Thr, or a combination thereof.

According to particular embodiments, the linker comprises (C$_2$H$_4$O)x-cysteine-acetamidopropionamide or

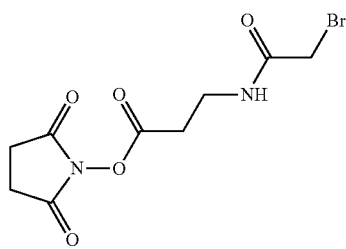 [SMILES: O=C(CBr)NCCC(=O)ON1C(=O)CCC1=O]

with an amino group of CRM197 to form an amide linkage. This CRM197 precursor can be subsequently reacted with the tau peptide (e.g., the phosphorylated tau peptide of SEQ ID NO: 2) conjugated at its N-terminus or at its C-terminus to a PEG-cysteine linker with a free nucleophilic thiol group to form the tau phosphopeptide conjugate.

An exemplary conjugate according to an embodiment of the present application comprises multiple tau phosphopeptides (pTau Peptide T3.76) covalently linked to a carrier protein CRM197.

Pharmaceutical Compositions

Liposomes and conjugates are administered to the subject in pharmaceutical compositions. Pharmaceutical compositions are compositions comprising a therapeutically effective amount of a liposome or compositions comprising a therapeutically effective amount of a conjugate of the invention, each together with a pharmaceutically acceptable carrier. Pharmaceutically acceptable carriers include excipients and/or carriers known in the art (see Remington's Pharmaceutical Science (15th ed.), Mack Publishing Company, Easton, Pa., 1980). The preferred formulation of the pharmaceutical composition depends on the intended mode of administration and therapeutic application. The compositions can include pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, non-immunogenic stabilizers, and the like. It will be understood that the characteristics of the carrier, excipient or diluent will depend on the route of administration for a particular application, e.g., intramuscular, subcutaneous, oral, intradermal, cutaneous, intramucosal (e.g., gut), intranasal or intraperitoneal routes. Preferably, the pharmaceutically acceptable carrier included in the pharmaceutical compositions is suitable for intramuscular administration.

The pharmaceutical compositions can be formulated as a vaccine (also referred to as an "immunogenic composition"), such as a priming composition or a boosting composition, according to methods well known in the art.

The pharmaceutical compositions can contain a mixture of the same immunogenic tau peptide. Alternatively, the pharmaceutical compositions can contain a mixture of different immunogenic tau peptides of the present invention.

Another problem associated with vaccines against neuronal diseases is that exceptionally high antibody titers are likely to be necessary to assure efficacy. This is because the target antigen for the vaccine is located in the brain. The brain is separated from the circulation by a specialized cellular structure called the blood-brain barrier (BBB). The BBB restricts passage of substances from the circulation into the brain. This prevents the entry of toxins, microbes, etc. into the central nervous system. The BBB also has the potentially less desirable effect of preventing the efficient entry of immune mediators (such as antibodies) into the interstitial and cerebrospinal fluid that surrounds the brain.

Approximately 0.1% of antibodies that are present in the systemic circulation cross the BBB and enter the brain. This means that systemic titers induced by a vaccine targeting a CNS antigen must be at least 1000 times greater than the minimal effective titer to be efficacious in the brain.

According to particular embodiments, the pharmaceutical compositions of the present invention therefore further comprise one or more suitable adjuvants. Thus, the tau peptides of the present invention, present in the liposome or the conjugate, can be administered in combination with a suitable adjuvant to achieve the desired immune response in the subject. Suitable adjuvants can be administered before, after, or concurrent with administration of liposome or conjugate of the present invention. Preferred adjuvants augment the intrinsic response to an immunogen without causing conformational changes in the immunogen that affect the qualitative form of the response. Examples of adjuvants are the aluminum salts (alum), such as aluminum hydroxide, aluminum phosphate, and aluminum sulfate. Other examples of adjuvants include CpG, such as CpG2006 (also known as CpG 7909), CpG 1018, CpG2395, CpG2216, CpG1826 or CpG2336. Such adjuvants can be used with or without other specific immunostimulating agents, such as MPLA Class (3 De-O-acylated monophosphoryl lipid A (MPL™), monophosphoryl hexa-acyl Lipid A, 3-deacyl synthetic (3D-(6-acyl) PHAD®), PHAD™, PHAD®-504, 3D-PHAD®) lipid A, polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2' dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include MF59 (see WO 90/14837), containing 5% Squalene, 0.5% Tween 80, and 0.5% Span 85 (optionally containing various amounts of MTP-PE) formulated into submicron particles using a microfluidizer; SAF, containing 10% Squalene, 0.4% Tween 80, 5% pluronic-blocked polymer L121, and thr-MDP, either microfluidized into a submicron emulsion or vortexed to generate a larger particle size emulsion; and the Ribi™ adjuvant system (RAS) (Ribi ImmunoChem, Hamilton, Mont.) 0.2% Tween 80, and one or more bacterial cell wall components selected from the group consisting of monophosphoryl lipid A (MPL™), trehalose dimycolate (TDM), and cell wall skeleton (CWS), preferably MPL™+CWS (Detox™). Other adjuvants include Complete Freund's Adjuvant (CFA), and cytokines, such as interleukins (IL-1, IL-2, and IL-12), macrophage colony stimulating factor (M-CSF), and tumor necrosis factor (TNF).

As used herein, the term "therapeutically effective amount" refers to an amount of an active ingredient or component that elicits the desired biological or medicinal response in a subject. A therapeutically effective amount can be determined empirically and in a routine manner, in relation to the stated purpose. For example, in vitro assays can optionally be employed to help identify optimal dosage ranges. Selection of a particular effective dose can be determined (e.g., via clinical trials) by those skilled in the art based upon the consideration of several factors, including the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

In certain embodiments, the "therapeutically effective amount" is an "immunologically effective amount", which means an amount of a composition sufficient to induce a desired immune effect or immune response in a subject in need thereof. In one embodiment, an immunogenically effective amount means an amount sufficient to induce an immune response in a subject in need thereof. In another embodiment, an immunogenically effective amount means an amount sufficient to produce immunity in a subject in need thereof, e.g., provide a therapeutic effect against a neurodegenerative disease, disorder or condition. An immunogenically effective amount can vary depending upon a variety of factors, such as the physical condition of the subject, age, weight, health, etc. An immunogenically effective amount can readily be determined by one of ordinary skill in the art in view of the present disclosure.

In one embodiment, an immunogenic composition is a priming composition used for priming an immune response, which is to be administered before the administration of a boosting composition. According to embodiments of the invention, a priming composition comprises an immunologically effective amount of a liposome described herein. According to embodiments of the invention, an immunogenic composition is a boosting composition used for boosting an immune response, which is to be administered after the administration of a boosting composition. According to embodiments of the invention, a boosting composition comprises an immunologically effective amount of a conjugate described herein. According to embodiments of the application, an immunogenic composition comprising an immunologically effective amount of a lispoomse described herein can be used as both a priming composition for priming an immune response and a boosting composition for boosting the immune response. A priming composition can be used in combination with one or more boosting compositions. The boosting compositions can be administered more than once.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a liposome composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, 12 weeks or more before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, 12 weeks or more after) the administration of a second therapy (e.g., a conjugate composition described herein) to a subject.

Pharmaceutical compositions of the present invention can be formulated according to methods well known in the art. The optimal ratios of each component in the compositions can be determined by techniques well known to those skilled in the art in view of the present disclosure.

In certain embodiments, a pharmaceutical composition comprises a liposome described herein and a buffer comprising one or more amino acids, such as histidine or glycine, and/or one or more carbohydrates, such as glucose or sucrose.

In other embodiments, a pharmaceutical composition comprises a conjugate described herein and a buffer comprising one or more amino acids, such as histidine or glycine, one or more carbohydrates, such as glucose or sucrose, and/or a surfactant, such as polysorbate 80, polysorbate 20, and so on.

Methods of Use

The invention provides a method of priming and boosting an immune response against a tau protein in a subject suffering from a neurodegenerative disorder using a liposomal vaccine containing tau peptides and a conjugate vaccine comprising tau peptides conjugated to an immunogenic carrier.

In one general aspect, a method of inducing an immune response against a tau protein in a subject suffering from a neurodegenerative disorder comprises:

administering to the subject a priming composition comprising an immunologically effective amount of a liposome comprising:

a first tau phosphopeptide;
a helper T-cell epitope;
a lipidated CpG oligonucleotide; and
an adjuvant containing a toll-like receptor 4 ligand;
wherein the tau phosphopeptide is presented on the surface of the liposome,
and the priming composition further comprises a pharmaceutically acceptable carrier; and administering to the subject a first boosting composition comprising an immunologically effective amount of a conjugate comprising a second tau phosphopeptide and an immunogenic carrier conjugated thereto via a linker, the conjugate having the structure of formula (I):

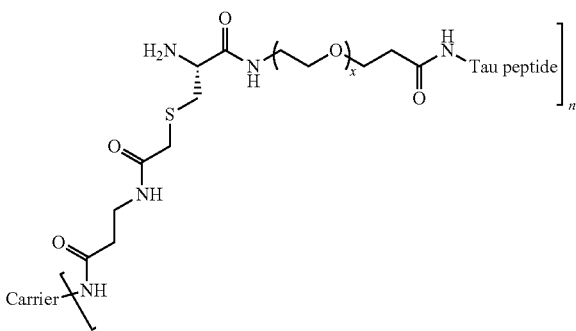

or having the structure of formula (II):

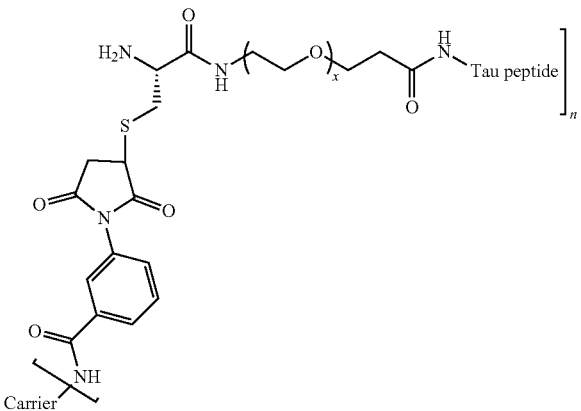

wherein
x is an integer of 0 to 10, preferably 2 to 6, most preferably 3;
n is an integer of 3 to 15, preferably 3 to 12;
Carrier represents the immunogenic carrier selected from the group consisting of keyhole limpet hemocyanin (KLH), tetanus toxoid, CRM197 and an outer membrane protein mixture from N. meningitidis (OMP), or a derivative thereof; and
Tau peptide represents the second tau phosphopeptide, and
the first boosting composition further comprises a pharmaceutically acceptable carrier wherein the first tau phosphopeptide and second tau phosphopeptide each independent has an amino acid sequence selected from the group consisting of SEQ ID NO: 1 to SEQ ID NO: 3 and SEQ ID NO: 5 to SEQ ID NO: 12.

In certain embodiments, the immunologically effective amount of the conjugate is administered together with one or more adjuvants, such as those described herein. In one embodiment, the immunologically effective amount of the conjugate is administered with one or more of aluminum salts (alum), such as aluminum hydroxide, aluminum phosphate, and aluminum sulfate, and/or one or more of CpGs, such as CpG2006 (also known as CpG 7909), CpG 1018, CpG2395, CpG2216, CpG1826 or CpG2336.

In certain embodiments, the first tau phosphopeptide and second tau phosphopeptide are identical. In other embodiments, the first tau phosphopeptide and second tau phosphopeptide are different, preferably they share at least one common epitope.

In certain embodiment, the method further comprises administering to the subject a second boosting composition comprising an immunogenic effective amount of the liposome.

According to particular aspects, the immune response is induced antibodies against phosphorylated tau protein, preferably ePHF.

In certain embodiments, the first boosting composition is administered at about 27-32 days, such as about 27, 28, 29, 30, 21 or 32 days after the priming composition is administered. In certain embodiments, the first boosting composition is re-administered at about 82-87 days, such as about 82, 83, 84, 85, 86 or 87 days after the priming composition is administered. In certain embodiments, a second boosting composition comprising an immunogenic effective amount of the liposome is administered at about 167-172 days, such as about 167, 168, 169, 170, 171 or 172 days after the priming composition is administered.

In certain embodiments, the first boosting composition is administered at about 82-87 days, such as about 82, 83, 84, 85, 86 or 87 days after the priming composition is administered. In certain embodiments, the second boosting composition is administered at about 27-32 days, such as about 27, 28, 29, 30, 21 or 32 days after the priming composition is administered. In certain embodiments, the first boosting composition is re-administered at about 167-172 days, such as about 167, 168, 169, 170, 171 or 172 days after the priming composition is administered.

One of ordinary skill in the art will be able to vary the exact timing of the priming and boosting compositions, frequency of administration thereof, dosage thereof, etc., based upon the teachings herein and clinical experience.

Any of the primer and boosting composition compositions described herein can be used in a method of inducing an immune response against a tau protein in a subject suffering from a neurodegenerative disorder. Embodiments of the priming composition; boosting composition; liposomes; and/or conjugates, etc. that can be used in the methods of the invention are discussed in detail above and in the illustrative examples below.

As used herein, the terms "induce" and "stimulate" and variations thereof refer to any measurable increase in cellular activity. Induction of an immune response can include, for example, activation, proliferation, or maturation of a population of immune cells, increasing the production of a cytokine, and/or another indicator of increased immune function. In certain embodiments, induction of an immune response can include increasing the proliferation of B cells, producing antigen-specific antibodies, increasing the proliferation of antigen-specific T cells, improving dendritic cell antigen presentation and/or an increasing expression of certain cytokines, chemokines and co-stimulatory markers.

The ability to induce or stimulate an anti-tau immune response upon administration in an animal or human organism can be evaluated either in vitro or in vivo using a variety of assays which are standard in the art. For a general description of techniques available to evaluate the onset and activation of an immune response, see for example Coligan et al. (1992 and 1994, Current Protocols in Immunology; ed. J Wiley & Sons Inc, National Institute of Health). Measurement of cellular immunity can be performed by methods readily known in the art, e.g., by measurement of cytokine profiles secreted by activated effector cells including those derived from CD4+ and CD8+ T-cells (e.g. quantification of IL-4 or IFN gamma-producing cells by ELISPOT), by determination of the activation status of immune effector cells (e.g. T-cell proliferation assays by a classical [3H] thymidine uptake), by assaying for antigen-specific T lymphocytes in a sensitized subject (e.g. peptide-specific lysis in a cytotoxicity assay, etc.).

The ability to stimulate a cellular and/or a humoral response can be determined by testing a biological sample (e.g., blood, plasma, serum, PBMCs, urine, saliva, feces, CSF or lymph fluid) from the subject for the presence of antibodies directed to the immunogenic tau peptide(s) administered in the pharmaceutical composition (see for example Harlow, 1989, Antibodies, Cold Spring Harbor Press). For example, titers of antibodies produced in response to administration of a composition providing an immunogen can be measured by enzyme-linked immunosorbent assay (ELISA), Meso scale Discovery (MSD), dot blots, SDS-PAGE gels, ELISPOT or Antibody-Dependent Cellular Phagocytosis (ADCP) Assay.

The invention provides a method of treating or preventing a neurodegenerative disease or disorder in a subject in need thereof using a liposomal vaccine containing tau peptides and a conjugate vaccine comprising tau peptides conjugated to an immunogenic carrier.

One of ordinary skill in the art will be able to vary the boosting compositions, the exact timing of the priming and boosting compositions, frequency of administration thereof, dosage thereof, etc., based upon the teachings herein and clinical experience.

Any of the primer and boosting compositions described herein can be used in a method for treating or preventing a neurodegenerative disease or disorder in a subject in need thereof. Embodiments of the priming composition; boosting composition; liposomes; and/or conjugates, etc. that can be used in the methods of the invention are discussed in detail above and in the illustrative examples below.

As used herein, the term "subject" refers to an animal. According to particular embodiments, the subject is a mammal including a non-primate (e.g., a camel, donkey, zebra, cow, pig, horse, goat, sheep, cat, dog, rat, rabbit, guinea pig or mouse) or a primate (e.g., a monkey, chimpanzee or human). According to particular embodiments, the subject is a human.

As used herein, the terms "treat", "treating", and "treatment" are all intended to refer to an amelioration or reversal of at least one measurable physical parameter related to a neurodegenerative disease, disorder, or condition, which is not necessarily discernible in the subject, but can be discernible in the subject. The terms "treat", "treating", and "treatment" can also refer to causing regression, preventing the progression, or at least slowing down the progression of the disease, disorder, or condition. In a particular embodiment, "treat", "treating", and "treatment" refer to an alleviation, prevention of the development or onset, or reduction in the duration of one or more symptoms associated with the neurodegenerative disease, disorder, or condition. In a particular embodiment, "treat", "treating", and "treatment" refer to prevention of the recurrence of the disease, disorder, or condition. In a particular embodiment, "treat", "treating", and "treatment" refer to an increase in the survival of a subject having the disease, disorder, or condition. In a particular embodiment, "treat", "treating", and "treatment" refer to elimination of the disease, disorder, or condition in the subject.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

As used herein a "neurodegenerative disease, disorder, or condition" includes any neurodegenerative disease, disorder, or condition known to those skilled in the art in view of the present disclosure. Examples of neurodegenerative diseases, disorders, or conditions include neurodegenerative diseases or disorders caused by or associated with the formation of neurofibrillary lesions, such as tau-associated diseases, disorders or conditions, referred to as tauopathies. According to particular embodiments, the neurodegenerative disease, disorder, or condition includes any of the diseases or disorders which show co-existence of tau and amyloid pathologies including, but not is limited to, Alzheimer's Disease, Parkinson's Disease, Creutzfeldt-Jacob disease, Dementia pugilistica, Down Syndrome, Gerstmann-Straussler-Scheinker disease, inclusion body myositis, prion protein cerebral amyloid angiopathy, traumatic brain injury, amyotrophic lateral sclerosis, parkinsonism-dementia complex of Guam, Non-Guamanian motor neuron disease with neurofibrillary tangles, argyrophilic grain dementia, corticobasal degeneration, Dementia Lewy Amyotrophic Lateral sclerosis, diffuse neurofibrillary tangles with calcification, frontotemporal dementia, preferably frontotemporal dementia with parkinsonism linked to chromosome 17 (FTDP-17), frontotemporal lobar dementia, Hallervorden-Spatz disease, multiple system atrophy, Niemann-Pick disease, type C, Pick's disease, progressive subcortical gliosis, progressive supranuclear palsy, Subacute sclerosing panencephalitis, Tangle only dementia, Postencephalitic Parkinsonism, Myotonic dystrophy, chronic traumatic encephalopathy (CTE), cerebral angiopathy or Lewy body dementia (LBD). According to particular embodiments, the neurodegenerative disease, disorder, or condition is Alzheimer's disease or another tauopathy.

The clinical course of Alzheimer's Disease can be divided into stages, with progressive patterns of cognitive and functional impairments. The stages can be defined using grading scales known in the art including, e.g., NIA-AA Research Framework. See, e.g., Dubois et al., *Alzheimer's & Dementia* 12 (2016) 292-323, Dubois et al., *Lancet Neurol* 2014; 13: 614-29, Jack et al., *Alzheimer's & Dementia* 14 (2018) 535-562, the content of each of which is hereby incorporated by references in its entirety.

According to preferred embodiments, the neurodegenerative disease, disorder, or condition is early Alzheimer's Disease, mild cognitive impairment (MCI) due to Alzheimer's Disease, mild Alzheimer's Disease, or mild to moderate Alzheimer's Disease.

In some embodiments, the subject in need of a treatment is amyloid positive in the brain but does not yet show significant cognitive impairment. The amyloid deposition in the brain can be detected using methods known in the art, such as PET scan, immunoprecipitation mass spectrometry or other methods.

The present invention also provides a method for promoting clearance of tau aggregates from the brain of a subject, said method comprising administering to the subject a pharmaceutical composition according to an embodiment of the invention, under conditions effective to promote clearance of the tau aggregates from the brain of the subject. According to particular embodiments, the tau aggregates are neurofibrillary tangles or their pathological tau precursors.

The present invention also provides a method for slowing progression of a tau-pathology related behavioral phenotype in a subject, said method comprising administering to the subject a pharmaceutical composition according to an embodiment of the invention, under conditions effective to slow the progression of the tau-pathology related behavioral phenotype in the subject.

In a preferred embodiment of the present invention, administration of a tau peptide, via administration of a pharmaceutical composition according to an embodiment of the invention, induces an active immune response in the subject to the tau peptide and to the pathological form of tau, thereby facilitating the clearance of related tau aggregates, slowing the progression of tau-pathology related behavior and/or treating the underlying tauopathy. In accordance with this aspect of the present invention, an immune response involves the development of a beneficial humoral (antibody mediated) response directed against the tau peptide and a cellular (mediated by antigen-specific T cells or their secretion products) response directed against the T-cell epitope or the immunogenic carrier.

As used herein, a tau-pathology related behavioral phenotype includes, without limitation, cognitive impairments, early personality change and disinhibition, apathy, abulia, mutism, apraxia, perseveration, stereotyped movements/behaviors, hyperorality, disorganization, inability to plan or organize sequential tasks, selfishness/callousness, antisocial traits, a lack of empathy, halting, agrammatic speech with frequent paraphasic errors but relatively preserved comprehension, impaired comprehension and word-finding deficits, slowly progressive gait instability, retropulsions, freezing, frequent falls, non-levodopa responsive axial rigidity, supranuclear gaze palsy, square wave jerks, slow vertical saccades, pseudobulbar palsy, limb apraxia, dystonia, cortical sensory loss, and tremor.

In carrying out the methods of the present invention, it is preferable to select a subject having or at risk of having Alzheimer's disease or other tauopathy, a subject having tau aggregates in the brain, or a subject exhibiting a tangle related behavioral phenotype prior to administering the immunogenic peptides or antibodies of the present invention. Subjects amenable to treatment include individuals at risk of disease but not showing symptoms, as well as patients presently showing symptoms. In the case of Alzheimer's disease, virtually anyone is at risk of suffering from Alzheimer's disease. Therefore, the present methods can be administered prophylactically to the general population without the need for any assessment of the risk of the subject patient. The present methods are especially useful for individuals who have a known genetic risk of Alzheimer's disease. Such individuals include those having relatives who have experienced the disease, and those whose risk is determined by analysis of genetic or biochemical markers.

In asymptomatic patients, treatment can begin at any age (e.g., 10, 20, 30 years of age). Usually, however, it is not necessary to begin treatment until a patient reaches 40, 50, 60, or 70 years of age. Treatment typically entails multiple dosages over a period of time. Treatment can be monitored by assaying antibody, or activated T-cell or B-cell responses to the therapeutic agent over time. If the response decreases, a booster dosage is indicated.

In prophylactic applications, pharmaceutical compositions containing the tau peptides are administered to a patient susceptible to, or otherwise at risk of, Alzheimer's disease or other tauopathy in an amount sufficient to eliminate or reduce the risk, lessen the severity, or delay the outset of the disease, including biochemical, histologic and/or behavioral symptoms of the disease, its complications and intermediate pathological phenotypes presented during development of the disease. In therapeutic applications, pharmaceutical compositions containing a tau peptide are administered to a patient suspected of, or already suffering from, such a disease in an amount sufficient to cure, or at least partially arrest, the symptoms of the disease (biochemical, histologic and/or behavioral), including its complications and intermediate pathological phenotypes in development of the disease.

Effective doses of a pharmaceutical composition of the invention, for the prevention and/or treatment of the neurodegenerative disease, disorder, or condition vary depending upon many different factors, including mode of administration, target site, physiological state of the patient, other medications administered, and whether treatment is prophylactic or therapeutic. The amount of a pharmaceutical composition depends on whether adjuvant is also administered, with higher dosages being required in the absence of adjuvant. In methods according to the invention, a subject is administered a priming composition at least once and a boosting composition at least once. The antigens in the respective priming and boosting compositions, however many boosting compositions are employed, need not be identical, but should share antigenic determinants or be substantially similar to each other.

It is readily appreciated by those skilled in the art that the regimen for the priming and boosting administrations can be adjusted based on the measured immune responses after the administrations. For example, the boosting compositions are generally administered weeks or months after administration of the priming composition, for example, about 2 weeks, or about 3 weeks or about 4 weeks, or about 8 weeks, or about 12 weeks, or about 16 weeks, or about 20 weeks, or about 24 weeks, or about 26 weeks, or about 28 weeks, or about 30 weeks or about 32 weeks or about 36 weeks or about one to two years after administration of the priming composition.

The pharmaceutical compositions can be administered by parenteral, topical, intravenous, oral, subcutaneous, intraarterial, intracranial, intraperitoneal, intradermal, intranasal, or intramuscular means for prophylactic and/or therapeutic treatment. The most typical route of administration of an immunogenic agent is subcutaneous or intramuscular injection. This latter type of injection is most typically performed in the arm or leg muscles.

The compositions can, if desired, be presented in a kit, pack or dispenser, which can contain one or more unit dosage forms containing the active ingredient. The kit, for example, can comprise metal or plastic foil, such as a blister pack. The kit, pack, or dispenser can be accompanied by instructions for administration.

According to particular embodiments, the kit comprises a pharmaceutical composition comprising a liposome according to an embodiment of the invention and a pharmaceutical composition comprising a conjugate according to an embodiment of the invention.

EMBODIMENTS

The invention provides also the following non-limiting embodiments.

Embodiment 1 is a method for inducing an immune response against a tau protein, preferably inducing antibodies against a tau phosphopeptide and/or ePHF in a subject suffering from a neurodegenerative disorder, the method comprising:

administering to the subject a priming composition comprising an immunologically effective amount of a liposome comprising:

a. a first tau peptide; and b. a helper T cell epitope;

wherein the tau peptide is presented on the surface of the liposome, and a pharmaceutically acceptable carrier; and administering to the subject a first boosting composition comprising an immunologically effective amount of a conjugate comprising a second tau phosphopeptide and an immunogenic carrier conjugated thereto via a linker, the conjugate having the structure of formula (I):

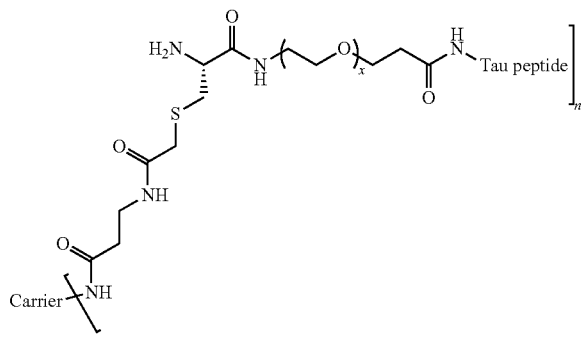

or having the structure of formula (II):

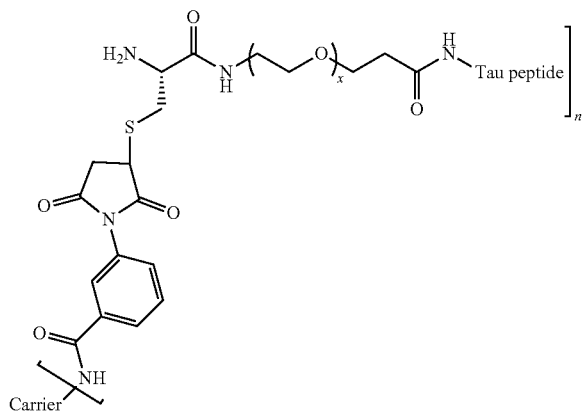

wherein
x is an integer of 0 to 10, preferably 2 to 6, most preferably 3; and
n is an integer of 3 to 15, preferably 3 to 12;
Carrier represents an immumogenic carrier; preferably the immunogenic carrier is selected from the group consisting of keyhole limpet hemocyanin (KLH), tetanus toxoid, CRM197 and an outer membrane protein mixture from *N. meningitidis* (OMP), or a derivative thereof; and
Tau peptide represents the second tau phosphopetide;
and the first boosting composition further comprises a pharmaceutically acceptable carrier.

Embodiment 2 is the method of Embodiment 1, wherein the tau peptide of the liposome is a tau phosphopeptide.

Embodiment 3 is the method of Embodiment 1 or 2, wherein the liposome further comprises a toll-like receptor ligand.

Embodiment 4 is the method of Embodiment 3, wherein the toll-like receptor ligand comprises at least one of a toll-like receptor 4 ligand and toll-like receptor 9 ligand.

Embodiment 5 is the method of Embodiment 3 or 4, wherein the toll-like receptor ligand is a toll-like receptor 4 ligand.

Embodiment 6 is the method of Embodiment 5, wherein the toll-like receptor 4 ligand comprises monophosphoryl lipid A (MPLA).

Embodiment 7 is the method of Embodiment 3 or 4, wherein the toll-like receptor ligand is a toll-like receptor 9 ligand.

Embodiment 8 is the method of Embodiment 7, wherein the toll-like receptor 9 ligand comprises a lipidated CpG oligonucleotide.

Embodiment 9 is the method of Embodiment 1, wherein the priming composition comprises an immunologically effective amount of a liposome comprising:
a. a tau peptide;
b. a helper T cell epitope; and
c. at least one of
i. a toll-like receptor 9 ligand, and
ii. a toll-like receptor 4 ligand.

Embodiment 10 is the method of Embodiment 9, wherein the tau peptide is a tau phosphopeptide.

Embodiment 11 is the method of Embodiment 9 or 10, wherein the toll-like receptor 9 ligand is a lipidated CpG oligonucleotide.

Embodiment 12 is the method of any of Embodiments 9 to 11, wherein the liposome comprises the toll-like receptor 4 ligand and toll-like receptor 9 ligand.

Embodiment 13 is the method of Embodiment 12, wherein the toll-like receptor 4 ligand comprises monophosphoryl lipid A (MPLA).

Embodiment 14 is the method of Embodiment 1, wherein the priming composition comprises an immunologically effective amount of a liposome comprising:
a tau phosphopeptide;
a helper T-cell epitope;
a lipidated CpG oligonucleotide; and
an adjuvant containing a toll-like receptor 4 ligand;
wherein the tau phosphopeptide is presented on the surface of the liposome.

Embodiment 15 is the method of Embodiment 14, wherein the toll-like receptor 4 ligand comprises monophosphoryl lipid A (MPLA).

Embodiment 16 is the method of any of Embodiments 1 to 15, wherein the helper T cell epitope is encapsulated in the liposome.

Embodiment 16a is the method of any of Embodiments 1 to 15, wherein the helper T cell epitope is incorporated in the membrane of the liposome.

Embodiment 16b is the method of any of Embodiments 1 to 15, wherein the helper T cell epitope is presented on the surface of the liposome.

Embodiment 17 is the method of Embodiments 1 to 16b, wherein the priming composition comprises an immunologically effective amount of a liposome composition comprising:
a tau phosphopeptide;
a helper T cell epitope;
a lipidated CpG oligonucleotide; and
a monophosphoryl lipid A (MPLA);
wherein the tau phosphopeptide is presented on the surface of the liposome, and
the T-cell epitope is encapsulated in the liposome.

Embodiment 17a is the method of Embodiment 17, wherein the MPLA is 3-O-desacyl-4'-monophosphoryl lipid A, preferably MPL™.

Embodiment 17b is the method of Embodiment 17, wherein the MPLA is monophosphoryl hexa-acyl lipid A, 3-deacyl, preferably 3D-(6-acyl) PHAD®).

Embodiment 17c is the method of Embodiment 17, wherein the MPLA is monophosphoryl 3-deacyl lipid A, preferably 3D-PHAD®.

Embodiment 18 is the method of any of Embodiments 1 to 17c, wherein the liposome composition of the priming composition further comprises one or more lipids selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol.

Embodiment 19 is the method of any of Embodiments 1 to 18, wherein the tau peptide of the liposome has an amino acid sequence selected from the group consisting of SEQ ID NO:1 to SEQ ID NO:12, or at least 85%, 90% or 95% identical to an amino acid sequence selected from the group consisting of SEQ ID NO:1 to SEQ ID NO:12.

Embodiment 19-1 is the method of Embodiment 19, wherein the tau peptide of the liposome is a phosphopeptide comprising an amino acid sequence selected from the group consisting of SEQ ID NOs: 1-3 and 5-12.

Embodiment 19-2 is the method of Embodiment 19-1, wherein the tau phosphopeptide of the liposome comprises the amino acid sequence of SEQ ID NO:1.

Embodiment 19-3 is the method of Embodiment 19-1, wherein the tau phosphopeptide of the liposome comprises the amino acid sequence of SEQ ID NO:2.

Embodiment 19-4 is the method of Embodiment 19-1, wherein the tau phosphopeptide of the liposome comprises the amino acid sequence of SEQ ID NO:3.

Embodiment 19a is the method of any one of Embodiments 19, 19-1, 19-2, 19-3 and 19-4, wherein the amino acid sequence further comprises one or more modifications to allow the tau peptide to be presented on the surface of the liposome.

Embodiment 19b is the method of Embodiment 19a, wherein the one or more modifications comprise at least one of palmitoylation and dodecyl modification.

Embodiment 19c is the method of Embodiment 19a or 19b, wherein the tau peptide of the liposome is modified at its N-terminus by the one or more modifications.

Embodiment 19d is the method of any of Embodiments 19a to 19c, wherein the tau peptide of the liposome is modified at its C-terminus by the one or more modifications.

Embodiment 19e is the method of Embodiment 19d, wherein the tau peptide of the liposome is palmitoylated at both of its N-terminus and C-terminus.

Embodiment 19f is the method of any of Embodiments 19a-19e, wherein the tau peptide of the liposome further comprises one or more additional amino acids to facilitate the one or more modifications.

Embodiment 19g is the method of Embodiment 19f, wherein the one or more additional amino acids are selected from the group consisting of Lys, Cys, Ser and Thr.

Embodiment 19h is the method of any of Embodiments 19 to 19g, wherein the tau peptide of the liposome is amidated at its C-terminus.

Embodiment 19i is the method of any of Embodiments 19 to 19h, wherein the tau peptide of the liposome consists of an amino acid sequence selected from the group consisting of SEQ ID NO:27 to SEQ ID NO:38.

Embodiment 19j is the method of any of Embodiments 19-19i, wherein the tau peptide of the liposome consists of the amino acid sequence of SEQ ID NO:27.

Embodiment 19k is the method of any of Embodiments 19-19i, wherein the tau peptide of the liposome consists of the amino acid sequence of SEQ ID NO:28.

Embodiment 19l is the method of any of Embodiments 19-19i, wherein the tau peptide of the liposome consists of the amino acid sequence of SEQ ID NO:29.

Embodiment 20 is the method of any of Embodiments 1 to 19l, wherein the helper T cell epitope of the liposome comprises at least one amino acid sequence selected from the group consisting of: SEQ ID NO:23 to SEQ ID NO:26.

Embodiment 20a is the method of Embodiment 20, wherein helper T cell epitope comprises at least two amino acid sequences selected from the group consisting of: SEQ ID NO:23 to SEQ ID NO:26.

Embodiment 20b is the method of Embodiment 20, wherein helper T cell epitope comprises at least three amino acid sequences selected from the group consisting of: SEQ ID NO:23 to SEQ ID NO:26.

Embodiment 20c is the method of Embodiment 20, wherein helper T cell epitope comprises the four amino acid sequences of: SEQ ID NO:23 to SEQ ID NO:26.

Embodiment 20d is the method of any of Embodiments 20a to 20c, wherein the two or more amino acid sequences selected from the group consisting of SEQ ID NO:23 to SEQ ID NO:26 are covalently linked by a linker.

Embodiment 20e is the method of Embodiment 20d, wherein the linker comprises one or more amino acids selected from the group consisting of Val (V), Ala (A), Arg (R), Gly (G), Ser (S), Lys (K).

Embodiment 20f is the method of Embodiment 20e, wherein the linker comprises an amino acid sequence selected from the group consisting of VVR, GS, RR and RK.

Embodiment 20g is the method of any of Embodiments 20 to 20f, wherein the helper T cell epitope is amidated at its C-terminus.

Embodiment 20h is the method of any of Embodiments 20 to 20g, wherein the helper T cell epitope is modified for insertion into the membrane of the liposome, presentation on the surface of the liposome or encapsulation in the liposome, depending on the intended location of the helper T cell epitope.

Embodiment 20i is the method of any of Embodiments 20 to 20h, wherein the helper T cell epitope consisting of an amino acid sequence selected from the group consisting of SEQ ID NO:13 to SEQ ID NO:17.

Embodiment 20j is the method of any of Embodiments 1 to 20i, wherein liposome comprises the tau peptide and the helper T cell epitope at a weight ratio of 6:1.

Embodiment 20k is the method of any of Embodiments 1 to 20i, wherein liposome comprises the tau peptide and the helper T cell epitope at a weight ratio of 5:1.

Embodiment 20l is the method of any of Embodiments 1 to 20i, wherein liposome comprises the tau peptide and the helper T cell epitope at a weight ratio of 4:1.

Embodiment 20m is the method of any of Embodiments 1 to 20i, wherein liposome comprises the tau peptide and the helper T cell epitope at a weight ratio of 3:1.

Embodiment 20n is the method of any of Embodiments 1 to 20i, wherein liposome comprises the tau peptide and the helper T cell epitope at a weight ratio of 2:1.

Embodiment 20o is the method of any of Embodiments 1 to 20i, wherein liposome comprises the tau peptide and the helper T cell epitope at a weight ratio of 1:1.

Embodiment 21 is the method of any of Embodiments 1 to 20o, wherein the lipidated CpG oligonucleotide comprises the nucleotide sequence selected from the group consisting of SEQ ID NO:18 to SEQ ID NO:22.

Embodiment 21a is the method of Embodiment 21, wherein the CpG oligonucleotide has one or more phosphorothioate internucleotide linkages.

Embodiment 21b is the method of Embodiment 21a, wherein the CpG oligonucleotide has all phosphorothioate internucleotide linkages.

Embodiment 21c is the method of any of Embodiments 21 to 21b, wherein lipidated CpG oligonucleotide comprises the CpG oligonucleotide covalently linked to at least one lipophilic group via a linker.

Embodiment 21d is the method of Embodiment 21c, wherein the linker comprises ($C_2H_4O$)n, wherein n is an integer of 0 to 10.

Embodiment 21e is the method of Embodiment 21c, wherein the linker comprises an alkyl spacer having 3 to 12 carbons.

Embodiment 21f is the method of any of Embodiment 21 to 21e, wherein the at least one lipophilic group is cholesterol.

Embodiment 21g is the method of any of Embodiment 21 to 21f, wherein the lipidated CpG oligonucleotide comprises the nucleotide sequence of SEQ ID NO:18 or SEQ ID NO:19 covalently linked to a cholesterol molecule via a linker comprising ($C_2H_4O$)n, wherein n is an integer of 3 to 5.

Embodiment 22 is a method for inducing an immune response against a tau protein in a subject suffering from a neurodegenerative disorder, the method comprising:

administering to the subject a priming composition comprising an immunologically effective amount of a liposome comprising:
- a first tau phosphopeptide having an amino acid sequence selected from the group consisting of SEQ ID NO: 27 to SEQ ID NO: 29 and SEQ ID NO: 31 to SEQ ID NO: 38;
- a helper T cell epitope having an amino acid sequence selected from the group consisting of SEQ ID NO:39 to SEQ ID NO:44, preferably, the helper T cell epitope consisting of an amino acid sequence selected from the group consisting of SEQ ID NO:13 to SEQ ID NO:17;
- a lipidated CpG oligonucleotide having a nucleotide sequence selected from the group consisting of SEQ ID NO:18 to SEQ ID NO:22, wherein the CpG oligonucleotide comprises one or more phosphorothioate internucleotide linkages, and the CpG oligonucleotide is covalently linked to at least one cholesterol via a linker; and monophosphoryl lipid A (MPLA), and a pharmaceutically acceptable carrier; and administering to the subject a first boosting composition comprising an immunologically effective amount of a conjugate comprising a second tau phosphopeptide and an immunogenic carrier conjugated thereto via a linker, the conjugate having the structure of formula (I):

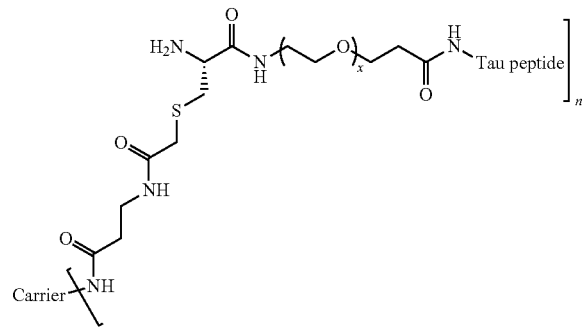

or having the structure of formula (II):

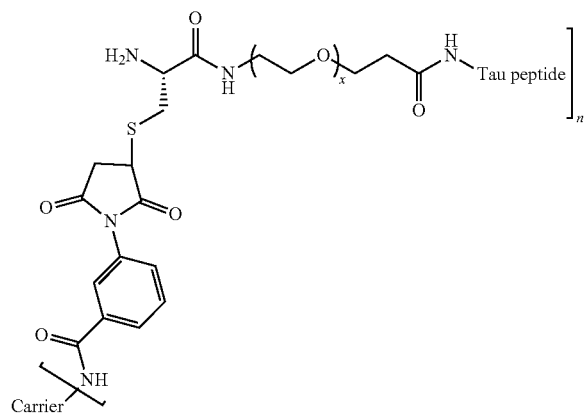

wherein
x is an integer of 0 to 10, preferably 2 to 6, most preferably 3; and
n is an integer of 3 to 15, preferably 3 to 12;
Carrier represents the immunogenic carrier;
Tau peptide represents the second tau phosphopeptide;
and a pharmaceutically acceptable carrier.

Embodiment 22a is a method of Embodiment 22, wherein the liposome comprises:
a. a first tau phosphopeptide consisting of the amino acid sequence of SEQ ID NO:27, SEQ ID NO:28 or SEQ ID NO:29;
b. a helper T cell epitope consisting of the amino acid sequence of SEQ ID NO:13
c. a lipidated CpG oligonucleotide consisting of the nucleotide sequence of SEQ ID NO: 18 or SEQ ID NO:19 covalently linked to a cholesterol via a linker comprising (C2H4O)n, wherein n is an integer of 3 to 7; and
d. monophosphoryl lipid A (MPLA).

Embodiment 22b is the method of Embodiment 22 or 22a, wherein the MPLA is 3-O-desacyl-4'-monophosphoryl lipid A, preferably MPL™.

Embodiment 22c is the method of Embodiment 22 or 22a, wherein the MPLA is monophosphoryl hexa-acyl lipid A, 3-deacyl, preferably 3D-(6-acyl) PHAD®).

Embodiment 22d is the method of Embodiment 22 or 22a, wherein the MPLA is monophosphoryl 3-deacyl lipid A, preferably 3D-PHAD®.

Embodiment 23 is the method of any one of Embodiments 22 to 22d, wherein the helper T cell epitope is encapsulated in the liposome.

Embodiment 24 is the method of any one of Embodiments 1 to 23, wherein x is an integer of 2 to 6.

Embodiment 25 is the method of any one of Embodiments 1 to 24, wherein x is 3.

Embodiment 26 is the method of any of Embodiments 1 to 25, wherein n is 3 to 7.

Embodiment 27 is the method of any of Embodiments 1 to 26, wherein the carrier is an immunogenic carrier selected from the group consisting of keyhole limpet hemocyanin (KLH), tetanus toxoid, CRM197, and an outer membrane protein mixture from *N. meningitidis* (OMP), or a derivative thereof.

Embodiment 28 is the method of any of Embodiments 1 to 27, wherein the second tau phosphopeptide of the conjugate consists of the amino acid sequence selected from the group consisting of SEQ ID NO: 1 to SEQ ID NO: 3 and SEQ ID NO: 5 to SEQ ID NO: 12.

Embodiment 28a is the method of Embodiment 28, wherein the first tau phosphopeptide of the liposome and the second tau phosphopeptide of the conjugate are identical.

Embodiment 28b is the method of Embodiment 28, wherein the first tau phosphopeptide of the liposome and the second tau phosphopeptide of the conjugate are different.

Embodiment 28c is the method of Embodiment 28b, wherein the first tau phosphopeptide of the liposome and the second tau phosphopeptide of the conjugate share at least one common epitope.

Embodiment 29 is the method of any one of Embodiments 28-28c, wherein the second tau phosphopeptide consists of the amino acid sequence of SEQ ID NO:1, SEQ ID NO:2 or SEQ ID NO:3.

Embodiment 30 is the method of any of Embodiments 1 to 29, wherein the carrier is CRM197.

Embodiment 31 is the method of any one of Embodiments 1-30, wherein the conjugate has the structure of:

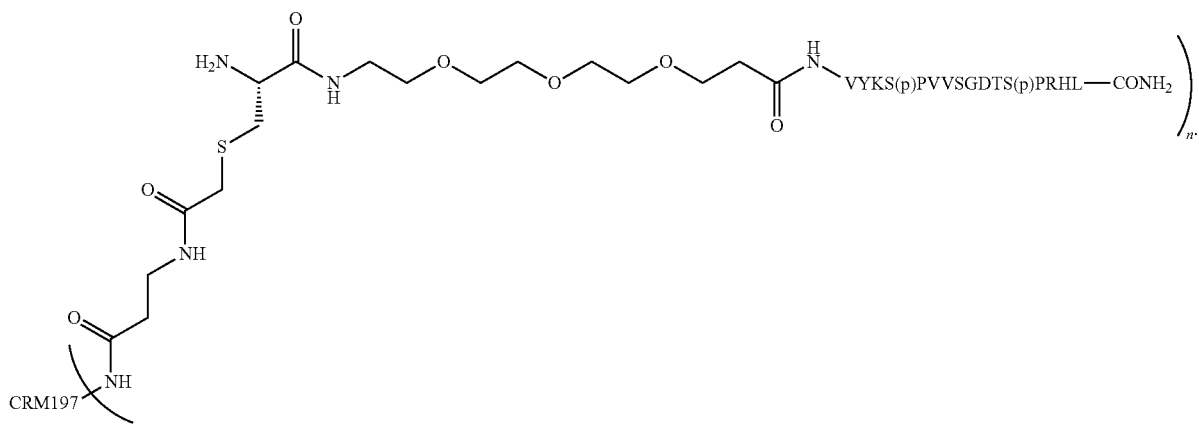

wherein n is 3-7 and VYKS(p)PVVSGDTS(p)PRHL-CONH₂ comprises the phospho-tau peptide of SEQ ID NO:2.

Embodiment 32 is the conjugate of any one of Embodiments 1-29, wherein the conjugate has the structure of:

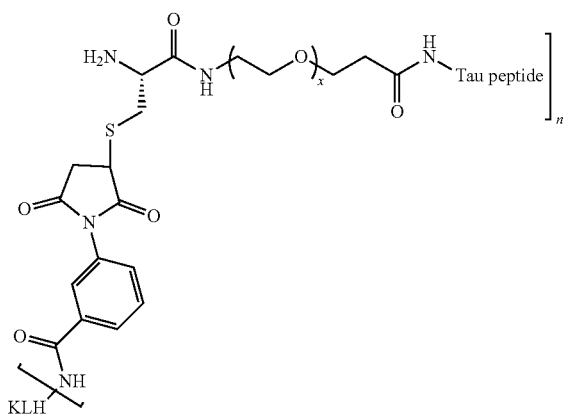

wherein
the Tau peptide consisting of SEQ ID NO:1, SEQ ID NO: 2 or SEQ ID NO:3;
x is an integer of 0 to 10;
n is an integer of 2 to 15;
Tau peptide represents a tau phosphopeptide; and
KLH represents keyhole limpet hemocyanin.

Embodiment 33 is the method of any of Embodiments 1 to 32, further comprising administering to the subject a second boosting composition comprising an immunogenic effective amount of the liposome.

Embodiment 33a is the method of Embodiment 33, wherein the priming composition, the first boosting composition and/or the second boosting composition further comprises an adjuvant.

Embodiment 33b is the method of embodiment 33a, wherein the adjuvant comprises at least one of a TLR-4 ligand and a TLR-9 ligand.

Embodiment 34 is the method of any of Embodiments 1 to 33b, wherein the first boosting composition is administered at about 27-32 days, preferably at about 29 days after the priming composition is initially administered.

Embodiment 35 is the method of Embodiment 34, further comprising re-administering the first boosting composition at about 82-87 days, preferably at about 85 days after the priming composition is initially administered.

Embodiment 36 is the method of Embodiment 35, further comprising administering the second boosting composition at about 167-172 days, preferably at about 169 days after the priming composition is initially administered.

Embodiment 37 is the method of any of Embodiments 1 to 33b, wherein the first boosting composition is administered at about 82-87 days, preferably at about 85 days after the priming composition is initially administered.

Embodiment 38 is the method of Embodiment 37, further comprising administering the second boosting composition at about 27-32 days, preferably at about 29 days after the priming composition is initially administered.

Embodiment 39 is the method of Embodiment 35, further comprising re-administering the first boosting composition at about 167-172 days, preferably at about 169 days after the priming composition is initially administered.

Embodiment 40 is a method for treating or preventing a neurodegenerative disease or disorder in a subject in need thereof, comprising:
administering to the subject a priming composition comprising an immunologically effective amount of a liposome comprising:
a first tau phosphopeptide having an amino acid sequence selected from the group consisting of SEQ ID NO: 27 to SEQ ID NO: 29 and SEQ ID NO: 31 to SEQ ID NO: 38;
a helper T cell epitope having an amino acid sequence selected from the group consisting of SEQ ID NO: 39 to SEQ ID NO: 44, preferably, the helper T cell epitope consisting of an amino acid sequence selected from the group consisting of SEQ ID NO: 13 to SEQ ID NO: 17;
a lipidated CpG oligonucleotide having a nucleotide sequence selected from the group consisting of SEQ ID NO: 18 to SEQ ID NO: 22, wherein the CpG oligonucleotide comprises one or more phosphorothioate internucleotide linkages, and the CpG oligonucleotide is covalently linked to at least one cholesterol via a linker; and
monophosphoryl lipid A (MPLA);
wherein the tau phosphopeptide is presented on the surface of the liposome,
and a pharmaceutically acceptable carrier; and
administering to the subject a first boosting composition comprising an immunologically effective amount of a conjugate comprising a tau phosphopeptide and an immunogenic carrier conjugated thereto via a linker, the conjugate having the structure of:

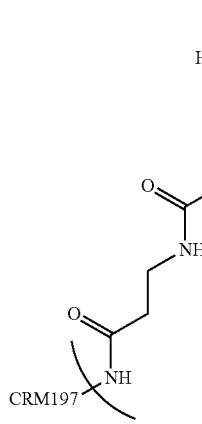
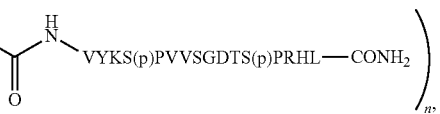

wherein n is an integer of 3 to 7 and VYKS(p)PVVSGDTS (p)PRHL-CONH₂ comprises the phospho-tau peptide of SEQ ID NO:2, and a pharmaceutically acceptable carrier.

Embodiment 41 is the method of Embodiment 40, wherein the first boosting composition is administered at about 27-32 days, preferably at about 29 days after the priming composition is initially administered.

Embodiment 42 is the method of Embodiment 41, further comprising re-administering the first boosting composition at about 82-87 days, preferably at about 85 days after the priming composition is initially administered.

Embodiment 43 is the method of Embodiment 42, further comprising administering a second boosting composition comprising an immunogenic effective amount of the liposome at about 167-172 days, preferably at about 169 days after the priming composition is initially administered.

Embodiment 44 is the method of Embodiment 40, wherein the first boosting composition is administered at about 82-87 days, preferably at about 85 days after the priming composition is initially administered.

Embodiment 45 is the method of Embodiment 44, further comprising administering a second boosting composition comprising an immunogenic effective amount of the liposome at about 27-32 days, preferably at about 29 days after the priming composition is initially administered.

Embodiment 46 is the method of Embodiment 45, further comprising re-administering the first boosting composition at about 167-172 days, preferably at about 169 days after the priming composition is initially administered.

Embodiment 46a is the method of any one of Embodiments 1 to 46, wherein the immunologically effective amount of the conjugate is administered together with one or more adjuvants.

Embodiment 46b is the method of embodiment 46a, wherein the adjuvant comprises an aluminum salt, such as aluminum hydroxide, aluminum phosphate, and aluminum sulfate.

Embodiment 46c is the method of embodiment 46a or 46b, wherein the adjuvant comprises a CpG, such as CpG2006 (also known as CpG 7909), CpG 1018, CpG2395, CpG2216, CpG1826 or CpG2336.

Embodiment 46d is the method of embodiment 46c, wherein the immunologically effective amount of the conjugate is administered together with an aluminum salt, such as aluminum hydroxide, aluminum phosphate, and aluminum sulfate, and a CpG, such as CpG2006 (also known as CpG 7909), CpG 1018, CpG2395, CpG2216, CpG1826 or CpG2336.

Embodiment 46e is the method of embodiment 46d, wherein the immunologically effective amount of the conjugate is administered together with aluminum phosphate and CpG 1018.

Embodiment 46f is the method of embodiment 46d, wherein the immunologically effective amount of the conjugate is administered together with aluminum hydroxide and CpG 7909.

Embodiment 46g is the method of embodiment 46d, wherein the immunologically effective amount of the conjugate is administered together with aluminum sulfate and CpG 2395.

Embodiment 46h is the method of embodiment 46d, wherein the immunologically effective amount of the conjugate is administered together with aluminum hydroxide and CpG1826.

Embodiment 47 is the method of any of Embodiments 1 to 46h, wherein the neurodegenerative disease or disorder is caused by or associated with the formation of neurofibrillary lesions.

Embodiment 48 is the method of any of Embodiments 1 to 47, wherein the neurodegenerative disease or disorder is Alzheimer's Disease, Parkinson's Disease, Creutzfeldt-Jacob disease, Dementia pugilistica, Down Syndrome, Gerstmann-Straussler-Scheinker disease, inclusion body myositis, prion protein cerebral amyloid angiopathy, traumatic brain injury, amyotrophic lateral sclerosis, parkinsonism-dementia complex of Guam, Non-Guamanian motor neuron disease with neurofibrillary tangles, argyrophilic grain dementia, corticobasal degeneration, Dementia Lewy Amyotrophic Lateral sclerosis, diffuse neurofibrillary tangles with calcification, frontotemporal dementia, preferably frontotemporal dementia with parkinsonism linked to chromosome 17 (FTDP-17), frontotemporal lobar dementia, Hallervorden-Spatz disease, multiple system atrophy, Niemann-Pick disease, type C, Pick's disease, progressive subcortical gliosis, progressive supranuclear palsy, Subacute sclerosing panencephalitis, Tangle only dementia, Postencephalitic Parkinsonism, Myotonic dystrophy, chronic traumatic encephalopathy (CTE), Cerebral angiopathy or Lewy body dementia (LBD).

Embodiment 49 is the method of any of Embodiments 1 to 48, wherein the neurodegenerative disease or disorder is Alzheimer's disease, Parkinson's Disease, Down Syndrome, progressive supranuclear palsy (PSP), frontotemporal dementia and parkinsonism linked to chromosome 17 (FTDP-17), Pick's disease and PART (primary age-related tauopathy), Corticobasal Degeneration, Dementia Lewy Amyotrophic Lateral sclerosis, Myotonic dysphagia, chronic traumatic encephalopathy (CTE), Cerebral angiopathy, or Lewy body dementia (LBD).

Embodiment 50 is the method of any of Embodiments 1 to 49, wherein the neurodegenerative disease or disorder is Alzheimer's disease, progressive supranuclear palsy (PSP), frontotemporal dementia and parkinsonism linked to chromosome 17 (FTDP-17), or Pick's disease and PART (primary age-related tauopathy).

Embodiment 51 is the method of any of Embodiments 1 to 50, wherein the neurodegenerative disease or disorder is Alzheimer's disease, Parkinson's Disease, Down Syndrome, frontotemporal dementia and parkinsonism linked to chromosome 17 (FTDP-17), Corticobasal Degeneration, Dementia Lewy Amyotrophic Lateral sclerosis, Myotonic dysphagia, chronic traumatic encephalopathy (CTE), Cerebral angiopathy, or Lewy body dementia (LBD).

Embodiment 51a is the method of any of Embodiments 1 to 51, wherein the neurodegenerative disease or disorder is early Alzheimer's Disease, mild cognitive impairment (MCI) due to Alzheimer's Disease, mild Alzheimer's Disease or mild to moderate Alzheimer's Disease.

Embodiment 52 is a combination, such as a kit, comprising the priming composition and the first boosting composition used in any of embodiments 1 to 51a.

Embodiment 53 is the method of any one of Embodiments 1 to 51a, or the combination of Embodiment 52, wherein the immunologically effective amount of the liposome contains about 25 nmoles to about 750 nmoles per dose, preferably about 90 nmoles to about 715 nmoles per dose or about 90 nmoles to about 535 nmoles per dose, such as about 25 nmoles, about 30 nmoles, about 35 nmoles, about 40 nmoles, about 45 nmoles, about 50 nmoles, about 55 nmoles, about 60 nmoles, about 65 nmoles, about 70 nmoles, about 75 nmoles, about 80 nmoles, about 85 nmoles, about 90 nmoles, about 95 nmoles, about 100 nmoles, about 125 nmoles, about 150 nmoles, about 175 nmoles, about 200 nmoles, about 225 nmoles, about 250 nmoles, about 275 nmoles, about 300 nmoles, about 325 nmoles, about 350 nmoles, about 375 nmoles, about 400 nmoles, about 425 nmoles, about 450 nmoles, about 475 nmoles, about 500 nmoles, about 525 nmoles, about 550 nmoles, about 575 nmoles, about 600 nmoles, about 625 nmoles, about 650 nmoles, about 675 nmoles, about 700 nmoles, about 725 nmoles, about 750 nmoles, or any value in between, per dose, of the first tau phosphopeptide.

Embodiment 53a is the method of any one of Embodiments 1 to 51a, or the combination of Embodiment 52, wherein the immunologically effective amount of the liposome contains about 25 nmoles to about 750 nmoles per dose, such as about 29.7 nmoles to about 742.5 nmoles per dose, preferably about 90 nmoles to about 715 nmoles per dose, such as about 89.1 nmoles to about 712.8 nmoles per dose, or about 90 nmoles to about 535 nmoles per dose, such as about 89.1 nmoles to about 534.6 nmoles per dose, or about 90 nmoles to about 268 nmoles per dose, such as about 89.1 nmoles to about 267.3 nmoles per dose, of the first tau phosphopeptide.

Embodiment 53b is the method or combination of Embodiment 53 or 53a, wherein the immunologically effective amount of the liposome contains about 100 μg to about 2500 μg, preferably about 300 μg to about 2400 μg, such as about 100 μg, about 150 μg, about 200 μg, about 250 μg, about 300 μg, about 400 μg, about 500 μg, about 600 μg, about 700 μg, about 800 μg, about 900 μg, about 1000 μg, about 1100 μg, about 1200 μg, about 1300 μg, about 1400 μg, about 1500 μg, about 1600 μg, about 1700 μg, about 1800 μg, about 1900 μg, about 2000 μg, about 2100 μg, about 2200 μg, about 2300 μg, about 2400 μg, about 2500 μg, or any value in between, per dose, of the first tau phosphopeptide.

Embodiment 53c is the method or combination of any one of Embodiments 53 to 53b, wherein the first tau phosphopeptide consists of the amino acid sequence of one of SEQ ID NO:27 to SEQ ID NO:38.

Embodiment 53d is the method or combination of Embodiment 53c, wherein the first tau phosphopeptide consists of the amino acid sequence of SEQ ID NO: 28.

Embodiment 54 is the method or combination of any one of Embodiments 53 to 53d, wherein the second tau phosphopeptide consists of the amino acid sequence of SEQ ID NOs: 1-3 or 5-12.

Embodiment 54a is the method or combination of Embodiment 54, wherein the second tau phosphopeptide consists of the amino acid sequence of SEQ ID NO: 1, 2, or 3.

EXAMPLES

Example 1

Preparation of Liposomal Vaccines

Preparation of the Control Liposomal Vaccine (Ethanol Injection Technique)

The control liposomal vaccine was produced by Ethanol (EtOH) Injection technique followed by extrusion. First, DMPC (Lipoid GmbH, Ludwigshafen, Germany), DMPG (Lipoid GmbH, Ludwigshafen, Germany), cholesterol (Dishman, Netherlands) and MPLA (Avanti Polar Lipids, AL, USA) were solubilized at a molar ratio of 9:1:7:0.05 in a 20:1 (V/V) mixture of EtOH and tert-butanol (t-BuOH) at 60° C. The lipid/ethanol solution was diluted in phosphate buffer saline (PBS) pH 7.4 at 60° C. to maintain 10% EtOH concentration and resulting in the formation of multilamellar liposome vesicles (MLVs). The MLVs were then submitted to 5 sequential passes of extrusion through three polycarbonate filters (Whatman) with a pore size of 0.08 μm in series using Emulsiflex-C5 (Avestin, Canada). The resulting liposomes were diluted in PBS pH 7.4 and heated to 60° C. to obtain a liposome solution prior to tau peptide addition.

An acetate tetrapalmitoylated phosphorylated tau peptide of SEQ ID NO: 2 (Bachem AG, Switzerland), corresponding to SEQ ID NO:28, herein referred to as the active pharmaceutical ingredient (API), was dissolved in PBS at pH 11.4 with 2.0% octyl P-D-glucopyranoside (Sigma-Aldrich, USA) at a concentration of 1 mg/mL, and the peptide solution was injected into the liposome solution at 60° C. followed by stirring for 30 minutes at 60° C. Concentration was done through ultrafiltration to a target final volume, and buffer exchange was carried out 10 times with PBS pH 7.4 during diafiltration. The resulting liposomes, with the API presented on the surface of the liposomes, were then sterile filtered by passing through two 0.2 μm polycarbonate syringe filters in series, and the final product was stored at 5° C.

Preparation of the Liposome Z and Z+ Vaccines

The Liposome Z+ vaccines, with a final API concentration of 1200 μg/ml and final T50 concentration of 1200 μg/ml were produced by Ethanol Injection technique followed by extrusion and the liposome Z vaccines, with a final API concentration of 400 μg/ml and final T50 concentration of 100 µg/ml, were produced by thin-lipids film technology followed by homogenization and extrusion.

Preparation of Liposome Z Vaccine by Thin Lipid Film Technique

The Liposome Z vaccine was produced by thin-lipids film technology followed by homogenization and extrusion. First, DMPC (Lipoid GmbH, Ludwigshafen, Germany), DMPG (Lipoid GmbH, Ludwigshafen, Germany), cholesterol (Dishman, Netherlands) and monophosphoryl hexaacyl Lipid A 3-deacyl synthetic (3D-(6-acyl) PHAD®) (Avanti Polar Lipids, AL, USA) were solubilized at a molar ratio of 9:1:7:0.05 in EtOH at 60° C. Ethanol was evaporated under vacuum rotavapor to obtain thin lipid film.

Lipid film was rehydrated with PBS pH 7.4, 5% DMSO (all Sigma-Aldrich) containing 0.15 mg/mL T50 peptide (Peptides & Elephants, Germany). The sample was gently stirred for 15 min and was further vigorously vortexed to dissolve the thin lipid film. Resulting multilamellar vesicles were subjected to 10 freeze-thaw cycles (liquid N2 and waterbath at 37° C.) and submitted to homogenization followed by sequential extrusion through polycarbonate membranes (Whatman, UK) with a pore size of 0.08 µm. Both the homogenization and extrusion steps were done in an EmulsiFlex-C5 (Avestin, Canada). Extruded liposomes with encapsulated T50 peptide were concentrated by ultrafiltration, and buffer was exchanged to PBS pH 7.4 by diafiltration. The resulting liposomes were diluted in PBS pH 7.4 and heated to 60° C. to obtain a liposome solution prior to tau peptide and adjuvant addition.

CpG2006-Cholesterol (CpG2006-Chol) (Microsynth, Switzerland) is a DNA oligonucleotide with all internucleotide linkages as thiophosphate that is modified at 5' terminus with a Cholesterol molecule through a phosphate bond by means of a PEG spacer. CpG2006-Cholesterol (CpG2006-Chol) (Microsynth, Switzerland) was dissolved in PBS pH 7.4 at 1 mg/mL and injected into the liposome solutions followed by incubation for 15 minutes before insertion of the API.

The API (Bachem AG, Switzerland) was dissolved in PBS pH 11.4 with 2% Octyl B-D-glucopyranoside (Sigma-Aldrich, USA) at a concentration of 1 mg/mL, and the peptide solution was injected into the liposome solution at 60° C. followed by stirring for 30 min at 60° C. Concentration was done through ultrafiltration to obtain the target value (400 µg/ml API and 100 µg/ml T50 for liposome Z), and buffer exchange was carried out 10 times with PBS pH 7.4 during diafiltration. The resulting liposomes with the API presented on the surface of the liposomes were then sterile filtered by passing through 0.2 µm polycarbonate syringe filters, and the final product was stored at 5° C.

Preparation of Liposome Z+ Vaccine by Ethanol Injection

The Liposome Z+ vaccine was produced using an ethanol injection based process. First, DMPC (Lipoid GmbH, Ludwigshafen, Germany), DMPG (Lipoid GmbH, Ludwigshafen, Germany), cholesterol (Dishman, Netherlands) and 3D-(6-acyl) PHAD® (Avanti Polar Lipids, AL, USA) were solubilized at a molar ratio of approximately 9:1:7:0.04 in EtOH at 60° C. T50 peptide (Bachem AG, Switzerland) was dissolved in 10 mM His/270 mM sucrose (pH 5.8-6.0). Then, the lipid ethanol solution was injected into the solution containing T50 peptide and gently stirred for 15 min, resulting in multilamellar vesicles (MLVs). MLVs were submitted to homogenization (6 times for Liposome Z+) followed by sequential extrusion through polycarbonate membranes (Whatman, UK) with a pore size of 0.08 µm (5 passes for Liposome Z+). Both the homogenization and extrusion steps were done in an EmulsiFlex-C5 (Avestin, Canada) for Liposome Z+. Extruded liposomes were concentrated by ultrafiltration, and buffer was exchanged to 20 mM His/145 mM NaCL pH 7.4 by diafiltration. The resulting liposomes with encapsulated T50 peptide were diluted in 20 mM His/145 mM NaCL pH 7.4 and heated to 60° C. to obtain a liposome solution prior to the additions of the API and the adjuvant.

CpG2006-Chol (Microsynth, Switzerland for Liposome Z+) was dissolved in 20 mM His/145 mM NaCl pH 7.4 at 1 mg/mL and injected into the liposome solution followed by incubation for 15 minutes before insertion of the API.

The API (Bachem AG, Switzerland) was dissolved in carbonate buffer pH 10.2 with 1% Octyl B-D-glucopyranoside (Sigma-Aldrich, USA), at a concentration of 1 mg/mL, and the peptide solution was injected into the liposome Z+ solution at 60° C. followed by stirring for 30 min at 60° C. The peptide solution was mixed into the liposome Z+ solution using T-Line Mixing at 60° C. followed by stirring for 30 min at 60° C. Concentration was done through ultrafiltration to obtain the target value (1200 µg/ml API and 1200 µg/ml T50 for Liposome Z+), and buffer exchange was carried out 10 times with 10 mM His/270 mM Sucrose pH 6.5 during diafiltration. The resulting Z+ liposomes with the API presented on the surface of the liposomes were then sterile filtered by passing through 0.2 µm polycarbonate syringe/capsule filters, and the final product was stored at 5° C.

Example 2

Preparation of Conjugate Vaccine

Peptides and Adjuvants

Phosphorylated tau peptides (SEQ ID NO: 2) used in this study were produced synthetically (Pepscan, NL) with the phospho-residues added during synthesis. A conjugate comprising a phosphorylated tau peptide having the amino acid sequence of SEQ ID NO: 2 covalently linked to a CRM carrier via a linker is herein referred to as Conjugate X.

Vaccine peptides were conjugated to the carrier protein CRM197 via a polyethylene glycol (PEG)-cysteine-acetamidopropionamide linker. Phosphorylated tau peptide having the amino acid sequence of SEQ ID NO: 2 was produced synthetically (Polypeptide Laboratories SAS), with phospho-residues and PEG3 spacer added during synthesis. Conjugate X was manufactured by conjugating the carrier protein CRM197 via a succinimidyl 3-(bromoacetamide) propionate (SBAP) linker to a cysteine on the N-terminus of the peptide. SBAP was ligated to CRM197 protein primary amines (—NH2) via NHS ester reaction chemistry. The excess SBAP linker was removed using ultrafiltration and diafiltration (UF/DF). The CRM197-SBAP intermediate was conjugated to the phosphorylated tau peptide, and once the reaction was completed, the conjugation reaction was terminated by adding excess amount of L-cystine to quench the reaction. The crude CRM197-peptide conjugated product was purified using a Capto Q ImpRes (GE Healthcare) chromatography column and eluted using a salt isocratic method. The purified CRM197-peptide product was then formulated into a buffer containing Tris and sucrose, such as 20 mM Tris, 250 mM Sucrose, at pH 8.1 using UF/DF. The CRM197-tau peptide Drug Substance (DS) stock solution was generated by adding polysorbate 80 (PS80) stock buffer, such as a 10% PS80 stock buffer to reach a final concentration of 0.01% PS80. The solution was thoroughly mixed prior to filtering. Prior to injection, the stock solution was diluted with PBS and CpG/Alum, e.g., to a first concentration of 0.8 mg/mL CRM197-tau peptide, and then further diluted with PBS and CpG/Alum to a final concentration of 30 ug/mL of CRM197-tau peptide for injection. For Examples 3 to 7, CRM197-tau peptide stock solution was kept at a concentration of 3.1 mg/mL in 10 mM PBS (pH 7.3) and was further diluted in PBS to reach the desired working concentration. CpG oligonucleotide, alum and PBS were then added to reach a final concentration of 30 ug/mL based on CRM197-tau peptide and the final formulation was thoroughly mixed before injection.

One concern in targeting a CNS antigen with an active vaccine is that non-specific or off-target inflammation might cause unwanted neuropathological changes. To investigate this, whole brains from mice immunized with a conjugate composition were collected and stained to visualize perivascular or other cellular infiltrates. None of the immunized animals had any sign of neuroinflammation, cellular infiltration, or other undesirable neuropathological changes (data not shown). This suggested that the vaccine-induced antibodies, and the innate immune response to vaccination, did not cause neuropathological changes in mice.

The following examples show different aspects of the immune response induced by different vaccine regimens.

Example 3

Heterologous Vaccination Increases the Epitope Coverage of Tau Phosphopeptide-Specific Antibodies in Rhesus Monkeys All animal experiments were approved and performed in accordance with local legislation on animal experiments. Rhesus macaques (*Macaca mulatta*) were obtained from Kunming Biomed International Ltd, China, Yunnan Yinmore Bio-Tech Co. LTD, China and Yunnan Laboratory Primates Inc., China. Animals were two to five years old at the start of immunization, and their minimum weight was 2.5 kg. A detailed clinical examination was performed prior to initiation of the treatment and weekly thereafter. Moreover, macaques were observed twice per day, and clinical signs were recorded.

Liposomal vaccines, e.g., Liposome Z or Liposome Z+(both containing tetrapalmitoylated phosphorylated tau peptide of SEQ ID NO: 2, 3D-(6-acyl) PHAD®, lipidated CpG oligonucleotide CpG 2006 and T-cell peptide T50), are referred to throughout the application as "A", while conjugate vaccines, e.g., Conjugate X (phosphorylated tau peptide of SEQ ID NO: 2 linked to CRM197), are referred to throughout the application as "B."

Groups of Rhesus macaques (n=3 males and 3 females per group) were immunized subcutaneously at day 1 and 29 with i) 1800 ug of acetate tetrapalmitoylated phosphorylated tau peptide of SEQ ID NO: 2 per dose of Liposome Z vaccine (regimen A-A); ii) 15 ug per dose of Conjugate X vaccine (regimen B-B); or iii) 1800 ug of acetate tetrapalmitoylated phosphorylated tau peptide of SEQ ID NO: 2 per dose of Liposome Z vaccine at day 1 followed by 15 ug per dose of Conjugate X vaccine at day 29 (regimen A-B). The epitope recognition profile of antibodies was determined by epitope mapping ELISA three weeks after the second immunization (Day 50) using a library of N-terminally biotinylated 8-mer peptides, shifted by one amino acid and covering the entire sequence of phospho tau peptide of SEQ ID NO: 2, as well as the sequence of SEQ ID NO: 4 (VYKSPVVSGDTSPRHL, non-phosphorylated peptide of SEQ ID NO: 2).

FIGS. 1A to 1C show that monkeys immunized with liposomal vaccine (Liposome Z) produced IgG antibodies that bound mostly to the N-terminal part of the peptide (A-A regimen, FIG. 1A), whereas monkeys immunized with the conjugate vaccine (Conjugate X) generated IgG antibodies that bound mostly to the C-terminal part of the peptide (B-B regimen, FIG. 1B), even though the liposomal vaccine and the conjugate vaccine contain the same phosphorylated tau peptide of SEQ ID NO: 2. The heterologous regimen induced antibodies that bound to both the N- and C-terminal part of the peptide (A-B regimen, FIG. 1C), therefore increasing the epitope coverage of the induced antibodies. Moreover, IgG antibodies induced in monkeys immunized with the liposomal vaccine (Liposome Z) did not bind to the non-phosphorylated library, whereas IgG antibodies induced in monkeys immunized with the conjugate vaccine (Conjugate X) also recognized the non-phosphorylated 8-mer peptide. IgG antibodies induced in monkeys immunized with the heterologous regimen (A-B) showed an intermediate binding to the non-phosphorylated library.

Example 4

Boost with the Liposomal Vaccine Induced a Shift Towards a "Liposome-Like" Epitope Profile in Rhesus Monkeys (A-B-B-A Regimen)

Figure 2:
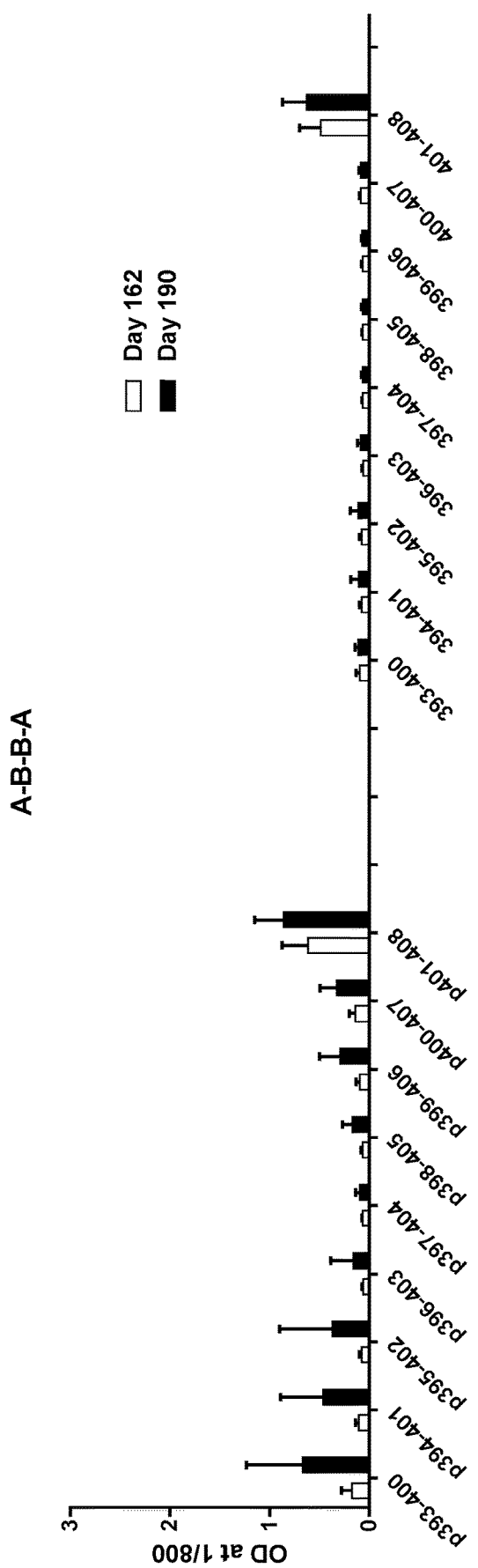
FIG. 2 shows the epitope recognition profile of antibodies induced after heterologous A-B-B vaccination (Day 162) compared to that induced after heterologous A-B-B-A vaccination (Day 190), with A being a liposomal vaccine comprising a TLR4 ligand and a lipidated CpG oligonucleotide as adjuvants, 1800 ug/dose of acetate tetrapalmitoylated phosphorylated tau peptide of SEQ ID NO: 2, corresponding to SEQ ID NO: 28, and encapsulated T50 helper T cell epitope, and B being a conjugate vaccine containing 15 ug/dose of CRM197 conjugated to a phosphorylated tau peptide of SEQ ID NO: 2 via a linker, and the conjugate vaccine was co-injected with alum and a CpG oligonucleotide), as determined by epitope mapping ELISA on short 8-mer overlapping peptides, covering phosphopeptide SEQ ID NO: 2 and peptide SEQ ID NO: 4.

Groups of Rhesus macaques (n=3 males and 3 females per group) were immunized subcutaneously at day 1 with 1800 ug of acetate tetrapalmitoylated phosphorylated tau peptide of SEQ ID NO: 2 per dose of Liposome Z vaccine, at days 29 and 85 with 15 ug per dose of Conjugate X vaccine, and at day 169 again with 1800 ug of acetate tetrapalmitoylated phosphorylated tau peptide of SEQ ID NO: 2 per dose of Liposome Z vaccine (regimen A-B-B-A). The epitope recognition profile of induced antibodies was determined as described in Example 6 by epitope mapping ELISA one week before (Day 162, A-B-B regimen), and three weeks after (Day 190, A-B-B-A regimen), the last boost with the liposomal vaccine. FIG. 2 shows that the priming with the liposome and boost with the conjugate vaccine induced a combination of N- and C-terminal IgG antibodies (A-B-B regimen), while the last boost with the liposomal vaccine led to a shift towards a "liposome-like" epitope profile in Rhesus monkeys (A-B-B-A regimen). The data show high flexibility in the induction of anti-Tau antibody responses using a heterologous vaccination strategy of novel anti-Tau vaccines described herein.

In summary, the studies in rhesus monkeys showed that heterologous vaccination with a sequential immunization schedule using vaccines, Liposome Z and Conjugate X, not only induces antibody titers against pTau and pathological Tau extracted from the brain of AD patients, but also increases the epitope coverage of the induced antibodies within the antigenic sequence used in both second generation vaccines.

Example 5

Heterologous Vaccination with the Liposome and Conjugate Vaccines Induced ePHF-Specific IgG Titers in the Serum and IgG Antibodies Specific to Tau Phosphopeptide in Cerebrospinal Fluid (CSF) of Rhesus Macaques Adult Rhesus macaques (n=3 males and 3 females per group) were immunized subcutaneously or intramuscularly with i) 1800 ug of acetate tetrapalmitoylated phosphorylated tau peptide of SEQ ID NO: 2 per dose of Liposome Z vaccine at days 1, 29, 85 and 169 (regimen A-A-A-A); ii) 1800 ug of acetate tetrapalmitoylated phosphorylated tau peptide of SEQ ID NO: 2 per dose of Liposome Z+ vaccine at days 1, 29, 85 and 169 (regimen A-A-A-A; iii) 1800 ug of acetate tetrapalmitoylated phosphorylated tau peptide of SEQ ID NO: 2 per dose of Liposome Z vaccine at day 1, 15 ug per dose of Conjugate X vaccine co-injected with alum and CpG oligonucleotide CpG 2006 at days 29 and 85, and 1800 ug of acetate tetrapalmitoylated phosphorylated tau peptide of SEQ ID NO: 2 per dose of Liposome Z vaccine at day 169 (regimen A-B-B-A); iv) 1800 ug of acetate tetrapalmitoylated phosphorylated tau peptide of SEQ ID NO: 2 per dose of Liposome Z+ vaccine at days 1 and 29 and 15 ug per dose of Conjugate X vaccine at days 85 and 169 (regimen A-A-B-B); or v) 15 ug per dose of Conjugate X vaccine at days 1 and 29 and 1800 ug of acetate tetrapalmitoylated phosphorylated tau peptide of SEQ ID NO: 2 per dose of Liposome Z+ vaccine at days 89 and 169 (regimen B-B-A-A). Bleedings were performed at day 190, and the sera were isolated.

Preparations of enriched paired helical filaments (ePHF) were obtained from post-mortem brain tissues of histologically confirmed AD subjects by sarcosyl extraction of insoluble tau, using a modified method of Greenberg and Davies (Greenberg and Davies, 1991, Proc Natl Acad Sci USA, 87(15):5827-31). Antibody titers specific for ePHF were evaluated using the Mesoscale Discovery (MSD) platform and ePHF as the coating antigen. Serum from immunized monkeys was serially diluted in assay buffer (PBS, 0.05% Tween20, 1% skim milk) and applied to 96-well MSD plates. After two hours of incubation, samples were removed and plates were washed in PBST (PBS, 0.05% Tween20). Antibodies were detected using a SulfoTag-labelled anti-human/monkey IgG antibody followed by a fixation step in 1% Paraformaldehyde (PFA) before adding the Read Buffer T. Plates were analyzed using a Sector Imager (MSD). All samples were run in eight two-fold serial dilutions, with positive and negative control samples included on each plate. Antibody titers expressed in Arbitrary Units (AU) per mL were calculated for each individual monkey. Fold-change in relation to the geometric mean of titers obtained with the A-A-A-A, respectively to each liposomal composition, is represented for each monkey as well as the geometric mean per group.

Antibody titers specific for phosphorylated tau peptide of SEQ ID NO: 2 were evaluated using the MSD platform. Gold small spot streptavidin 96-well plates (MSD) previously saturated with 1% Blocker A in PBS were coated with phosphorylated tau peptide of SEQ ID NO: 2 biotinylated on the N-terminus of the sequence. CSF from immunized monkeys was serially diluted in assay buffer (PBS, 0.05% Tween 20, 1% Blocker A) and applied to 96-well MSD plates. After two hours of incubation, samples were removed and plates were washed with PBST (PBS, 0.05% Tween 20). Antibodies were detected using a SulfoTag-labelled anti-human/monkey IgG antibody before adding the Read Buffer T. Plates were analyzed using a Sector Imager (MSD). All samples were run in eight two-fold serial dilutions, with positive and negative control samples included on each plate. Antibody titers expressed in AU/mL were calculated for each individual monkey. Fold-change in relation to the geometric mean of titers obtained with the A-A-A-A, respectively to each liposomal composition, is represented for each monkey as well as the geometric mean per group. Samples with high red blood cell counts were removed from the analysis to avoid any bias in antibody titers due to blood contamination.

Figure 3:
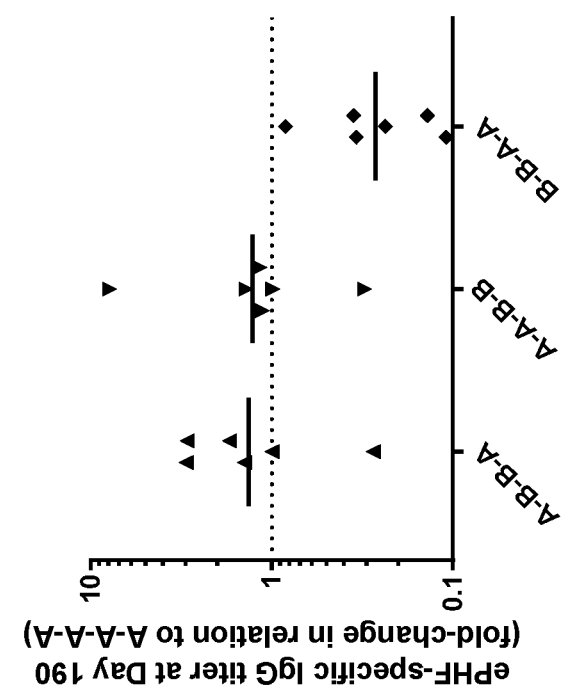
FIG. 3 shows the IgG titers specific to enriched paired helical filaments (ePHF) isolated from the post mortem brain of Alzheimer's disease patients at day 190 after heterologous vaccination (A-B-B-A, A-A-B-B or B-B-A-A, with A being a liposomal vaccine comprising a TLR4 ligand and a lipidated CpG oligonucleotide as adjuvants, 1800 ug/dose of acetate tetrapalmitoylated phosphorylated tau peptide of SEQ ID NO: 2, and encapsulated T50 helper T cell epitope, and B being a conjugate vaccine containing 15 ug/dose of CRM197 conjugated to a phosphorylated tau peptide of SEQ ID NO: 2 via a linker and the conjugate vaccine was co-injected with alum and a CpG oligonucleotide) or homologous vaccination (A-A-A-A), with the fold-change in relation to A-A-A-A plotted.

As presented in FIG. 3, monkeys that were administered the heterologous regimens A-B-B-A and A-A-B-B (with A being liposomal vaccine (with acetate tetrapalmitoylated phosphorylated tau peptide of SEQ ID NO: 2) with encapsulated T50, TLR4 ligand and lipidated CpG oligonucleotide, and B being conjugate vaccine (phosphopeptide SEQ ID NO: 2 linked to CRM197) co-injected with alum and CpG oligonucleotide) showed ePHF-specific titers at day 190 (three weeks after the fourth injection) that were similar to or higher than those for the monkeys that were administered the homologous treatment (A-A-A-A) (fold-change ≥1).

However, all the monkeys that were injected with the heterologous regimen B-B-A-A showed lower ePHF-specific titers than those for the monkeys that were administered the homologous treatment (A-A-A-A) (fold-change ≤1).

Figure 6:
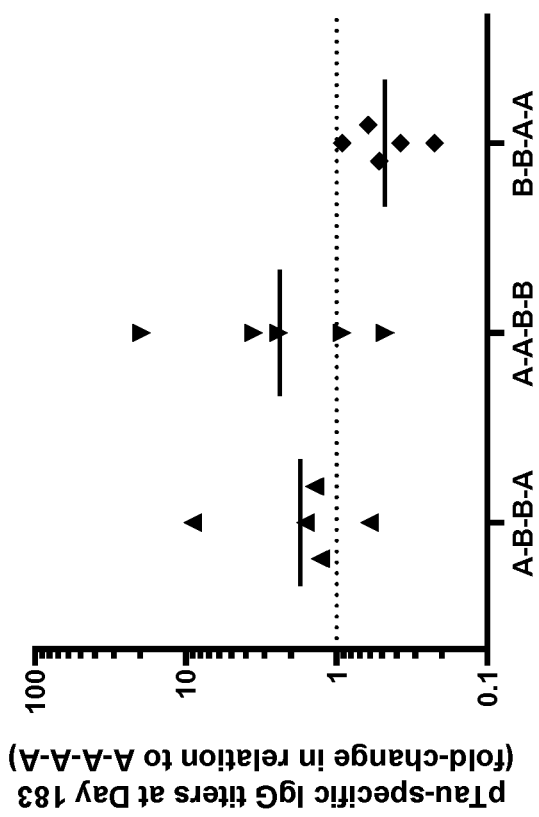
FIG. 6 shows the IgG titers specific to phosphopeptide having a sequence of SEQ ID NO: 2 biotinylated on the N-terminus in the cerebrospinal fluid (CSF) of Rhesus monkeys at day 183 after the first immunization, following heterologous vaccination (A-B-B-A, A-A-B-B or B-B-A-A, with A being a liposomal vaccine comprising a TLR4 ligand and a lipidated CpG oligonucleotide as adjuvants, 1800 μg/dose of acetate tetrapalmitoylated phosphorylated tau peptide of SEQ ID NO: 2, and encapsulated T50 helper T-cell epitope, and B being a conjugate vaccine containing 15 μg/dose of CRM197 conjugated to a phosphorylated tau peptide of SEQ ID NO: 2 via a linker and co-injected with alum and a CpG oligonucleotide), with the fold-change in relation to homologous vaccination A-A-A-A plotted.

FIG. 6 shows that similar conclusions could be drawn when monitoring the IgG antibody response in the cerebrospinal fluid of these monkeys at day 183 (two weeks after the fourth injection). Monkeys that were administered the heterologous regimens A-B-B-A and A-A-B-B (with A being liposomal vaccine (with acetate tetrapalmitoylated phosphorylated tau peptide of SEQ ID NO: 2, encapsulated T50 (TLR4 ligand) and lipidated CpG oligonucleotide, and B being conjugate vaccine (phosphopeptide SEQ ID NO: 2 linked to CRM197) co-injected with alum and CpG oligonucleotide) showed IgG titers specific to the phosphorylated tau peptide of SEQ ID NO: 2 that were overall higher than those for the monkeys that were administered the homologous treatment (A-A-A-A) (fold-change ≥1). However, all monkeys that were injected with the heterologous regimen B-B-A-A showed lower IgG titers specific to the phosphorylated tau peptide of SEQ ID NO: 2 than those for the monkeys that were administered the homologous treatment (A-A-A-A) (fold-change ≤1).

Overall, results from this study indicate that a heterologous regimen with a liposomal vaccine as the priming composition induced higher ptau specific IgG titers as compared to the regimen with a conjugate vaccine as the priming composition for systemic as well as local (in CSF) antibody responses.

Example 6

Heterologous Vaccination with a Primer Liposome Vaccine Induced Higher IgG Titers Specific to Tau Phosphopeptide and ePHF in Rhesus Monkeys than the Homologous Regimen Adult Rhesus macaques (n=3 males and 3 females per group) were immunized subcutaneously or intramuscularly with i) 1800 ug of acetate tetrapalmitoylated phosphorylated tau peptide of SEQ ID NO: 2 per dose of Liposome Z vaccine at days 1, 29 and 85 (regimen A-A-A); ii) 1800 ug of acetate tetrapalmitoylated phosphorylated tau peptide of SEQ ID NO: 2 per dose of Liposome Z+ vaccine (regimen A-A-A); iii) 1800 ug of acetate tetrapalmitoylated phosphorylated tau peptide of SEQ ID NO: 2 per dose of Liposome Z vaccine at day 1 and 15 ug per dose of Conjugate X vaccine at days 29 and 85 (regimen A-B-B); or iv) 1800 ug of acetate tetrapalmitoylated phosphorylated tau peptide of SEQ ID NO: 2 per dose of Liposome Z+ vaccine at days 1 and 29 and 15 ug per dose of Conjugate X vaccine at day 85 (regimen A-A-B). Bleedings were performed at day 106, and the sera were isolated.

Phospho tau peptide-specific IgG antibody titers were determined by ELISA, using phosphorylated tau peptide of SEQ ID NO: 2 as the coating antigen. Serum from immunized monkeys was serially diluted in assay buffer (PBS, 0.05% Tween 20, 1% BSA) and applied to 96-well plates previously coated with the relevant peptide. After two hours of incubation, samples were removed and plates washed in PBST (PBS, 0.05% Tween 20). Antibodies were detected using an HRP-conjugated anti-monkey IgG, followed by ABTS substrate (Roche). All samples were run in eight two-fold serial dilutions, with positive and negative control samples included on each plate. ata were expressed as individual endpoint titers (last serum dilution inducing a positive response) together with the geometric mean per group. One-way ANOVA test with Tukey's multiple comparison was used for statistical analysis.

Antibody titers specific for ePHF were evaluated using the MSD platform. Gold small spot streptavidin 96-well plates (MSD) previously saturated with 1% BSA in PBS were coated with the biotinylated anti-tau capturing antibody (HT7-biotin, ThermoScientific) before incubation with ePHF isolated from brains of Alzheimer's disease patients. After one hour of incubation, plates were washed with PBST, and serial dilutions of sera were added and incubated for two hours. Bound antibodies were detected using a SulfoTag-labelled anti-human/monkey IgG antibody followed by a fixation step in 1% PFA before adding the Read Buffer T. Plates were analyzed using a Sector Imager (MSD). All samples were run in eight two-fold serial dilutions, with positive and negative control samples included on each plate. Results were expressed in AU/mL for each individual monkey, together with the geometric mean per group. Antibody titers specific for ePHF at day 106 are represented. One-way ANOVA test with Tukey's multiple comparison was used for statistical analysis.

Figure 4A:
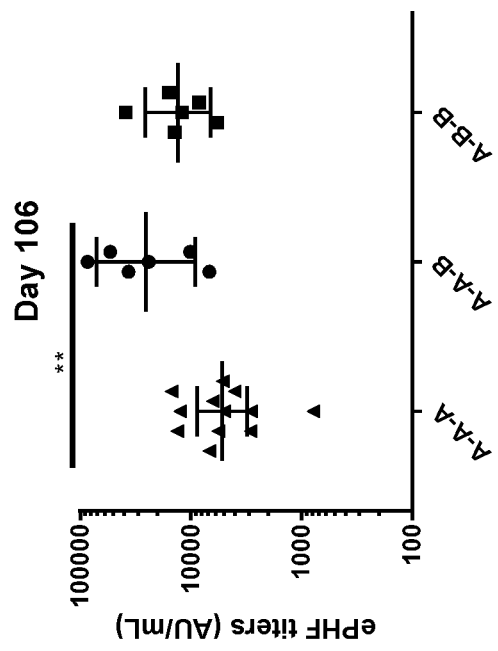
FIG. 4A shows the IgG titers specific to phosphopeptide having a sequence of SEQ ID NO: 2 (T3.5) in Rhesus monkeys at day 106 after homologous (A-A-A) and heterologous (A-A-B and A-B-B) immunization regimens as measured by ELISA, with the data presented as endpoint titers (EPT)

FIG. 4A shows that heterologous regimens A-A-B and A-B-B induced statistically significantly higher levels of IgG antibodies specific to phospho tau peptide than the homologous regimen A-A-A in Rhesus monkeys.

Figure 4B:
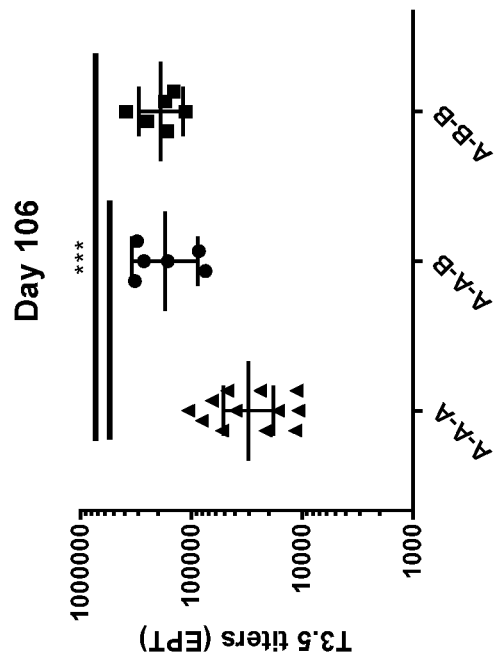
FIG. 4B shows the IgG titers specific to ePHF in Rhesus monkeys at day 106 after homologous (A-A-A) and heterologous (A-A-B and A-B-B) immunization regimens, presented as arbitrary units (AU)/mL.

FIG. 4B shows that the heterologous regimen A-A-B induced statistically significantly higher levels of ePHF-specific IgG antibodies than the homologous regimen A-A-A in Rhesus monkeys, while A-B-B showed a trend towards a higher level of ePHF-specific IgG titers than the homologous regimen A-A-A in Rhesus monkeys.

Overall, the data shows that heterologous immunization regimens with liposome vaccine (A) as a priming composition induced higher titers of antibodies against phosphorylated tau peptide of SEQ ID NO: 2 and ePHF than the homologous regimen A-A-A.

Example 7

The Quality of ePHF-Specific IgG Antibodies Induced by the Heterologous Regimens is Similar to or Better than of the One Induced by a Homologous Regimen in Rhesus Monkeys Adult Rhesus macaques (n=3 males and 3 females per group) were immunized subcutaneously with i) 1800 ug of acetate tetrapalmitoylated phosphorylated tau peptide of SEQ ID NO: 2 per dose of Liposome Z vaccine at days 1, 29, 85 and 169 (regimen A-A-A-A) or ii) 1800 ug of acetate tetrapalmitoylated phosphorylated tau peptide of SEQ ID NO: 2 per dose of Liposome Z vaccine at day 1, 15 ug per dose of Conjugate X vaccine at days 29 and 85, and 1800 ug of acetate tetrapalmitoylated phosphorylated tau peptide of SEQ ID NO: 2 per dose of Liposome Z vaccine at day 169 (regimen A-B-B-A), or intramuscularly with iii) 1800 ug of acetate tetrapalmitoylated phosphorylated tau peptide of SEQ ID NO: 2 per dose of Liposome Z+ vaccine at days 1, 29, 85 and 169 (regimen A-A-A-A) or iv) 1800 ug of acetate tetrapalmitoylated phosphorylated tau peptide of SEQ ID NO: 2 per dose of Liposome Z+ vaccine at days 1 and 29 and 15 ug per dose of Conjugate X vaccine at days 85 and 169 (regimen A-A-B-B). Bleedings were performed at day 190, and the sera were isolated.

The quality of antibodies specific for enriched paired helical filaments (ePHF) was evaluated as binding to the low coating concentration of ePHF (which is also referred to herein as under limited coating condition), using the MSD platform. Serum from immunized monkeys was serially diluted in assay buffer (PBS, 0.05% Tween20, 1% skim milk) and applied to 96-well MSD plates. After two hours of incubation, samples were removed, and plates were washed in PBST (PBS, 0.05% Tween20). Antibodies were detected using a SulfoTag-labelled anti-human/monkey IgG antibody followed by a fixation step in 1% PFA before adding the Read Buffer T. Plates were analyzed using a Sector Imager (MSD). All samples were run in eight two-fold serial dilutions, with positive and negative control samples included on each plate. Antibody titers expressed in AU/mL were calculated for each individual monkey.

Phospho tau peptide-specific IgG antibody titers were determined by ELISA, using phosphorylated tau peptide of SEQ ID NO: 2 as the coating antigen. Serum from immunized monkeys was serially diluted in assay buffer (PBS, 0.05% Tween 20, 1% BSA) and applied to 96-well plates previously coated with the relevant peptide. After two hours of incubation, samples were removed and plates washed in PBST (PBS, 0.05% Tween 20). Antibodies were detected using an HRP-conjugated anti-monkey IgG, followed by ABTS substrate (Roche). All samples were run in eight two-fold serial dilutions, with positive and negative control samples included on each plate. Data were expressed as individual endpoint titers (last serum dilution inducing a positive response) together with the geometric mean per group.

Universal T-cell epitope (T50)-specific IgG antibody titers were determined by ELISA, using T50 peptide as the coating antigen. Serum from immunized monkeys was serially diluted in assay buffer (PBS, 0.05% Tween 20, 1% skim milk) and applied to 96-well plates previously coated with the relevant peptide. After two hours of incubation, samples were removed and plates washed in PBST (PBS, 0.05% Tween 20). Antibodies were detected using an HRP-conjugated anti-monkey IgG, followed by ABTS substrate (Roche). All samples were run in eight two-fold serial dilutions, with positive and negative control samples included on each plate. Data were expressed as individual endpoint titers (last serum dilution inducing a positive response) together with the geometric mean per group.

Fold-change between phospho tau peptide-specific IgG antibody titers and universal T-cell epitope (T50)-specific IgG antibody titers is represented for each monkey as well as the geometric mean per group. Mann-Whitney test has been used for the statistical analysis.

Figure 5A:
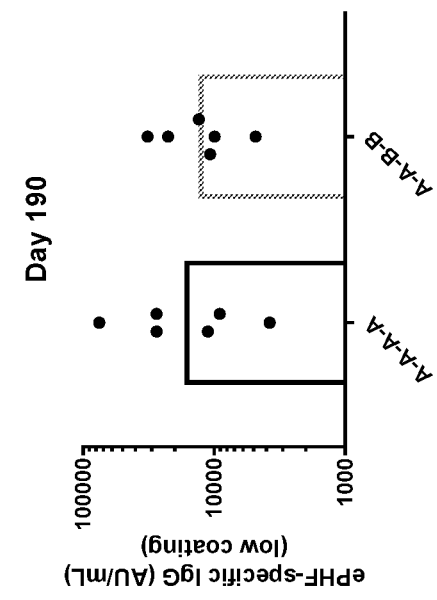
FIGS. 5A and 5B show the quality of the ePHF-specific IgG antibodies induced by heterologous regimens A-B-B-A (FIG. 5A) and A-A-B-B (FIG. 5B) compared to those induced by the homologous A-A-A-A regimen, as measured by the binding to ePHF in limited coating conditions, with the ePHF-specific IgG titers expressed in AU/m and measured by MSD on the limited coating of ePHF plotted.
Figure 5B:
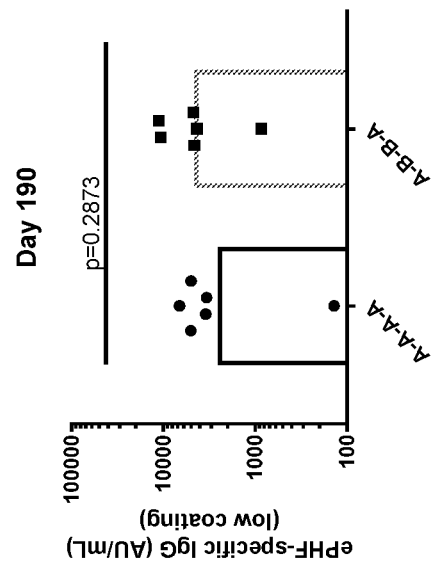

FIGS. 5A and 5B show ePHF-specific IgG titers under the limited coating condition, reflecting antibodies with a high binding capacity. FIG. 5A shows that the A-B-B-A regimen induced slightly higher antibody titers than the A-A-A-A regimen, while A-A-B-B induced similar IgG titers. Moreover, as shown in FIG. 3, the heterologous regimens A-B-B-A as well as A-A-B-B induced overall similar or higher ePHF-specific antibody titers as compared to the homologous regimen with the liposomal vaccine alone (A-A-A-A regimen, fold-change ≥1). Overall, the data suggest that the quality of ePHF-specific antibodies induced by heterologous vaccination is similar to or better than the quality of antibodies induced by the homologous A-A-A-A vaccination regimen in Rhesus monkeys.

Figure 7:
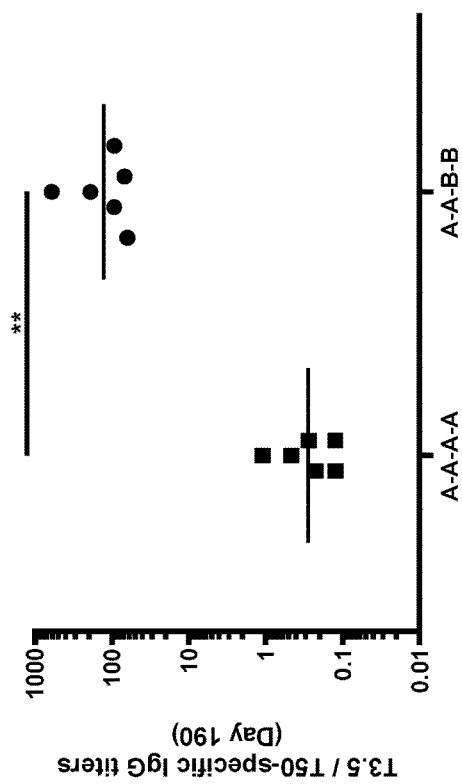
FIG. 7 shows the ratio of the IgG titers specific to the phosphopeptide having a sequence of SEQ ID NO: 2 (T3.5) over the IgG titers specific to the T50 peptide in Rhesus monkeys at day 190 after the first immunization, following homologous (A-A-A-A) and heterologous (A-A-B-B and A-B-B-A) immunization as measured by ELISA. Statistical analysis was performed using the Mann-Whitney test. (**p<0.001).
Figure 7:
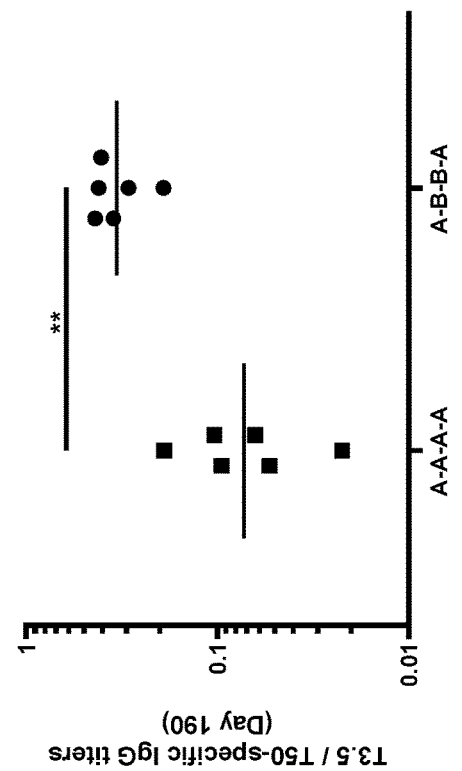

While not wishing to be bound by theory, it is believed that a heterologous regimen according to the present application diversifies the CD4 T cell response. Due to the limited space in the germinal center, if one keeps immunizing with the same CD4 helper epitopes/protein (e.g. tetanus) then the tetanus specific B and T cells will crowd the tau-specific B cells out of the germinal center. On the other hand, if one alternates CD4 stimuli, then the tau specific B cells (which are also receiving help from the tetanus or diphtheria specific T cells) will have better access to them. It was observed in the present invention that, when an A-A-A-A regimen was used, the titers of antibodies to the T50 helper peptide increased greatly. When a heterologous regimen of A and B was used, the titers of antibodies to the T50 helper peptide were much lower. FIG. 7 shows that the ratio between IgG antibody titers directed against the phosphorylated tau peptide of SEQ ID NO: 2 and IgG antibody titers directed against the T50 peptide was higher in the heterologous regimen (A-B-B-A and A-A-B-B) as compared to their respective homologous regimen (A-A-A-A). That is a reflection of the diversity of the CD4 T cell response and also demonstrates that the T50-specific B cell response is not completely dominating the anti-pTau response.

It is understood that the examples and embodiments described herein are for illustrative purposes only, and that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

```
SEQUENCE LISTING
SEQ ID NO: 1 - phospho-tau peptide (7.1)
GDRSGYS[pS]PG[pS]PG[pT]PGSRSRT SEQ ID NO: 2 - phospho-tau peptide (T3.5)
VYK[pS]PVVSGDT[pS]PRHL SEQ ID NO: 3 - phospho-tau peptide (22.1)
SSTGSIDMVD[pS]PQLA[pT]LA SEQ ID NO: 4 - tau peptide
VYKSPVVSGDTSPRHL SEQ ID NO: 5 - phospho-tau peptide
RENAKAKTDHGAEIVYK[pS]PVVSGDT[pS]PRHL SEQ ID NO: 6 - phospho-tau peptide
RQEFEVMEDHAGT[pY]GL SEQ ID NO: 7 - phospho-tau peptide
PGSRSR[pT]P[pS]LPTPPTR SEQ ID NO: 8 - phospho-tau peptide
GYSSPG[pS]PG[pT]PGSRSR SEQ ID NO: 9 - phospho-tau peptide
GDT[pS]PRHL[pS]NVSSTGSID SEQ ID NO: 10 - phospho-tau peptide
PG[pS]PG[pT]PGSRSR[pT]P[pS]LP SEQ ID NO: 11 - phospho-tau peptide
HL[pS]NVSSTGSID SEQ ID NO: 12 - phospho-tau peptide
VSGDT[pS]PRHL SEQ ID NO: 13 - T50 T cell epitope
AKFVAAWTLKAAAVVRQYIKANSKFIGITELVVRFNNFTVSFWLRVPKV
SASHLE-NH2

SEQ ID NO: 14 - T46 T cell epitope
AKFVAAWTLKAAAGSQYIKANSKFIGITELGSFNNFTVSFWLRVPKVSA
SHLEK(Pal)K(Pal)-NH2

SEQ ID NO: 15 - T48 helper T cell epitope
AKFVAAWTLKAAAGSQYIKANSKFIGITELGSFNNFTVSFWLRVPKVSA
SHLEGSLINSTKIYSYFPSVISKVNQ-NH2

SEQ ID NO: 16 - T51 helper T cell epitope
AKFVAAWTLKAAARRQYIKANSKFIGITELRRFNNFTVSFWLRVPKVSA
SHLE-NH2

SEQ ID NO: 17 - T52 helper T cell epitope
AKFVAAWTLKAAARKQYIKANSKFIGITELRKFNNFTVSFWLRVPKVSA
SHLE-NH2

SEQ ID NO: 18 - CpG 2006 (also known as CpG 7909)
5'-tcgtcgttttgtcgttttgtcgtt-3'
wherein lower case means phosphorothioate (ps)
internucleotide linkages SEQ ID NO: 19 - CpG 1018
5'-tgactgtgaacgttcgagatga-3'
wherein lower case means phosphorothioate
internucleotide linkages SEQ ID NO: 20 - CpG2395
5'-tcgtcgttttcggcgcgcgccg-3'
wherein lower case means phosphorothioate
internucleotide linkages SEQ ID NO: 21 - CpG2216
5'-ggGGGACGATCGTCgggggg-3'
wherein lower case means phosphorothioate
internucleotide linkages and capital letters
means phosphodiester (po) linkages SEQ ID NO:22 - CpG2336
5'-gggGACGACGTCGTGgggggg-3',
wherein lower case means phosphorothioate
internucleotide linkages and capital letters
means phosphodiester linkages SEQ ID NO:23 - Pan DR epitope (PADRE) peptide
AKFVAAWTLKAAA

SEQ ID NO:24 - P2
QYIKANSKFIGITEL

SEQ ID NO:25 - P30
FNNFTVSFWLRVPKVSASHLE

SEQ ID NO: 26 - TT586-605
LINSTKIYSYFPSVISKVNQ

SEQ ID NO: 27 - palmitoylated phospho-tau peptide
(palmitoylated 7.1)
K(pal)K(pal)GDRSGYS[pS]PG[pS]PG[pT]PGSRSRTK(pal)
K(pal)

SEQ ID NO: 28 - palmitoylated phospho-tau peptide
(T3, palmitoylated T3.5, palmitoylated SEQ ID
NO: 2)
K(pal)K(pal)VYK[pS]PVVSGDT[pS]PRHLK(pal)K(pal)

SEQ ID NO: 29 - palmitoylated phospho-tau peptide
(palmitoylated 22.1)
K(pal)K(pal)SSTGSIDMVD[pS]PQLA[pT]LAK(pal)K(pal)

SEQ ID NO: 30 - palmitoylated tau peptide
K(pal)K(pal)VYKSPVVSGDTSPRHLK(pal)K(pal)
```

-continued

SEQ ID NO: 31 - palmitoylated phospho-tau peptide
K(pal)K(pal)RENAKAKTDHGAEIVYK[pS]PVVSGDT[pS]PRHLK
(pal)K(pal)

SEQ ID NO: 32 - palmitoylated phospho-tau peptide
K(pal)K(pal)RQEFEVMEDHAGT[pY]GLK(pal)K(pal)

SEQ ID NO: 33 - palmitoylated phospho-tau peptide
K(pal)K(pal)PGSRSR[pT]P[pS]LPTPPTRK(pal)K(pal)

SEQ ID NO: 34 - palmitoylated phospho-tau peptide
K(pal)K(pal)GYSSPG[pS]PG[pT]PGSRSRK(pal)K(pal)

SEQ ID NO: 35 - palmitoylated phospho-tau peptide
K(pal)K(pal)GDT[pS]PRHL[pS]NVSSTGSIDK(pal)K(pal)

SEQ ID NO: 36 - palmitoylated phospho-tau peptide
K(pal)K(pal)PG[pS]PG[pT]PGSRSR[pT]P[pS]LPK(pal)K
(pal)

SEQ ID NO: 37 - palmitoylated phospho-tau peptide
K(pal)K(pal)HL[pS]NVSSTGSIDK(pal)K(pal)

SEQ ID NO: 38 - palmitoylated phospho-tau peptide
K(pal)K(pal)VSGDT[PRHLK(pal)K(pal)

SEQ ID NO:39 - T50 without the C-terminal amide
AKFVAAWTLKAAAVVRQYIKANSKFIGITELVVRFNNFTVSFWLRVPKV
SASHLE SEQ ID NO: 40 - T46 without the -Lys(Pal)-
Lys(Pal)-NH2 at the C-terminal
AKFVAAWTLKAAAGSQYIKANSKFIGITELGSFNNFTVSFWLRVPKVSA
SHLE SEQ ID NO: 41 - T48 without the C-terminal amide
AKFVAAWTLKAAAGSQYIKANSKFIGITELGSFNNFTVSFWLRVPKVSA
SHLEGSLINSTKIYSYFPSVISKVNQ SEQ ID NO: 42 - T51 without the C-terminal amide
AKFVAAWTLKAAARRQYIKANSKFIGITELRRFNNFTVSFWLRVPKVSA
SHLE SEQ ID NO: 43 - T52 without the C-terminal amide
AKFVAAWTLKAAARKQYIKANSKFIGITELRKFNNFTVSFWLRVPKVSA
SHLE SEQ ID NO: 44 - T57 (56, 57)
AKFVAAWTLKAAAVVRQYIKANSKFIGITELVVRFNNFTVSFWLRVPKV
SASHLE-K(Pal)K(Pal)-NH2

REFERENCES

Asuni A A et al., J Neurosci. 2007 Aug. 22; 27(34):9115-29
Bentebibel et al., 2013, Sci Transl Med., 5(176):176ra32
Crotty, 2011, Annual Reviews of Immunology. Vol 29: p 621-663
Friedhoff et al., Biochimica et Biophysica Acta 1502 (2000) 122-132
Greenberg and Davies, 1991, Proc Natl Acad Sci USA, 87(15):5827-31
Hanger et al., Trends Mol Med. 15:112-9, 2009
Hickman et al., J. Biol. Chem. vol. 286, NO. 16, pp. 13966-13976, Apr. 22, 2011
Kontsekova E et al., Alzheimers Res Ther. 2014 Aug. 1; 6(4):44
Novak P et al., Lancet Neurology 2017, 16:123-134
Peeraer et al., 2015, Neurobiol Dis., 73:83-95
Ries et al., 2015, Org. Biomol. Chem., 13:9673
Spensieri et al., 2013, Proc Natl Acad Sci USA., 110(35): 14330-5
Theunis C et al., PLoS One. 2013; 8(8): e72301
U.S. Pat. No. 7,741,297
U.S. Pat. No. 8,647,631
U.S. Pat. No. 9,687,447
WO90/14837
WO2010/115843

It is claimed:

1. A method of inducing antibodies against at least one of phosphorylated Tau and enriched paired helical filaments (ePHFs) in a subject in need thereof, the method comprising:
   (i) administering to the subject a priming composition comprising an immunologically effective amount of a liposome comprising:
      a. a first tau phosphopeptide;
      b. a helper T-cell epitope;
      c. a lipidated CpG oligonucleotide; and
      d. an adjuvant containing a toll-like receptor 4 ligand;
   wherein the tau phosphopeptide is presented on the surface of the liposome, and the priming composition further comprises a pharmaceutically acceptable carrier; and
   (ii) administering to the subject a first boosting composition comprising an immunologically effective amount of a conjugate comprising a second tau phosphopeptide and an immunogenic carrier conjugated thereto via a linker, the conjugate having the structure of formula (I):

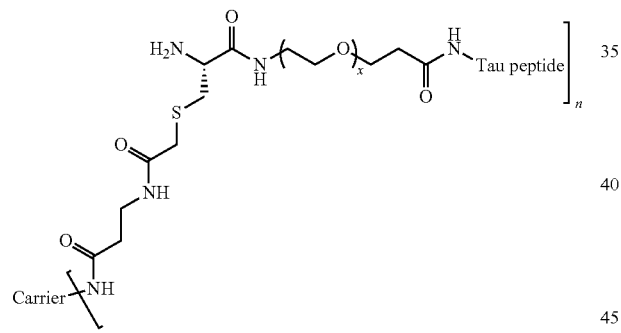

or having the structure of formula (II):

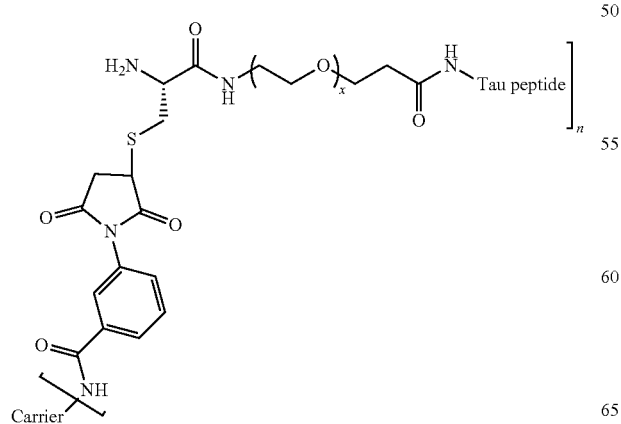

wherein
   x is an integer of 0 to 10;
   n is an integer of 3 to 15;
   Tau peptide represents the second tau phosphopeptide; and
   Carrier represents the immunogenic carrier selected from the group consisting of keyhole limpet hemocyanin (KLH), tetanus toxoid, CRM197 and an outer membrane protein mixture from *N. meningitidis* (OMP), or a derivative thereof; and
   the first boosting composition further comprises a pharmaceutically acceptable carrier;
wherein the first tau phosphopeptide and the second tau phosphopeptide each independently comprises an amino acid sequence selected from the group consisting of SEQ ID NO: 1 to SEQ ID NO: 3 and SEQ ID NO: 5 to SEQ ID NO: 12.

2. The method of claim 1, wherein:
the liposome comprises:
   a. the first tau phosphopeptide having an amino acid sequence selected from the group consisting of SEQ ID NO: 27 to SEQ ID NO: 29 and SEQ ID NO: 31 to SEQ ID NO: 38;
   b. the helper T cell epitope having an amino acid sequence selected from the group consisting of SEQ ID NO: 39 to SEQ ID NO: 44;
   c. the lipidated CpG oligonucleotide having a nucleotide sequence selected from the group consisting of SEQ ID NO: 18 to SEQ ID NO: 22, wherein the CpG oligonucleotide comprises one or more phosphorothioate internucleotide linkages, and the CpG oligonucleotide is covalently linked to at least one cholesterol via a linker; and
   d. monophosphoryl lipid A (MPLA); and
the conjugate comprises the second tau phosphopeptide having an amino acid sequence selected from the group consisting of SEQ ID NO: 1 to SEQ ID NO: 3 or SEQ ID NO: 5 to SEQ ID NO: 12 conjugated to CRM197 via the linker.

3. The method of claim 1, wherein the conjugate has the structure of:

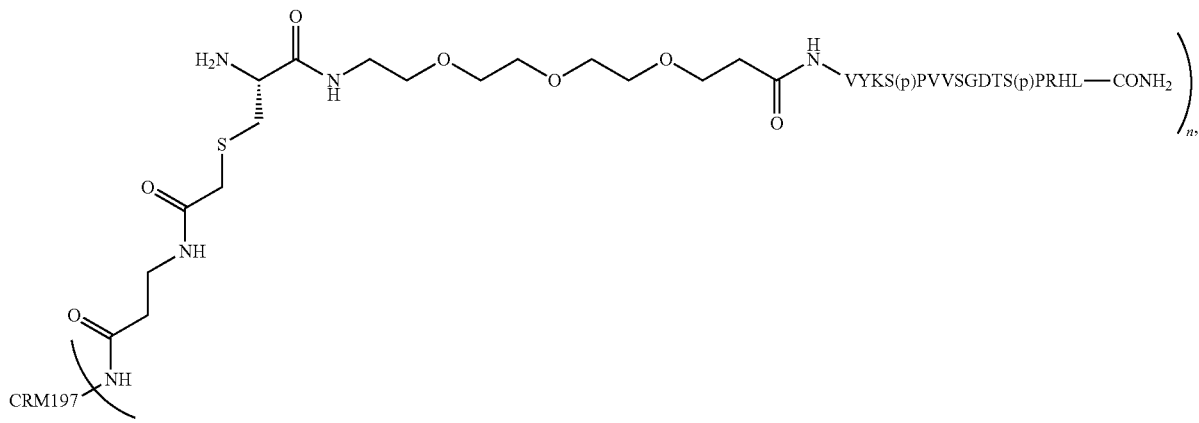

wherein n is an integer of 3 to 7 and VYKS(p)PVVSGDTS(p)PRHL-CONH₂ comprises the phospho-tau peptide of SEQ ID NO:2.

4. A method for inducing antibodies against at least one of phosphorylated Tau and enriched paired helical filaments (ePHFs) in a subject in need thereof, the method comprising:
(i) administering to the subject a priming composition comprising an immunologically effective amount of a liposome comprising:

a. a first tau phosphopeptide having an amino acid sequence selected from the group consisting of SEQ ID NO: 27 to SEQ ID NO: 29 or SEQ ID NO: 31 to SEQ ID NO: 38;
b. a helper T cell epitope having an amino acid sequence selected from the group consisting of SEQ ID NO: 39 to SEQ ID NO: 44;
c. a lipidated CpG oligonucleotide having a nucleotide sequence selected from the group consisting of SEQ ID NO: 18 to SEQ ID NO: 22, wherein the CpG oligonucleotide comprises one or more phosphorothioate internucleotide linkages, and the CpG oligonucleotide is covalently linked to at least one cholesterol via a linker; and
d. monophosphoryl lipid A (MPLA);

wherein the first tau phosphopeptide is presented on the surface of the liposome, and the priming composition further comprises a pharmaceutically acceptable carrier; and
(ii) administering to the subject a first boosting composition comprising an immunologically effective amount of a conjugate comprising a second tau phosphopeptide and an immunogenic carrier conjugated thereto via a linker, the conjugate having the structure of:

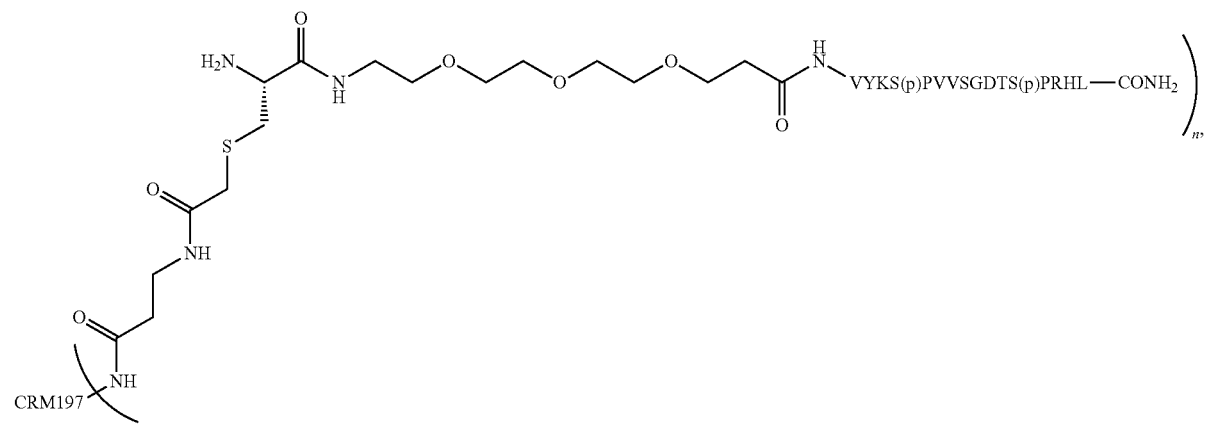

wherein n is an integer of 3 to 7 and VYKS(p)PVVSGDTS(p)PRHL-CONH₂ comprises the phospho-tau peptide of SEQ ID NO:2, and wherein the first boosting composition further comprises a pharmaceutically acceptable carrier.

5. A method for inducing antibodies against at least one of phosphorylated Tau and enriched paired helical filaments (ePHFs) in a subject in need thereof, the method comprising
(i) administering to the subject a priming composition comprising an immunologically effective amount of a liposome comprising:
(1) a first tau phosphopeptide having the amino acid sequence of SEQ ID NO:28;
(2) a toll-like receptor 4 agonist comprising monophosphoryl hexa-acyl Lipid A, 3-deacyl;

(3) a helper T-cell epitope comprising the amino acid sequence of SEQ ID NO: 39;
(4) a lipidated CpG oligonucleotide comprising the nucleotide sequence of SEQ ID NO:18; and
(5) at least one lipid selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol, wherein the first tau phosphopeptide is presented on the surface of the liposome, and the priming composition further comprises a pharmaceutically acceptable carrier; and (ii) administering to the subject a first boosting composition comprising an immunologically effective amount of a conjugate comprising a second tau phosphopeptide and an immunogenic carrier conjugated thereto via a linker, the conjugate having the structure of:

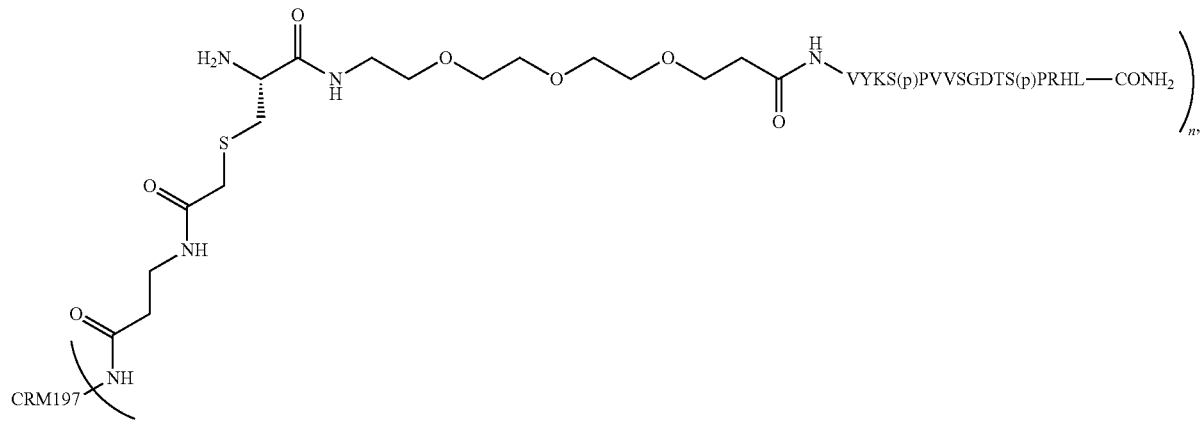

wherein n is an integer of 3 to 7 and VYKS(p)PVVSGDTS(p)PRHL-CONH$_2$ comprises the phospho-tau peptide of SEQ ID NO:2, and wherein the first boosting composition further comprises a pharmaceutically acceptable carrier.

6. The method of claim 1, further comprising administering the first boosting composition to the subject at least once after the initial administration of the first boosting composition.

7. The method of claim 1, further comprising administering to the subject a second boosting composition comprising an immunologically effective amount of the liposome and a pharmaceutically acceptable carrier.

8. The method of claim 7, further comprising administering to the subject the second boosting composition at least once after the initial administration of the second boosting composition.

9. A method for inducing antibodies against at least one of phosphorylated Tau and enriched paired helical filaments (ePHFs) in a subject in need thereof, the method comprising (i) administering to the subject a priming composition comprising an immunologically effective amount of a liposome comprising:
(1) a first tau phosphopeptide having the amino acid sequence of SEQ ID NO:28;
(2) a toll-like receptor 4 agonist comprising monophosphoryl hexa-acyl Lipid A, 3-deacyl;
(3) a helper T-cell epitope comprising the amino acid sequence of SEQ ID NO: 39;
(4) a lipidated CpG oligonucleotide comprising the nucleotide sequence of SEQ ID NO:18; and
(5) at least one lipid selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol, wherein the first tau phosphopeptide is presented on the surface of the liposome, and the priming composition further comprises a pharmaceutically acceptable carrier; and (ii) administering to the subject a first boosting composition comprising an immunologically effective amount of a conjugate comprising a second tau phosphopeptide and an immunogenic carrier conjugated thereto via a linker, the conjugate having the structure of:

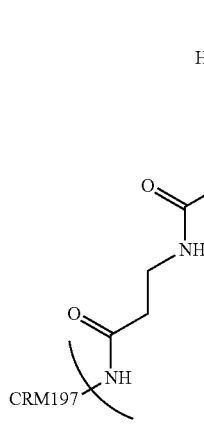
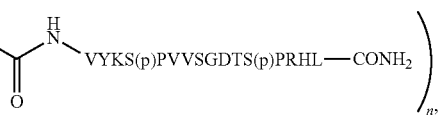

wherein n is an integer of 3 to 7 and VYKS(p)PVVSGDTS(p)PRHL-CONH₂ comprises the phosphotau peptide of SEQ ID NO:2, and wherein the first boosting composition further comprises a pharmaceutically acceptable carrier; and (iii) administering to the subject the first boosting composition or a second boosting composition comprising an immunologically effective amount of the liposome and a pharmaceutically acceptable carrier.

10. The method of claim 9, wherein (ii) is conducted before (iii).

11. The method of claim 9, wherein (ii) is conducted after (iii).

12. The method of claim 9, further comprising administering the first boosting composition to the subject at least once after the initial administration of the first boosting composition.

13. The method of claim 9, comprising administering the second boosting composition to the subject at least once.

14. The method of claim 1, wherein the subject is in need of a treatment of a neurodegenerative disease or disorder caused by or associated with the formation of neurofibrillary lesions.

15. The method of claim 14, wherein the neurodegenerative disease or disorder is Alzheimer's Disease, Parkinson's Disease, Creutzfeldt-Jacob disease, Dementia pugilistica, Down Syndrome, Gerstmann-Straussler-Scheinker disease, inclusion body myositis, prion protein cerebral amyloid angiopathy, traumatic brain injury, amyotrophic lateral sclerosis, parkinsonism-dementia complex of Guam, Non-Guamanian motor neuron disease with neurofibrillary tangles, argyrophilic grain dementia, corticobasal degeneration, Dementia Lewy Amyotrophic Lateral sclerosis, diffuse neurofibrillary tangles with calcification, frontotemporal dementia with parkinsonism linked to chromosome 17 (FTDP-17), Hallervorden-Spatz disease, multiple system atrophy, Niemann-Pick disease, type C, Pick's disease, progressive subcortical gliosis, progressive supranuclear palsy, Subacute sclerosing panencephalitis, Tangle only dementia, Postencephalitic Parkinsonism, Myotonic dystrophy, chronic traumatic encephalopathy (CTE), cerebral angiopathy or Lewy body dementia (LBD).

16. The method of claim 15, wherein the subject is in need of a treatment of Alzheimer's Disease, mild cognitive impairment (MCI) due to Alzheimer's Disease, or mild to moderate Alzheimer's Disease.

17. The method of claim 1, wherein the immunologically effective amount of the liposome comprises the first tau phosphopeptide at an amount of about 25 nmoles to about 750 nmoles per dose.

18. The method of claim 1, wherein the immunologically effective amount of the liposome comprises the first tau phosphopeptide at an amount of about 100 µg to about 2500 µg.

19. The method of claim 2, wherein the helper T cell epitope consists of an amino acid sequence selected from the group consisting of SEQ ID NO: 13 to SEQ ID NO: 17.

20. The method of claim 4, wherein the helper T cell epitope consists of an amino acid sequence selected from the group consisting of SEQ ID NO: 13 to SEQ ID NO: 17.

* * * * *